US010006012B2

(12) United States Patent
Maiyuran et al.

(10) Patent No.: US 10,006,012 B2
(45) Date of Patent: *Jun. 26, 2018

(54) POLYPEPTIDES HAVING CELLULOLYTIC ENHANCING ACTIVITY AND POLYNUCLEOTIDES ENCODING SAME

(71) Applicant: Novozymes, Inc., Davis, CA (US)

(72) Inventors: Suchindra Maiyuran, Gold River, CA (US); Randall Kramer, Lincoln, CA (US); Paul Harris, Carnation, WA (US)

(73) Assignee: Novozymes, Inc., Davis, CA (US)

( * ) Notice: Subject to any disclaimer, the term of this patent is extended or adjusted under 35 U.S.C. 154(b) by 675 days.

This patent is subject to a terminal disclaimer.

(21) Appl. No.: 14/518,841

(22) Filed: Oct. 20, 2014

(65) Prior Publication Data
US 2015/0040271 A1 Feb. 5, 2015

Related U.S. Application Data

(62) Division of application No. 14/052,176, filed on Oct. 11, 2013, now Pat. No. 8,865,445, which is a division of application No. 12/883,549, filed on Sep. 16, 2010, now Pat. No. 8,569,581.

(60) Provisional application No. 61/243,397, filed on Sep. 17, 2009, provisional application No. 61/243,531, filed on Sep. 18, 2009, provisional application No. 61/243,543, filed on Sep. 18, 2009, provisional application No. 61/243,679, filed on Sep. 18, 2009.

(51) Int. Cl.
| | |
|---|---|
| C12N 9/24 | (2006.01) |
| C12N 15/82 | (2006.01) |
| A01H 5/00 | (2006.01) |
| C12N 9/42 | (2006.01) |
| C11D 3/386 | (2006.01) |
| C12P 19/14 | (2006.01) |
| C12P 19/02 | (2006.01) |

(52) U.S. Cl.
CPC ............ *C12N 9/2437* (2013.01); *C11D 3/386* (2013.01); *C11D 3/3869* (2013.01); *C11D 3/38645* (2013.01); *C12P 19/02* (2013.01); *C12P 19/14* (2013.01); *C12Y 302/01* (2013.01); *Y02E 50/16* (2013.01)

(58) Field of Classification Search
None
See application file for complete search history.

(56) References Cited

U.S. PATENT DOCUMENTS

| 7,271,244 B2 | 9/2007 | Dotson et al. | |
|---|---|---|---|
| 2008/0299613 A1 | 12/2008 | Merino et al. | |
| 2015/0007369 A1* | 1/2015 | Lin ..................... | C12N 9/0071 800/298 |
| 2015/0082493 A1* | 3/2015 | Lin ..................... | C12N 9/0071 800/298 |

FOREIGN PATENT DOCUMENTS

| WO | 2003070940 A1 | 8/2003 | |
|---|---|---|---|
| WO | WO 2004031378 A2 * | 4/2004 | ............... A21D 2/24 |
| WO | 2005074647 | 8/2005 | |
| WO | 2005074656 | 8/2005 | |
| WO | 2007089290 | 8/2007 | |
| WO | 2008151079 A2 | 12/2008 | |
| WO | 2009033071 | 3/2009 | |
| WO | 2009085859 | 7/2009 | |
| WO | 2009085864 | 7/2009 | |
| WO | 2009085868 | 7/2009 | |
| WO | 2009085935 | 7/2009 | |
| WO | 2011057140 A1 | 5/2011 | |

OTHER PUBLICATIONS

Langston et al (Applied and Environmental Microbiology, Oct. 2011, p. 7007-7015).*
Dimarogona et al (Bioresource Technology, 2012).*
Horn et al (Biotechnology for Biofuels, 2012).*
Rosgaard et al., Efficiency of new fungal cellulose systems in boosting enzymatic degradation of barley straw lignocelluloses, V. 22, No. 2, Mar. 1, 2006, pp. 493-498.
Berka et al, 2011, Nature Biotechnol, 29(10), 922-929.
Guo et al, 2004, PNAS, 101(25), 9205-9210.
Himmel et al, 2007, Science, 315, 804-807.
Koseki et al, 2007, Appl Microbiol biotechnol, 77, 1279-1285.
Tyler et al, 2010, BMC Genomics, 11(600), 1-21.
Kikuchi, 2006, Genbank Acc No. CI612027.
Birren et al, 2006, NCBI Accession No. XP_001213388.
Galagan et al, 2006, NCBI Accession No. XP_958583.1.
Nierman et al, 2006, NCBI Accession No. XP_001259147.
Nierman et al, 2006, NCBI Accession No. XP_748707.

* cited by examiner

*Primary Examiner* — Lee A Visone
(74) *Attorney, Agent, or Firm* — Robert Starnes

(57) ABSTRACT

The present invention relates to isolated polypeptides having cellulolytic enhancing activity and isolated polynucleotides encoding the polypeptides. The invention also relates to nucleic acid constructs, vectors, and host cells comprising the polynucleotides as well as methods of producing and using the polypeptides.

36 Claims, 15 Drawing Sheets

```
      M   K   F   S   L   V   S   L   L   A   Y   G   L   S   V   E   A   H   S   I   F   Q   R   V
  1 ATGAAGTTCTCACTGGTGTCTCTGCTGGCTTACGGCCTCTCGGTCGAGGCGCACTCCATCTTCCAGAGAGTC
      S   V   N   G   Q   D   Q   G   L   L   T   G   L   R   A   P   S   N   N   N   P   V   Q   D
 73 TCGGTCAACGGCCAAGACCAAGGCCTGCTCACCGGCCTCCGCGCTCCAAGCAACAACAACCCAGTGCAAGAT
      V   N   S   Q   N   M   I   C   G   Q   S   G   S   K   S   Q   T   V   I   N   V   K   A   G
145 GTCAACAGCCAGAACATGATTTGCGGCCAGTCGGGCTCCAAGTCGCAGACCGTTATCAACGTCAAGGCCGGC
      D   R   I   G   S   L   W   Q   H   V   I   G   G   A   Q   F   S   G   D   P   D   N   P   I
217 GACAGGATCGGCTCGCTCTGGCAGCATGTCATCGGCGGCGCCCAGTTTTCGGGTGACCCGGACAACCCGATC
      A   H   S   H   K   G   P   V   M   A   Y   L   A   K   V   D   N   A   A   S   A   S   Q   T
289 GCCCACTCGCACAAGGGCCCCGTGATGGCGTACCTTGCTAAGGTCGACAATGCCGCGTCCGCGAGCCAAACG
      G   L   K   W   F   K   I   W   Q   D   G   F   D   T   S   S   K   T   W   G   V   D   N   L
361 GGTCTGAAGTGGTTCAAGATCTGGCAGGACGGGTTCGATACCAGCAGCAAGACATGGGGCGTCGACAACCTG
      I   K   N   N   G   W   V   Y   F   H   L   P   Q   C   L   A   P   G   Q   Y   L   L   R   V
433 ATCAAGAACAACGGCTGGGTGTACTTCCACCTGCCGCAGTGCCTCGCTCCGGGCCAGTATCTCCTGCGCGTC
      E   V   L   A   L   H   S   A   Y   Q   Q   G   Q   A   Q   F   Y   Q   S   C   A   Q   I   N
505 GAGGTTCTGGCGCTGCACTCGGCGTACCAGCAGGGCCAGGCCCAGTTCTACCAGTCCTGCGCCCAGATCAAC
      V   S   G   S   G   S   F   S   P   S   Q   T   V   S   I   P   G   V   Y   S   A   T   D   P
577 GTCTCCGGCTCCGGGTCCTTCAGCCCGTCCCAGACGGTCAGCATCCCGGGCGTCTACAGCGCCACCGACCCG
      S   I   L   I   N   I   Y   G   S   T   G   Q   P   D   N   G   G   K   A   Y   N   P   P   G
649 AGCATCCTCATCAACATCTACGGCAGCACGGGGCAGCCCGACAACGGCGGCAAGGCTTACAACCCCCCTGGA
      P   A   P   I   S   C   *
721 CCCGCCCCGATCTCCTGCTGA
```

FIG. 1

```
      M   R   T   T   F   A   A   A   L   A   A   F   A   A   Q   E   V   A   G   H   A   I   F   Q
  1 ATGAGGACGACATTCGCCGCCGCGTTGGCAGCCTTCGCTGCGCAGGAAGTGGCAGGCCATGCCATCTTCCAA
      Q   L   W   H   G   S   S   C   V   R   M   P   L   S   N   S   P   V   T   N   V   G   S   R
 73 CAGCTCTGGCACGGCTCCTCCTGCGTCCGCATGCCGCTGTCGAACTCGCCCGTCACGAACGTCGGCAGCAGG
      D   M   I   C   N   A   G   T   R   P   V   S   G   K   C   P   V   K   A   G   G   T   V   T
145 GACATGATCTGCAACGCCGGCACGCGCCCCGTCAGCGGGAAGTGCCCCGTCAAGGCCGGCGGCACCGTGACG
      V   E   M   H   Q   Q   P   G   D   R   S   C   N   N   E   A   I   G   G   A   H   W   G   P
217 GTTGAGATGCACCAGCAACCCGGGGATCGGTCGTGTAACAACGAAGCCATCGGCGGCGCCCACTGGGGACCG
      V   Q   V   Y   L   S   K   V   E   D   A   S   T   A   D   G   S   T   G   W   F   K   I   F
289 GTGCAGGTGTACCTCAGCAAGGTGGAGGACGCGAGCACGGCGGACGGGTCGACGGGCTGGTTCAAGATCTTC
      A   D   T   W   S   K   K   A   G   S   S   V   G   D   D   D   N   W   G   T   R   D   L   N
361 GCGGACACGTGGTCCAAGAAGGCGGGCAGCTCGGTGGGGGACGACGACAACTGGGGCACGCGCGACCTCAAC
      A   C   C   G   K   M   Q   V   K   I   P   A   D   I   P   S   G   D   Y   L   L   R   A   E
433 GCGTGCTGCGGCAAGATGCAGGTCAAGATCCCGGCGGACATCCCGTCGGGCGACTACCTGCTGCGGGCGGAG
      A   L   A   L   H   T   A   G   Q   V   G   G   A   Q   F   Y   M   S   C   Y   Q   I   T   V
505 GCGCTGGCGCTGCACACGGCGGGCCAGGTGGGCGGCGCGCAGTTCTACATGAGCTGCTACCAGATCACCGTG
      S   G   G   G   S   A   S   P   A   T   V   K   F   P   G   A   Y   S   A   N   D   P   G   I
577 TCGGGCGGCGGCAGCGCCAGCCCGGCCACCGTCAAGTTCCCCGGCGCCTACAGCGCCAACGACCCGGGCATC
      H   I   N   I   H   A   A   V   S   N   Y   V   A   P   G   P   A   V   Y   S   G   G   T   T
649 CACATCAACATCCACGCGGCCGTGTCCAACTACGTCGCGCCCGGCCCGGCCGTCTATTCCGGCGGCACGACC
      K   V   A   G   S   G   C   Q   G   C   E   N   T   C   K   V   G   S   S   P   T   A   T   A
721 AAGGTGGCCGGGTCCGGGTGCCAAGGCTGCGAGAACACGTGCAAGGTCGGCTCGTCGCCCACGGCGACGGCG
      P   S   G   K   S   G   A   G   S   D   G   G   A   G   T   D   G   G   S   S   S   S   P
793 CCGTCGGGCAAGAGCGGCGCGGGTTCCGACGGCGGCGCTGGGACCGACGGCGGGTCTTCGTCTTCGAGCCCC
      D   T   G   S   A   C   S   V   Q   A   Y   G   Q   C   G   G   N   G   Y   S   G   C   T   Q
865 GACACGGGCAGCGCGTGCAGCGTGCAGGCCTACGGGCAGTGCGGCGGGAACGGGTACTCGGGTTGCACCCAG
      C   A   P   G   Y   T   C   K   A   V   S   P   P   Y   Y   S   Q   C   A   P   S   S   *
937 TGCGCGCCCGGCTATACTTGCAAGGCGGTCTCTCCGCCGTACTATTCGCAGTGCGCCCCTTCTTCTTAG
```

FIG. 2

```
      M  K  L  S  V  A  I  A  V  L  A  S  A  L  A  E  A  H  Y  T  F  P  S  I
  1 ATGAAGCTGAGCGTTGCCATCGCCGTGCTGGCGTCGGCTCTTGCCGAGGCTCACTACACCTTCCCCAGCATC
      G  N  T  A  D  W  Q  Y  V  R  I  T  T  N  Y  Q  S  N  G  P  V  T  D  V
 73 GGAAACACCGCTGACTGGCAGTATGTGCGGATTACAACGAACTACCAGAGCAACGGGCCGGTGACGGACGTC
      T  S  D  Q  I  R  C  Y  E  R  N  P  G  T  G  A  Q  G  I  Y  N  V  T  A
145 ACCTCGGATCAAATTCGGTGCTACGAACGGAACCCAGGCACGGGAGCGCAGGGCATATACAACGTCACCGCC
      G  Q  T  I  N  Y  N  A  K  A  S  I  S  H  P  G  P  M  S  F  Y  I  A  K
217 GGCCAGACCATCAACTACAACGCGAAGGCGTCCATCTCCCACCCGGGGCCCATGTCCTTCTACATTGCTAAG
      V  P  A  G  Q  T  A  A  T  W  D  G  K  G  A  V  W  T  K  I  Y  Q  D  M
289 GTTCCCGCCGGCCAAACCGCTGCGACCTGGGACGGTAAGGGGGCTGTGTGGACCAAGATCTACCAGGACATG
      P  K  F  G  S  S  L  T  W  P  T  M  G  A  K  S  V  P  V  T  I  P  R  C
361 CCCAAGTTCGGCAGCAGCCTGACCTGGCCCACCATGGGCGCCAAGTCTGTCCCCGTCACCATCCCTCGTTGC
      L  Q  N  G  D  Y  L  L  R  A  E  H  I  A  L  H  S  A  S  S  V  G  G  A
433 CTCCAGAACGGCGATTACCTTCTGCGAGCCGAGCACATCGCTCTACACAGCGCGAGCAGCGTCGGTGGCGCC
      Q  F  Y  L  S  C  A  Q  L  T  V  S  G  G  S  G  T  W  N  P  K  N  R  V
505 CAGTTCTACCTCTCGTGCGCCCAGCTTACTGTCAGCGGCGGCAGTGGCACCTGGAACCCCAAGAACCGGGTC
      S  F  P  G  A  Y  K  A  T  D  P  G  I  L  I  N  I  Y  Y  P  V  P  T  S
577 TCCTTCCCCGGCGCTTACAAGGCAACAGACCCGGGCATCTTGATCAACATCTACTACCCCGTGCCGACCAGC
      Y  S  P  P  G  P  P  A  E  T  C  *
649 TACTCGCCGCCCGGCCCGCCGGCTGAGACGTGCTAA
```

FIG. 3

```
      M   K   L   S   S   Q   L   A   A   L   T   L   A   A   A   S   V   S   G   H
  1 ATGAAGCTGTCATCCCAGCTCGCCGCCCTCACGCTGGCCGCGGCCTCCGTGTCAGGCCAC
      Y   I   F   E   Q   I   A   H   G   G   T   K   F   P   P   Y   E   Y   I   R
 61 TACATCTTCGAGCAGATTGCCCATGGCGGCACCAAGTTCCCACCTTACGAGTACATCCGA
      R   N   T   N   Y   N   S   P   V   T   S   L   S   S   N   D   L   R   C   N
121 AGAAACACGAACTATAACAGCCCTGTCACCAGTCTCTCGTCGAACGACCTGCGATGCAAC
      V   G   G   E   T   A   G   N   T   T   V   L   D   V   K   A   G   D   S   F
181 GTAGGCGGCGAGACGGCTGGCAACACGACCGTCCTCGACGTGAAGGCGGGCGACTCCTTC
      T   F   Y   S   D   V   A   V   Y   H   Q   G   P   I   S   L
241 ACCTTCTACTCGGACGTGGCCGTGTACCACCAGGGGCCCATCTCACTGTGCGTGCCCCGG
301 GCCAACTTTGATCAGTCCCAAGCGGACTGTCCGCTCGCCTGGATAACCACAATTGACTGA
                      Y   M   S   K   A   P   G   S   V   V   D   Y   D   G   S   G
361 CAGCCCGCACAGCTACATGTCCAAGGCTCCGGCTCCGTCGTGGACTACGACGGCTCCGG
          D   W   F   K   I   H   D   W   G   P   T   F   S   N   G   Q   A   S   W   P
421 CGACTGGTTCAAGATCCACGACTGGGGCCCGACCTTCAGCAACGGCCAGGCCTCGTGGCC
          L   R
481 GCTGCGGGGTGCGTCCCTTCCCTTTCCCTCCCCCTTCCTCCCCCTTCCTCCCCCCCTTTC
                                                                          D   N   Y   Q   N
541 CCCCCTTTTCTGTCTGGTCGCACGCCCTGCTGACGTCCCCGTAGACAACTACCAGTACAA
          I   P   T   C   I   P   N   G   E   Y   L   L   R   I   Q   S   L   A   I   H
601 CATCCCGACGTGCATCCCGAACGGCGAGTACCTGCTGCGCATCCAGTCGCTGGCGATCCA
          N   P   G   A   T   P   Q   F   Y   I   S   C   A   Q   V   R   V   S   G   G
661 CAACCCGGGCGCCACGCCGCAGTTCTACATCAGCTGCGCGCAGGTCCGGGTCTCGGGCGG
          G   S   A   S   P   S   P   T   A   K   I   P   G   A   F   K   A   T   D   P
721 CGGCAGCGCCTCCCCCTCCCCAACGGCCAAGATCCCCGGCGCGTTCAAGGCGACCGATCC
          G   Y   T   A   N
781 CGGGTATACCGCGAATGTGAGTGCCCTATGTTCCTTGCGCTCCTTGTTCCTTGCTCCTTG
841 CTCGGCGTGCTTGAACGCTACGGGCTGTGGAGGGAGGGATGGATGGATGAATAGGATGCT
                              I   Y   N   N   F   H   S   Y   T   V   P   G   P
901 GACTGATGGTGGGACACCAGATTTACAATAACTTCCACTCGTATACGGTGCCGGGTCCGG
      A   V   F   Q   C   *
961 CGGTCTTTCAGTGCTAG
```

FIG. 6

```
         M   P   S   F   A   S   K   T   L   L   S   T   L   A   G   A   A   S   V   A   A   H
   1 ATGCCTTCTTTCGCCTCCAAGACTCTCCTTTCCACCCTGGCGGGTGCCGCATCCGTGGCCGCCCAC
         G   H   V   S   N   I   V   I   N   G   V   S   Y   Q   G   Y   D   P   T   S   F   P
  67 GGGCACGTGTCGAACATCGTCATCAACGGGGTCTCGTACCAGGGTTACGATCCGACCTCCTTCCCT
         Y   M   Q   N   P   P   I   V   V   G   W   T   A   A   D   T   D   N   G   F   V   A
 133 TACATGCAGAACCCGCCCATCGTGGTCGGCTGGACTGCCGCCGACACGGACAACGGCTTTGTTGCC
         P   D   A   F   A   S   G   D   I   I   C   H   K   N   A   T   N   A   K   G   H   A
 199 CCGGATGCCTTCGCCAGTGGCGATATCATCTGCCACAAGAACGCCACCAACGCCAAGGGCCACGCC
         V   V   A   A   G   D   K   I   F   I   Q   W   N   T   W   P   E   S   H   H   G   P
 265 GTGGTCGCCGCGGGAGACAAGATCTTCATCCAGTGGAACACATGGCCCGAGTCCCACCACGGCCCC
         V   I   D   Y   L   A   S   C   G   S   A   S   C   E   T   V   D   K   T   K   L   E
 331 GTCATCGACTACCTCGCGAGCTGCGGCAGCGCGTCCTGCGAGACCGTCGACAAGACCAAGCTCGAG
         F   F   K   I   D   E   V   G   L   V   D   G   S   S   A   P   G   V   W   G   S   D
 397 TTCTTCAAGATCGACGAGGTCGGCCTGGTCGACGGCAGCTCGGCGCCCGGTGTGTGGGGCTCCGAC
         Q   L   I   A   N   N   N   S   W   L   V   E   I   P   P   T   I   A   P   G   N   Y
 463 CAGCTCATCGCCAACAACAACTCGTGGCTCGTCGAGATCCCGCCCACCATCGCGCCGGGCAACTAC
         V   L   R   H   E   I   I   A   L   H   S   A   E   N   A   D   G   A   Q   N   Y   P
 529 GTCCTGCGCCACGAGATCATCGCGCTGCACAGCGCCGAAAACGCCGACGGCGCCCAGAACTACCCG
         Q   C   F   N   L   Q   I   T   G   T   G   T   A   T   P   S   G   V   P   G   T   S
 595 CAGTGCTTCAACCTGCAGATCACCGGCACCGGCACCGCCACCCCCTCCGGCGTCCCCGGCACCTCG
         L   Y   T   P   T   D   P   G   I   L   V   N   I   Y   S   A   P   I   T   Y   T   V
 661 CTCTACACCCCGACCGACCCGGGCATCCTCGTCAACATCTACAGCGCCCCGATCACCTACACCGTC
         P   G   P   A   L   I   S   G   A   V   S   I   A   Q   S   S   S   A   I   T   A   S
 727 CCGGGGCCGGCCCTCATCTCCGGCGCCGTCAGCATCGCCCAGTCCTCCTCCGCCATCACCGCCTCC
         G   T   A   L   T   G   S   A   T   A   P   A   A   A   A   T   T   T   S   T   T
 793 GGCACCGCCCTGACCGGCTCTGCCACCGCACCCGCCGCCGCCGCTGCTACCACAACTTCCACCACC
         N   A   A   A   A   A   T   S   A   A   A   A   A   G   T   S   T   T   T   T   S   A
 859 AACGCCGCGGCTGCTGCTACCTCTGCTGCTGCTGCTGCTGGTACTTCCACAACCACCACCAGCGCC
         A   A   V   V   Q   T   S   S   S   S   S   A   P   S   S   A   A   A   A   A   T
 925 GCGGCCGTGGTCCAGACCTCCTCCTCCTCCTCCTCCGCCCCGTCCTCTGCCGCCGCCGCCGCCACC
         T   T   A   A   A   S   A   R   P   T   G   C   S   S   G   R   S   R   K   Q   P   R
 991 ACCACCGCGGCTGCCAGCGCCCGCCCGACCGGCTGCTCCTCTGGCCGCTCCAGGAAGCAGCCGCGC
         R   H   A   R   D   M   V   V   A   R   G   A   E   E   A   N   *
1057 CGCCACGCGCGGGATATGGTGGTTGCGCGAGGGGCTGAGGAGGCAAACTGA
```

FIG. 8

```
      M   P   P   A   L   P   Q   L   L   T   T   V   L   T   A   L   T   L   G   S   T   A
  1 ATGCCGCCCGCACTCCCTCAACTCCTAACCACGGTCCTGACCGCCCTCACCCTCGGTTCCACCGCC
      L   A   H   S   H   L   A   Y   I   I   V   N   G   K   L   Y   Q   G   F   D   P   R
 67 CTCGCCCACTCACACCTCGCGTACATTATCGTTAACGGCAAGCTCTACCAGGGCTTCGACCCGCGC
      P   H   Q   A   N   Y   P   S   R   V   G   W   S   T   G   A   V   D   D   G   F   V
133 CCGCACCAGGCCAACTACCCTTCCCGGGTCGGGTGGTCCACCGGCGCCGTCGACGACGGCTTCGTC
      T   P   A   N   Y   S   T   P   D   I   I   C   H   I   A   G   T   S   P   A   G   H
199 ACGCCGGCCAACTACTCCACCCCGGACATCATTTGCCACATCGCCGGCACCAGCCCGGCCGGCCAC
      A   P   V   R   P   G   D   R   I   H   V   Q   W   N   G   W   P   V   G   H   I   G
265 GCGCCCGTGCGCCCGGGCGACCGCATCCACGTCCAGTGGAACGGCTGGCCGGTCGGCCACATCGGT
      P   V   L   S   Y   L   A   R   C   E   S   D   T   G   C   T   G   Q   N   K   T   A
331 CCCGTGCTGTCGTACCTCGCCCGCTGCGAGTCGGACACGGGCTGCACGGGCCAGAACAAGACCGCG
      L   R   W   T   K   I   D   D   S   S   P   T   M   Q   N   V   A   G   A   G   T   Q
397 CTGCGGTGGACCAAGATCGACGACTCCAGCCCGACCATGCAGAACGTCGCCGGCGCGGGCACCCAG
      G   E   G   T   P   G   K   R   W   A   T   D   V   L   I   A   A   N   N   S   W   Q
463 GGCGAGGGCACCCCCGGCAAGCGCTGGGCCACCGACGTGCTGATCGCCGCCAACAACAGCTGGCAG
      V   A   V   P   A   G   L   P   T   G   A   Y   V   L   R   N   E   I   I   A   L   H
529 GTCGCCGTGCCGGCGGGGCTGCCGACCGGCGCGTACGTGCTGCGCAACGAGATCATCGCGCTGCAC
      Y   A   A   R   K   N   G   A   Q   N   Y   P   L   C   M   N   L   W   V   D   A   S
595 TACGCGGCGAGGAAGAACGGGGCGCAGAACTATCCGCTCTGCATGAACCTGTGGGTGGACGCCAGT
      G   D   N   S   S   V   A   A   T   T   A   A   V   T   A   G   G   L   Q   M   D   A
661 GGTGATAATAGTAGTGTGGCTGCAACGACGGCGGCGGTGACGGCGGGGGGTCTGCAGATGGATGCG
      Y   D   A   R   G   F   Y   K   E   N   D   P   G   V   L   V   N   V   T   A   A   L
727 TATGACGCGCGCGGGTTCTACAAGGAGAACGATCCGGGCGTGCTGGTCAATGTCACGGCCGCGCTG
      S   S   Y   V   V   P   G   P   T   V   A   A   G   A   T   P   V   P   Y   A   Q   Q
793 TCGTCGTATGTCGTGCCCGGGCCGACGGTGGCGGCGGGCGCCACGCCGGTGCCGTACGCGCAGCAG
      S   P   S   V   S   T   A   A   G   T   P   V   V   V   T   R   T   S   E   T   A   P
859 AGCCCGAGCGTGTCGACGGCGGCGGGCACGCCCGTCGTCGTTACAAGGACTAGCGAGACGGCGCCG
      Y   T   G   A   M   T   P   T   V   A   A   R   M   K   G   R   G   Y   D   R   R   G
925 TACACGGGCGCCATGACGCCGACGGTTGCGGCGAGGATGAAGGGGAGGGGGTATGATCGGCGGGGT
      *
991 TAG
```

FIG. 10

```
        M  K  T  F  T  A  L  L  A  A  A  G  L  V  A  G  H  G  Y  V  D  N
   1 ATGAAGACATTCACCGCCCTCCTGGCCGCAGCCGGCCTCGTCGCCGGCCATGGATATGTCGACAAC
        A  T  I  G  G  Q  F  Y  Q
  67 GCCACCATTGGCGGCCAGTTTTATCAGGTACTCTACCGCTTCACCCAAGGTCCGCTGGCCACAACT
 133 CTATAGGTGTCATAAATTAACAAGCCACCGTCCCGCAGTTCTATCAGGTGTGCTCGCTACCGACCA
 199 TGTGGTCCCGTCTCAGCAAGCCACTCACACGCCCATGATCCCCTAGCCTTACGTCGACCCGTATTT
                                                                 N  P
 265 AGCAACCTTGGCACGTAGTATTTATTGTCCCAAATATTGAGCTGAACTGCACCTCCCTAGAATCCC
        A  V  L  T  F  F  Q  P  D  R  V  S  R  S  I  P  G  N  G  P  V  T
 331 GCGGTGCTAACATTCTTTCAGCCCGACAGGGTCTCTCGATCCATCCCGGGCAACGGCCCGGTCACG
        D  V  T  L  I  D  L  Q  C  N  A  N  S  T  P  A  K  L  H  A  T  A
 397 GACGTCACTCTCATCGACCTGCAGTGCAACGCCAATTCCACCCCGGCCAAGCTCCACGCCACTGCC
        A  A  G  S  D  V  I  L  R  W  T  L  W  P  E  S  H  V  G  P  V  I
 463 GCTGCCGGCTCGGACGTGATTCTCCGCTGGACGCTCTGGCCTGAGTCGCACGTTGGCCCCGTCATC
        T  Y  M  A  R  C  P  D  T  G  C  Q  D  W  M  P  G  T  S
 529 ACCTACATGGCCCGCTGCCCCGACACGGGCTGCCAGGACTGGATGCCGGGCACTTCGTAGGAGCCC
 595 ATCTTGCACCATATCCATTTCAACCGGCCACACGCACTGACCCATATGTCTGTCTACCCCTGCAGT
        A  V  W  F  K  I  E  G  G  R  D  G  T  S  N  T  W  A  D  V  R
 661 GCGGTCTGGTTCAAGATCAAGGAGGGCGGCCGCGACGGCACTTCCAACACCTGGGCCGACGTACGT
        V  P  R  P  R  E  P  K  P  P  L  Q  Q  S  K  H  L  N  S  P  S  L
 727 GTACCCCGTCCCAGAGAGCCAAAGCCCCCCCTTCAACAAAGCAAACATCTCAATAGCCCGAGCCTA
        R  T  N  P  S  P  S  P  S  K  T  Q  T  P  L  M  T  A  P  T  S  Y
 793 CGCACTAACCCCTCTCCTTCCCCCTCGAAAACACAGACCCCGCTGATGACGGCGCCCACCTCGTAC
        T  Y  T  I  P  S  C  L  K  K  G  Y  Y  L  V  R  H  E  I  I  A  L
 859 ACGTACACGATCCCCTCCTGCCTGAAGAAGGGCTACTACCTGGTCCGCCACGAGATCATCGCGCTG
        H  A  A  Y  T  Y  P  G  A  Q  F  Y  P  G  C  H  Q  L  N  V  T  G
 925 CACGCCGCCTACACCTACCCCGGCGCGCAGTTCTACCCGGGCTGCCACCAGCTCAACGTCACGGGC
        G  G  S  T  V  P  S  S  G  L  V  A  F  P  G  A  Y  K  G  S  D  P
 991 GGCGGGTCCACCGTACCGTCGAGCGGCCTGGTGGCCTTTCCCGGGGCGTACAAGGGCAGTGACCCC
        G  I  T  Y  D  A  Y  K
1057 GGGATTACGTACGATGCGTATAAAGGTGGGTTGGCTGGTTGGCCCAGGTCTTGGTGATGGGGGAAT
                                                           A  Q  T  Y
1123 GTGGTGATGAGGTTTATTATTTGGGATCCCGTGGCTAACGTAACCCTGGGTGTAGCGCAAACGTAC
        Q  I  P  G  P  A  V  F  T  C  *
1189 CAGATTCCTGGGCCGGCGGTCTTTACTTGCTGA
```

FIG. 11

```
              M   A   L   L   L   L   A   G   L   A   I   L   A   G   P   A   H   A   H   G   G   L
  1 ATGGCCTTGCTGCTCTTGGCAGGCTTGGCCATTCTGGCCGGGCCGGCTCATGCCCACGGCGGCCTC
      A   N   Y   T   V   G   N   T   W   Y   R   G
 67 GCCAACTACACAGTGGGCAACACCTGGTATAGGGGGTGCGTAAGGGGGGCACCGACAACGCCTGCT
                                                      Y   D   P   F   T   P   A   A
133 TAGTAACTCCACCATTTCGAGCGGGCTAACACCGGGCGCAGCTACGACCCCTTCACGCCGGCGGCC
      D   Q   I   G   Q   P   W   M   I   Q   R   A   W   D   S   I   D   P   I   F   S   V
199 GACCAGATCGGCCAGCCGTGGATGATCCAACGCGCGTGGGACTCGATCGACCCGATCTTCAGCGTC
      N   D   K   A   L   A   C   N   T   P   A   T   A   P   T   S   Y   I   P   I   R   A
265 AACGACAAGGCGCTCGCCTGCAACACCCCGGCCACGGCGCCGACCTCTTACATTCCCATCCGCGCG
      G   E   N   I   T   A   V   Y   W   Y   W   L   H   P   V   G   P   M   T   A   W   L
331 GGCGAGAACATCACGGCCGTGTACTGGTACTGGCTGCACCCGGTGGGCCCCATGACGGCGTGGCTG
      A   R   C   D   G   D   C   R   D   A   D   V   N   E   A   R   W   F   K   I   W   E
397 GCGCGGTGCGACGGCGACTGCCGCGACGCCGACGTCAACGAGGCGCGCTGGTTCAAGATCTGGGAG
      A   G   L   L   S   G   P   N   L   A   E   G   M   W   Y   Q   K   A   F   Q   N   W
463 GCCGGCCTGCTCAGCGGGCCGAACCTGGCCGAGGGCATGTGGTACCAGAAGGCGTTCCAGAACTGG
      D   G   S   P   D   L   W   P   V   T   I   P   A   G   L   K   S   G   L   Y   M   I
529 GACGGCAGCCCGGACCTGTGGCCCGTCACGATCCCGGCCGGGCTGAAGAGCGGCCTGTACATGATC
      R   H   E   I   L   S   I   H   V   E   D   K   P   Q   F   Y   P   E   C   A   H   L
595 CGGCACGAGATCTTGTCGATCCACGTCGAGGATAAACCGCAGTTTTATCCCGAGTGTGCGCATCTG
      N   V   T   G   G   G   D   L   L   P   P   D   E   F   L   V   K   F   P   G   A   Y
661 AATGTGACCGGGGGTGGGGACCTGCTGCCGCCTGATGAGTTTTTGGTGAAGTTCCCGGGCGCTTAC
      K   E   D                                                                             N
727 AAAGAAGATAGTGAGTGAAACGCGAAGCTTCGGTAGCCATTGGGTTGCGCTGATGGAGGTTAGACC
      P   S   I   K   I   N   I   Y   S   D   Q   Y   A   N   T   T
793 CGTCGATCAAGATCAATATCTACTCGGACCAGTACGCCAATACAACGGTGAGTGTAACAGGTCGAG
                                                        N   Y   T   I   P   G   G   P   I   W
859 CAAAACCAAACAGATGCCGATGACTGATGATCTCAGAATTACACAATTCCCGGAGGGCCGATATGG
      D   G   *
925 GATGGGTGA
```

FIG. 12

```
            M   M   P   S   L   V   R   F   S   M   G   L   A   T   A   F   A   S   L   S   T   A
   1 ATGATGCCGTCCCTTGTTCGCTTCTCAATGGGTCTGGCGACCGCCTTCGCCTCGCTGTCCACAGCA
            H   T   V   F   T   T   L   F   I   N   G   V   D   Q   G   D   G   T   C   I   R   M
  67 CATACCGTCTTCACCACGCTTTTCATCAACGGCGTCGACCAAGGGGACGGGACCTGCATCCGCATG
            A   K   K   G   S   V   C   T   H   P   I   A   G   G   L   D   S   P   D   M   A   C
 133 GCCAAGAAGGGCAGCGTTTGCACCCATCCCATTGCTGGTGGCCTCGACAGCCCAGACATGGCTTGT
                                                                                              G
 199 GGTATGCCCTCTGCGTTTCCCCTGCGAGAGCTTTCCTCGAGCTAACCCAATGCCGCGTTGCCCAGG
            R   D   G   Q   Q   A   V   A   F   T   C   P   A   P   A   G   S   K   L   S   F   E
 265 CCGAGACGGACAACAAGCCGTGGCATTCACCTGCCCAGCCCCGGCGGGCTCCAAGTTGAGCTTCGA
            F   R   M   W   A   D   A   S   Q   P   G   S   I   D   P   S   H   L   G   S   T   A
 331 GTTCCGCATGTGGGCCGACGCCTCTCAGCCCGGCTCTATCGACCCATCCCACCTCGGCTCGACGGC
            I   Y   L   K   Q   V   S   N   I   S   S   D   S   A   A   G   P   G   W   F   K   I
 397 AATCTACCTCAAACAAGTCTCCAACATCAGCTCCGACTCGGCTGCCGGCCCTGGCTGGTTCAAGAT
            Y   A   E   G   Y   D   T   A   A   K   K   W   A   T   E   K   L   I   D   N   G   G
 463 CTACGCCGAGGGCTACGACACAGCCGCCAAGAAGTGGGCCACAGAGAAGCTCATCGACAACGGCGG
            L   L   S   I   E   L   P   P   T   L   P   A   G   Y   Y   L   A   R   S   E   I   V
 529 CCTGCTGAGCATCGAGCTTCCGCCCACTCTGCCGGCGGGATACTACCTCGCCCGCAGCGAGATCGT
            T   I   Q   N   V   T   N   D   H   V   D   P   Q   F   Y   V   G   C   A   Q   L   F
 595 CACCATCCAGAACGTCACCAACGACCACGTCGACCCGCAGTTCTACGTTGGCTGCGCACAGCTCTT
            V   Q   G   P   P   T   T   P   T   V   P   P   D   R   L   V   S   I   P   G   H   V
 661 CGTCCAGGGGCCTCCGACCACCCCCACCGTCCCGCCAGACAGACTCGTCTCCATCCCGGGCCACGT
            H   A   S   D   P   G   L   T   F   N   I   W   R   D   D   P   S   K   T   A   Y   T
 727 CCATGCCTCCGACCCGGGGCTGACCTTCAACATCTGGCGCGACGACCCCTCCAAGACGGCCTACAC
            V   V   G   P   A   P   F   S   P   T   A   A   P   T   P   T   S   T   N   T   N   G
 793 CGTCGTCGGCCCGGCCCCCTTCTCCCCCACCGCCGCCCCCACCCCCACCTCCACCAACACCAACGG
            Q   Q   Q   Q   Q   Q   Q   Q   A   I   K   Q   T   D   G   V   I   P   A   D   C   Q
 859 GCAGCAACAACAACAACAGCAACAGGCGATAAAGCAGACGGACGGCGTGATCCCCGCCGACTGCCA
            L   K   N   A   N   W   C   G   A   E   V   P   A   Y   A   D   E   A   G   C   W   A
 925 GCTCAAGAACGCCAACTGGTGCGGCGCCGAGGTGCCCGCGTACGCCGACGAGGCCGGCTGCTGGGC
            S   S   A   D   C   F   A   Q   L   D   A   C   Y   T   S   A   P   P   T   G   S   R
 991 GTCGTCGGCCGACTGCTTCGCCCAGCTGGACGCCTGCTACACGTCGGCGCCGCCCACGGGCAGCCG
            G   C   R   L   W   E   D   W   C   T   G   I   Q   Q   G   C   R   A   G   R   W   R
1057 CGGCTGCCGGCTGTGGGAGGACTGGTGCACCGGCATTCAGCAGGGCTGCCGCGCGGGGCGGTGGCG
            G   P   P   P   F   H   G   E   G   A   A   A   E
1123 GGGGCCGCCGCCCTTTCATGGGGAGGGGGCAGCAGCGGAGGTGTGAACGGTTCGGGGACGGGTGGC
                                                                              T   A   S
1189 GGTGGTGGTGGTGGTGGTGGTGGCACTGGCTCTTCTTCGGCTTCTGCCCCGACGGAGACGGCCTCT
            A   G   R   G   G   A   R   I   A   A   V   A   G   C   G   G   G   T   G   D   M   V
1255 GCTGGCCGGGGGGGCGCAAGAATAGCTGCCGTGGCCGGCTGCGGAGGCGGGACAGGAGACATGGTT
            E   E   V   F   L   F   Y   W   D   A   C   S   G   W   R   R   S   R   G   G   G   S
1321 GAAGAGGTTTTCCTCTTTTATTGGGACGCTTGCAGCGGCTGGCGACGGAGCCGTGGTGGTGGTTCG
            I   L   A   R   L   I   L   H   V   L   L   P   L   L   R   P   R   R   A   P   R   V
1387 ATTCTTGCGAGGCTTATCCTTCATGTCCTTCTTCCACTTTTGAGACCGAGGCGAGCCCCTCGAGTC
            H   L   L   L   F   H   L   Y   L   N   F   C   Y   P   G   T   S   G   F   Y   N   R
1453 CATTTACTTCTCTTCCACCTGTACCTCAACTTCTGTTATCCAGGAACCAGTGGTTTCTATAATCGC
            L   S   I   K   L   G   I   W   P   S   K   M   S   P   D   V   A   H   Y   V   K   *
1519 CTGAGCATTAAACTAGGCATATGGCCAAGCAAAATGTCGCCTGATGTAGCGCATTACGTGAAATAA
```

FIG. 13

```
      M  Q  L  L  V  G  L  L  L  A  A  V  A  A  R  A  H
  1 ATGCAGCTCCTCGTGGGCTTGCTGCTTGCAGCCGTGGCTGCTCGAGCACATT*GTATTTCTACCCCT*
                                                         Y  T
 67 *TTCCGCGTGCCTCCCAGCCTCAAGGCAAGAAGACGCACGCAGCAGCTAACGGACCCTATCAGACAC*
        F  P  R  L  V  V  N  G  Q  P  E  D  K  D  W  S  V  T  R  M  T  K
133 ATTTCCCAGACTCGTGGTAAATGGGCAGCCCGAGGACAAGGACTGGTCGGTTACGCGCATGACCAA
       N  A  Q  S  K  Q  G  V  Q  D  P  T  S  P  D  I  R  C  Y  T  S  Q
199 GAACGCGCAGAGCAAGCAGGGAGTCCAGGACCCGACCAGTCCCGACATTCGCTGCTACACGTCGCA
       T  A  P  N  V  A  T  V  P  A  G  A  T  V  H  Y  I  S  T  Q  Q  I
265 GACGGCGCCTAACGTGGCTACGGTCCCTGCCGGAGCCACCGTCCATTACATATCGACTCAGCAGAT
       N  H  P  G  P  T  Q  Y  Y  L  A  K  V  P  A  G  S  S  A  K  T  W
331 CAACCACCCGGGCCCGACGCAGTACTACCTCGCCAAGGTACCGGCGGGGTCGTCGGCCAAGACGTG
       D  G  S  G  A  V  W  F  K  I  S  T  T  M  P  Y  L  D  N  N  K  Q
397 GGACGGGTCAGGGGCCGTCTGGTTCAAGATCTCGACCACCATGCCTTACTTGGACAACAACAAGCA
       L  V  W  P  N  Q
463 GCTTGTCTGGCCGAATCAGA*GTAGGAACAATTCCCGCTCCAATCTTCGATTTGGCCTTGAGCTACG*
                                                           N  T  Y  T  T
529 *GCCGATTGCATGGAGAGACCGTTGACTGACGGGGCAACCCAACCTTCATCAGACACGTACACGAC*
       V  N  T  T  I  P  A  D  T  P  S  G  E  Y  L  L  R  V  E  Q  I  A
595 GGTCAACACGACCATCCCCGCCGATACGCCCAGTGGGGAATACCTCCTCCGGGTCGAGCAGATCGC
       L  H  L  A  S  Q  P  N  G  A  Q  F  Y  L  A  C  S  Q  I  Q  I  T
661 GCTGCACCTGGCCTCGCAGCCCAACGGGGCTCAGTTCTACCTGGCCTGCTCGCAGATCCAGATTAC
       G  G  G  N  G  T  P  G  P  L  V  A  L  P  G  A  Y  K  S  N  D  P
727 GGGCGGCGGCAACGGCACGCCCGGCCCGCTAGTCGCGTTGCCGGGGGCGTACAAGAGCAACGACCC
       G  I  L  V  N  I  Y  S  M  Q  P  G  D  Y  K  P  P  G  P  P  V  W
793 GGGCATTTTGGTCAACATCTACTCTATGCAGCCCGGCGATTACAAGCCGCCCGGGCCGCCGGTGTG
       S  G  *
859 GAGTGGCTGA
```

FIG. 14

```
          M  K  L  Y  L  A  A  F  L  G  A  V  A  T  P  G  A  F  A  H
   1 ATGAAGCTGTACCTGGCGGCCTTTCTAGGCGCCGTCGCCACCCCGGGAGCGTTCGCTCATCGTAGG
                                                                    Q  I  H
  67 TTCCCCGTCTATCTCCCTAGGGGTAGCACCACGACTAATTTCTCGTCGTCCCCCTGTAGAAATCCA
        G  I  L  L  V  N  G  T  E  T  P  E  W  K  Y  V  R
 133 CGGGATTCTACTTGTCAACGGCACCGAAACGCCGGAATGGAAATACGTCCGGTAATATCTACCTTG
                                                        D  V  A  W  E  G  A  Y  E
 199 CTCTCCTTCTTCCACAACCAGCCTAACACATCATCAGTGACGTGGCCTGGGAGGGCGCCTACGAAC
        P  E  K  Y  P  N  T  E  F  F  K  T  P  P  Q  T  D  I  N  N  P  N
 265 CGGAAAAATACCCCAACACCGAGTTCTTTAAGACGCCCCCGCAGACGGACATCAACAACCCGAACA
        I  T  C  G  R  N  A  F  D  S  A  S  K  T  E  T  A  D  I  L  A  G
 331 TCACCTGCGGCAGGAACGCGTTCGACTCGGCCAGCAAGACTGAGACGGCCGACATACTGGCCGGCT
        S  E  V  G  F  R  V  S  W  D  G  N  G  K  Y  G  V  F  W  H  P  G
 397 CAGAGGTCGGCTTCCGCGTCTCGTGGGACGGCAACGGCAAGTACGGCGTGTTCTGGCATCCCGGGC
        P  G  Q  I  Y  L  S  R  A  P  N  D  D  L  E  D  Y  R  G  D  G  D
 463 CGGGGCAGATCTACCTCTCTCGTGCTCCGAACGACGACCTGGAGGACTACCGCGGCGACGGAGACT
        W  F  K  I  A  T  G  A  A  V  S  N  T  E  W  L  L  W  N  K  H  D
 529 GGTTCAAGATCGCAACCGGCGCCGCCGTCTCCAATACCGAGTGGCTGCTGTGGAACAAGCATGACG
 595 TGAGCCCCAACATTCCTCGCCCAATCGATCCCCAACCTGGTCACCATGGCGGCGTCCGGGATGCAA
                                                 F  N  F  T  I  P  K  T  T  P  G
 661 AGAGACTAACTCCAGAGGAACCTACCTAGTTCAACTTCACCATCCCCAAGACGACGCCGCCGGGCA
        K  Y  L  M  R  I  E  Q  F  M  P  S  T  V  E  Y  S  Q  W  Y  V  N
 727 AGTACCTGATGCGCATCGAGCAGTTCATGCCCTCCACGGTCGAATACAGCCAGTGGTACGTCAACT
        C  A  H  V  N  I  I  G  P  G  G  G  T  P  T  G  F  A  R  F  P  G
 793 GCGCCCACGTCAACATCATCGGCCCCGGCGGAGGCACGCCGACGGGCTTTGCCAGGTTTCCCGGCA
        T  Y  T  V  D  D  P
 859 CCTACACTGTTGACGATCCCGGTAAGCCGGACCTACCGGACACAGAGGCCTCGGGATAGCTTGCTA
                                                        G  I  K  V  P  L  N  Q  I  V
 925 ACCTTGTTTGCTCTCTCTCTTTTTCTCTCCCGACTAGGCATCAAGGTGCCGTTGAACCAGATCGTC
        N  S  G  E  L  P  Q  D  Q  L  R  L  L  E  Y  K  P  P  G  P  A  L
 991 AACAGCGGAGAGTTGCCGCAGGACCAACTGAGGCTGCTCGAGTACAAGCCCCCGGGCCCAGCGCTG
        W  T  G  *
1057 TGGACTGGTTGA
```

FIG. 15

POLYPEPTIDES HAVING CELLULOLYTIC ENHANCING ACTIVITY AND POLYNUCLEOTIDES ENCODING SAME

CROSS-REFERENCE TO RELATED APPLICATIONS

This application is a divisional of U.S. patent application Ser. No. 14/052,176, filed Oct. 11, 2013, now U.S. Pat. No. 8,865,445, which is a divisional of U.S. patent application Ser. No. 12/883,549, filed Sep. 16, 2010, now U.S. Pat. No. 8,569,581, which claims the benefit of U.S. Provisional Application No. 61/243,397, filed Sep. 17, 2009, U.S. Provisional Application No. 61/243,531, filed Sep. 18, 2009, U.S. Provisional Application No. 61/243,543, filed Sep. 18, 2009, and U.S. Provisional Application No. 61/243,679, filed Sep. 18, 2009. The contents of these applications are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

REFERENCE TO A DEPOSIT OF BIOLOGICAL MATERIAL

This application contains a reference to deposits of biological material, which deposits are incorporated herein by reference.

BACKGROUND OF THE INVENTION

Field of the Invention

The present invention relates to polypeptides having cellulolytic enhancing activity and polynucleotides encoding the polypeptides. The invention also relates to nucleic acid constructs, vectors, and host cells comprising the polynucleotides as well as methods of producing and using the polypeptides.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases.

Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

WO 2005/074647 discloses polypeptides having cellulolytic enhancing activity from *Thielavia terrestris*. WO 2005/074656 discloses polypeptides having cellulolytic enhancing activity from *Thermoascus aurantiacus*. WO 2007/089290 discloses polypeptides having cellulolytic enhancing activity from *Trichoderma reesei*. WO 2009/085935; WO 2009/085859; WO 2009/085864; and WO 2009/085868 disclose polypeptides having cellulolytic enhancing activity from *Myceliophthora thermophila*.

There is a need in the art for polypeptides having cellulolytic enhancing activity with improved properties for use in the degradation of cellulosic materials.

The present invention provides polypeptides having cellulolytic enhancing activity and polynucleotides encoding the polypeptides.

SUMMARY OF THE INVENTION

The present invention relates to isolated polypeptides having cellulolytic enhancing activity selected from the group consisting of:

(a) a polypeptide having at least 60% sequence identity to the mature polypeptide of SEQ ID NO: 2, SEQ ID NO: 6, or SEQ ID NO: 12; at least 65% sequence identity to the mature polypeptide of SEQ ID NO: 4; at least 70% sequence identity to the mature polypeptide SEQ ID NO: 18; at least 75% sequence identity to the mature polypeptide of SEQ ID NO: 10, SEQ ID NO: 16, or SEQ ID NO: 22; at least 80% sequence identity to the mature polypeptide of SEQ ID NO: 8; at least 85% sequence identity to the mature polypeptide of SEQ ID NO: 14; or at least 90% sequence identity to the mature polypeptide of SEQ ID NO: 20;

(b) a polypeptide encoded by a polynucleotide that hybridizes under medium-high, high, or very high stringency conditions with (i) the mature polypeptide coding sequence of SEQ ID NO: 1, SEQ ID NO: 3, SEQ ID NO: 5, SEQ ID NO: 11, or SEQ ID NO: 17, (ii) the cDNA sequence contained in the mature polypeptide coding sequence of SEQ ID NO: 1, SEQ ID NO: 3, SEQ ID NO: 5, SEQ ID NO: 11, or SEQ ID NO: 17, or (iii) the full-length complementary strand of (i) or (ii); high or very high stringency conditions with (i) the mature polypeptide coding sequence of SEQ ID NO: 7, SEQ ID NO: 9, SEQ ID NO: 13, SEQ ID NO: 15, or SEQ ID NO: 21, (ii) the cDNA sequence contained in the mature polypeptide coding sequence of SEQ ID NO: 7, SEQ ID NO: 9, SEQ ID NO: 13, SEQ ID NO: 15, or SEQ ID NO: 21, or (iii) the full-length complementary strand of (i) or (ii); or very high stringency conditions with (i) the mature polypeptide coding sequence of SEQ ID NO: 19, (ii) the cDNA sequence contained in the mature polypeptide coding sequence of SEQ ID NO: 19, or (iii) the full-length complementary strand of (i) or (ii);

(c) a polypeptide encoded by a polynucleotide having at least 60% sequence identity to the mature polypeptide coding sequence of SEQ ID NO: 1, SEQ ID NO: 5, or SEQ ID NO: 11; at least 65% sequence identity to the mature polypeptide coding sequence of SEQ ID NO: 3; at least 70% sequence identity to the mature polypeptide coding sequence of SEQ ID NO: 17; at least 75% sequence identity to the mature polypeptide coding sequence of SEQ ID NO: 9, SEQ ID NO: 15, or SEQ ID NO: 21; at least 80% sequence identity to the mature polypeptide coding sequence of SEQ ID NO: 7; at least 85% sequence identity to the mature polypeptide coding sequence of SEQ ID NO: 13; or at least 90% sequence identity to the mature polypeptide coding sequence of SEQ ID NO: 19; or the cDNA sequences thereof;

(d) a variant comprising a substitution, deletion, and/or insertion of one or more (several) amino acids of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22; and (e) a fragment of the polypeptide of (a), (b), (c), or (d) that has cellulolytic enhancing activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to methods for degrading or converting a cellulosic material, comprising: treating the cellulosic material with an enzyme composition in the presence of a polypeptide having cellulolytic enhancing activity of the present invention.

The present invention also relates to methods of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (several) fermenting microorganisms to produce the fermentation product; and (c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with an enzyme composition in the presence of a polypeptide having cellulolytic enhancing activity of the present invention.

The present invention also relates to a polynucleotide encoding a signal peptide comprising or consisting of amino acids 1 to 17 of SEQ ID NO: 2, amino acids 1 to 19 of SEQ ID NO: 4, amino acids 1 to 17 of SEQ ID NO: 6, amino acids 1 to 19 of SEQ ID NO: 8, amino acids 1 to 21 of SEQ ID NO: 10, amino acids 1 to 24 of SEQ ID NO: 12, amino acids 1 to 16 of SEQ ID NO: 14, amino acids 1 to 18 of SEQ ID NO: 16, amino acids 1 to 22 of SEQ ID NO: 18, amino acids 1 to 16 of SEQ ID NO: 20, or amino acids 1 to 19 of SEQ ID NO: 22, which is operably linked to a gene encoding a protein; nucleic acid constructs, expression vectors, and recombinant host cells comprising the polynucleotides; and methods of producing a protein.

BRIEF DESCRIPTION OF THE FIGURES

FIG. 1 shows the genomic DNA sequence without introns and the deduced amino acid sequence of a gene encoding a *Thielavia terrestris* NRRL 8126 GH61J polypeptide having cellulolytic enhancing activity. The full-length genomic DNA sequence with introns is shown in SEQ ID NO: 1 and the deduced amino acid sequence is shown in SEQ ID NO: 2.

FIG. 2 shows the genomic DNA sequence without introns and the deduced amino acid sequence of a gene encoding a *Thielavia terrestris* NRRL 8126 GH61K polypeptide having cellulolytic enhancing activity. The full-length genomic DNA sequence with introns is shown in SEQ ID NO: 3 and the deduced amino acid sequence is shown in SEQ ID NO: 4.

FIG. 3 shows the genomic DNA sequence without introns and the deduced amino acid sequence of a gene encoding a *Thielavia terrestris* NRRL 8126 GH61L polypeptide having cellulolytic enhancing activity. The full-length genomic DNA sequence with introns is shown in SEQ ID NO: 5 and the deduced amino acid sequence is shown in SEQ ID NO: 6.

FIG. 6 shows the genomic DNA sequence and the deduced amino acid sequence of a gene encoding a *Thielavia terrestris* NRRL 8126 GH61M polypeptide having cellulolytic enhancing activity (SEQ ID NOs: 7 and 8, respectively).

FIG. 8 shows the genomic DNA sequence and the deduced amino acid sequence of a gene encoding a *Thielavia terrestris* NRRL 8126 GH61N polypeptide having cellulolytic enhancing activity (SEQ ID NOs: 9 and 10, respectively).

FIG. 10 shows the genomic DNA sequence and the deduced amino acid sequence of a gene encoding a *Thielavia terrestris* NRRL 8126 GH61O polypeptide having cellulolytic enhancing activity (SEQ ID NOs: 11 and 12, respectively).

FIG. 11 shows the genomic DNA sequence and the deduced amino acid sequence of a gene encoding a *Thielavia terrestris* NRRL 8126 GH61P polypeptide having cellulolytic enhancing activity (SEQ ID NOs: 13 and 14, respectively).

FIG. 12 shows the genomic DNA sequence and the deduced amino acid sequence of a gene encoding a *Thielavia terrestris* NRRL 8126 GH61R polypeptide having cellulolytic enhancing activity (SEQ ID NOs: 15 and 16, respectively).

FIG. 13 shows the genomic DNA sequence and the deduced amino acid sequence of a gene encoding a *Thielavia terrestris* NRRL 8126 GH61S polypeptide having cellulolytic enhancing activity (SEQ ID NOs: 17 and 18, respectively).

FIG. 14 shows the genomic DNA sequence and the deduced amino acid sequence of a gene encoding a *Thielavia terrestris* NRRL 8126 GH61T polypeptide having cellulolytic enhancing activity (SEQ ID NOs: 19 and 20, respectively).

FIG. 15 shows the genomic DNA sequence and the deduced amino acid sequence of a gene encoding a *Thielavia terrestris* NRRL 8126 GH61U polypeptide having cellulolytic enhancing activity (SEQ ID NOs: 21 and 22, respectively).

DEFINITIONS

Figure 4:
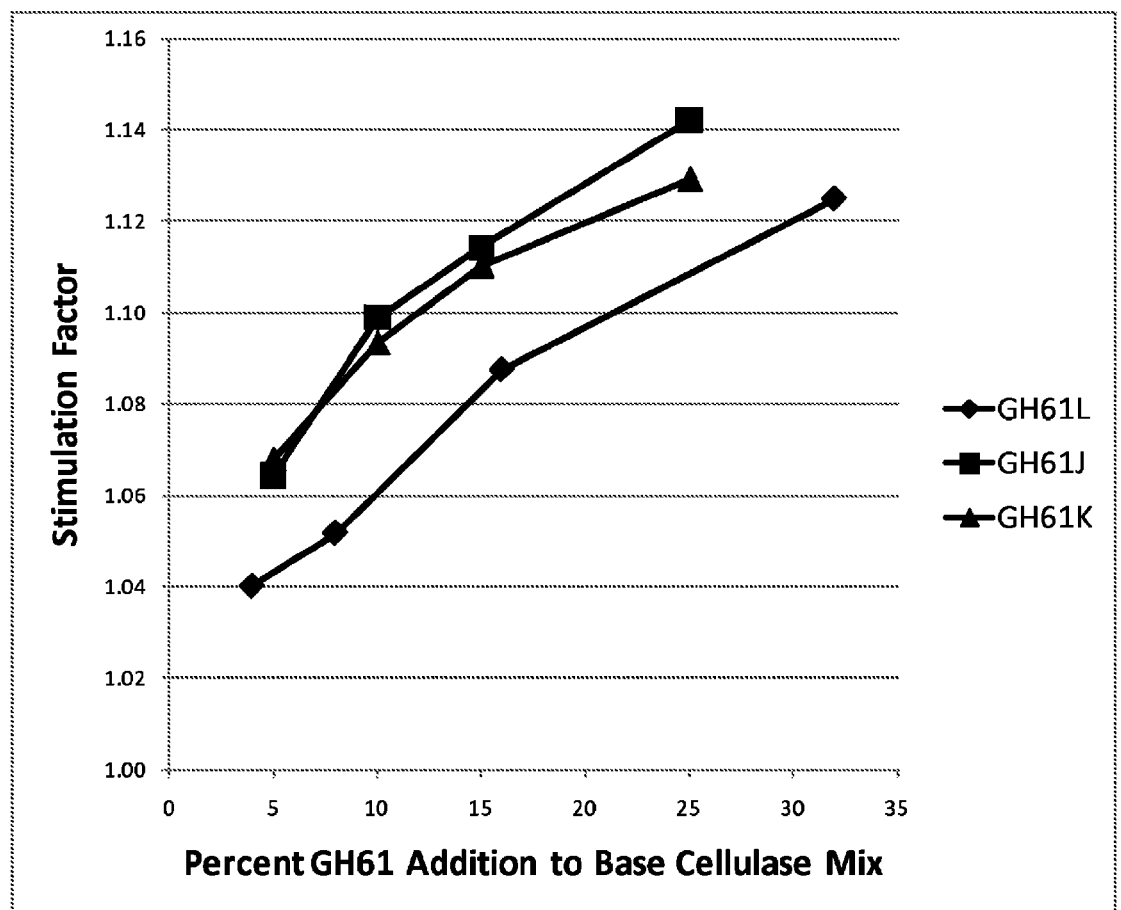
FIG. 4 shows hydrolysis of pretreated corn stover (PCS) with a *Trichoderma reesei* cellulase mixture in the presence of varying concentrations of *Thielavia terrestris* NRRL 8126 GH61J, GH61K, and GH61L polypeptides having cellulolytic enhancing activity.

Polypeptide Having Cellulolytic Enhancing Activity:

The term "polypeptide having cellulolytic enhancing activity" means a GH61 polypeptide that enhances the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at 50° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

The polypeptides of the present invention have at least 20%, e.g., at least 40%, at least 50%, at least 60%, at least 70%, at least 80%, at least 90%, at least 95%, and at least 100% of the cellulolytic enhancing activity of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

Family 61 Glycoside Hydrolase:

The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Cellulolytic Enzyme or Cellulase:

The term "cellulolytic enzyme" or "cellulase" means one or more (several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-20 mg of cellulolytic enzyme protein/g of cellulose in PCS for 3-7 days at 50° C. compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 72 hours, sugar analysis by AMINEX® HPX-87H column (Bio-Rad Laboratories, Inc., Hercules, Calif., USA).

Endoglucanase:

The term "endoglucanase" means an endo-1,4-(1,3;1,4)-beta-D-glucan 4-glucanohydrolase (E.C. 3.2.1.4), which catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Cellobiohydrolase:

The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present invention, cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Lever et al. method can be employed to assess hydrolysis of cellulose in corn stover, while the methods of van Tilbeurgh et al. and Tomme et al. can be used to determine the cellobiohydrolase activity on a fluorescent disaccharide derivative, 4-methylumbelliferyl-β-D-lactoside.

Beta-Glucosidase:

The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from *Chaetomium thermo-*

*philum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Hemicellulolytic Enzyme or Hemicellulase:

The term "hemicellulolytic enzyme" or "hemicellulase" means one or more (several) enzymes that hydrolyze a hemicellulosic material. See, for example, Shallom, D. and Shoham, Y. Microbial hemicellulases. *Current Opinion In Microbiology,* 2003, 6 (3): 219-228). Hemicellulases are key components in the degradation of plant biomass. Examples of hemicellulases include, but are not limited to, an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families marked by numbers. Some families, with overall similar fold, can be further grouped into clans, marked alphabetically (e.g., GH-A). A most informative and updated classification of these and other carbohydrate active enzymes is available on the Carbohydrate-Active Enzymes (CAZy) database. Hemicellulolytic enzyme activities can be measured according to Ghose and Bisaria, 1987, *Pure & Appl. Chem.* 59: 1739-1752.

Xylan Degrading Activity or Xylanolytic Activity:

The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum* commune, *FEBS Letters* 580 (19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23 (3): 257-270. Xylanase activity can also be determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase:

The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

Beta-Xylosidase:

The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

Acetylxylan Esterase:

The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20. One unit of acetylxylan esterase is defined as the amount of enzyme capable of releasing 1 μmole of p-nitrophenolate anion per minute at pH 5, 25° C.

Feruloyl Esterase:

The term "feruloyl esterase" means a 4-hydroxy-3-methoxycinnamoyl-sugar hydrolase (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0.

One unit of feruloyl esterase equals the amount of enzyme capable of releasing 1 μmole of p-nitrophenolate anion per minute at pH 5, 25° C.

Alpha-Glucuronidase:

The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Alpha-L-Arabinofuranosidase:

The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Cellulosic Material:

The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is lignocellulose, which comprises cellulose, hemicellulose, and lignin.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

The cellulosic material may be used as is or may be subjected to pretreatment, using conventional methods known in the art, as described herein. In a preferred aspect, the cellulosic material is pretreated.

Pretreated Corn Stover:

The term "PCS" or "Pretreated Corn Stover" means a cellulosic material derived from corn stover by treatment with heat and dilute sulfuric acid.

Xylan-Containing Material:

The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono) arabinoxylans, arabinoxylans, and complex heteroxylans. See, for example, Ebringerova et al., 2005, *Adv. Polym. Sci.* 186: 1-67.

In the methods of the present invention, any material containing xylan may be used. In a preferred aspect, the xylan-containing material is lignocellulose.

Isolated or Purified:

The term "isolated" or "purified" means a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, or at least 95% pure, as determined by SDS-PAGE, and a polynucleotide may be at least 1% pure, e.g., at least 5% pure, at least 10% pure, at least 20% pure, at least 40% pure, at least 60% pure, at least 80% pure, at least 90% pure, or at least 95% pure, as determined by agarose electrophoresis.

Mature Polypeptide:

The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 18 to 246 of SEQ ID NO: 2 based on the SignalP program (Nielsen et al., 1997, *Protein Engineering* 10:1-6) that predicts amino acids 1 to 17 of SEQ ID NO: 2 are a signal peptide. In another aspect, the mature polypeptide is amino acids 20 to 334 of SEQ ID NO: 4 based on the SignalP program that predicts amino acids 1 to 19 of SEQ ID NO: 4 are a signal peptide. In another aspect, the mature polypeptide is amino acids 18 to 227 of SEQ ID NO: 6 based on the SignalP program that predicts amino acids 1 to 17 of SEQ ID NO: 6 are a signal peptide. In another aspect, the mature polypeptide is amino acids 20 to 223 of SEQ ID NO: 8 based on the SignalP program that predicts amino acids 1 to 19 of SEQ ID NO: 8 are a signal peptide. In another aspect, the mature polypeptide is amino acids 22 to 368 of SEQ ID NO: 10 based on the SignalP program that predicts amino acids 1 to 21 of SEQ ID NO: 10 are a signal peptide. In another aspect, the mature polypeptide is amino acids 25 to 330 of SEQ ID NO: 12 based on the SignalP program that predicts amino acids 1 to 24 of SEQ ID NO: 12 are a signal peptide. In another aspect, the mature polypeptide is amino acids 17 to 236 of SEQ ID NO: 14 based on the SignalP program that predicts amino acids 1 to 16 of SEQ ID NO: 14 are a signal peptide. In another aspect, the mature polypeptide is amino acids 19 to 250 of SEQ ID NO: 16 based on the SignalP program that predicts amino acids 1 to 18 of SEQ ID NO: 16 are a signal peptide. In another aspect, the mature polypeptide is amino acids 23 to 478 of SEQ ID NO: 18 based on the SignalP program that predicts amino acids 1 to 22 of SEQ ID NO: 18 are a signal peptide. In another aspect, the mature polypeptide is amino acids 17 to 230 of SEQ ID NO: 20 based on the SignalP program that predicts amino acids 1 to 16 of SEQ ID NO: 20 are a signal peptide. In another aspect, the mature polypeptide is amino acids 20 to 257 of SEQ ID NO: 22 based on the SignalP program that predicts amino acids 1 to 19 of SEQ ID NO: 22 are a signal peptide. It is known in the art that a host cell may produce a mixture of two of more different mature polypeptides (i.e., with a different C-terminal and/or N-terminal amino acid) expressed by the same polynucleotide.

Mature Polypeptide Coding Sequence:

The term "mature polypeptide coding sequence" means a polynucleotide that encodes a mature polypeptide having cellulolytic enhancing activity. In one aspect, the mature polypeptide coding sequence is nucleotides 52 to 875 of SEQ ID NO: 1 based on the SignalP program (Nielsen et al., 1997, supra) that predicts nucleotides 1 to 51 of SEQ ID NO: 1 encode a signal peptide. In another aspect, the mature polypeptide coding sequence is the cDNA sequence contained in nucleotides 52 to 875 of SEQ ID NO: 1. In another aspect, the mature polypeptide coding sequence is nucleotides 58 to 1250 of SEQ ID NO: 3 based on the SignalP program that predicts nucleotides 1 to 57 of SEQ ID NO: 3 encode a signal peptide. In another aspect, the mature polypeptide coding sequence is the cDNA sequence contained in nucleotides 58 to 1250 of SEQ ID NO: 3. In another aspect, the mature polypeptide coding sequence is nucleotides 52 to 795 of SEQ ID NO: 5 based on the SignalP program that predicts nucleotides 1 to 51 of SEQ ID NO: 5 encode a signal peptide. In another aspect, the mature polypeptide coding sequence is the cDNA sequence contained in nucleotides 52 to 795 of SEQ ID NO: 5. In another aspect, the mature polypeptide coding sequence is nucleotides 58 to 974 of SEQ ID NO: 7 based on the SignalP program that predicts nucleotides 1 to 57 of SEQ ID NO: 7 encode a signal peptide. In another aspect, the mature polypeptide coding sequence is the cDNA sequence contained in nucleotides 58 to 974 of SEQ ID NO: 7. In another aspect, the mature polypeptide coding sequence is nucleotides 64 to 1104 of SEQ ID NO: 9 based on the SignalP program that predicts nucleotides 1 to 63 of SEQ ID NO: 9 encode a signal peptide. In another aspect, the mature polypeptide coding sequence is the cDNA sequence contained in nucleotides 64 to 1104 of SEQ ID NO: 9. In another aspect, the mature polypeptide coding sequence is nucleotides 73 to 990 of SEQ ID NO: 11 based on the SignalP program that predicts nucleotides 1 to 72 of SEQ ID NO: 11 encode a signal peptide. In another aspect, the mature polypeptide coding sequence is the cDNA sequence contained in nucleotides 73 to 990 of SEQ ID NO: 11. In another aspect, the mature polypeptide coding sequence is nucleotides 49 to 1218 of SEQ ID NO: 13 based on the SignalP program that predicts nucleotides 1 to 48 of SEQ ID NO: 13 encode a signal peptide. In another aspect, the mature polypeptide coding sequence is the cDNA sequence contained in nucleotides 49 to 1218 of SEQ ID NO: 13. In another aspect, the mature polypeptide coding sequence is nucleotides 55 to 930 of SEQ ID NO: 15 based on the SignalP program that predicts nucleotides 1 to 54 of SEQ ID NO: 15 encode a signal peptide. In another aspect, the mature polypeptide coding sequence is the cDNA sequence contained in nucleotides 55 to 930 of SEQ ID NO: 15. In another aspect, the mature polypeptide coding sequence is nucleotides 67 to 1581 of SEQ ID NO: 17 based on the SignalP program that predicts nucleotides 1 to 66 of SEQ ID NO: 17 encode a signal peptide. In another aspect, the mature polypeptide coding sequence is the cDNA sequence contained in nucleotides 67 to 1581 of SEQ ID NO: 17. In another aspect, the mature polypeptide coding sequence is nucleotides 49 to 865 of SEQ ID NO: 19 based on the SignalP program that predicts nucleotides 1 to 48 of SEQ ID NO: 19 encode a signal peptide. In another aspect, the mature polypeptide coding sequence is the cDNA sequence contained in nucleotides 49 to 865 of SEQ ID NO: 19. In another aspect, the mature polypeptide coding sequence is nucleotides 58 to 1065 of SEQ ID NO: 21 based on the SignalP program that predicts nucleotides 1 to 57 of SEQ ID NO: 21 encode a signal peptide. In another aspect, the mature polypeptide coding sequence is the cDNA sequence contained in nucleotides 58 to 1065 of SEQ ID NO: 21.

Sequence Identity:

The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Fragment:

The term "fragment" means a polypeptide having one or more (several) amino acids deleted from the amino and/or carboxyl terminus of a mature polypeptide; wherein the fragment has cellulolytic enhancing activity. In a one aspect, a fragment contains at least 190 amino acid residues, e.g., at least 200 amino acid residues or at least 210 amino acid residues of the mature polypeptide of SEQ ID NO: 2. In another aspect, a fragment contains at least 265 amino acid residues, e.g., at least 280 amino acid residues or at least 295 amino acid residues of the mature polypeptide of SEQ ID NO: 4. In another aspect, a fragment contains at least 180 amino acid residues, e.g., at least 190 amino acid residues or at least 200 amino acid residues of the mature polypeptide of SEQ ID NO: 6. In another aspect, a fragment contains at least 170 amino acid residues, e.g., at least 180 amino acid residues or at least 190 amino acid residues, of the mature polypeptide of SEQ ID NO: 8. In another aspect, a fragment contains at least 305 amino acid residues, e.g., at least 330 amino acid residues or at least 335 amino acid residues of the mature polypeptide of SEQ ID NO: 10. In another aspect, a fragment contains at least 255 amino acid residues, e.g., at least 270 amino acid residues or at least 285 amino acid residues of the mature polypeptide of SEQ ID NO: 12. In another aspect, a fragment contains at least 190 amino acid residues, e.g., at least 200 amino acid residues or at least 210 amino acid residues of the mature polypeptide of SEQ ID NO: 14. In another aspect, a fragment contains at least 200 amino acid residues, e.g., at least 210 amino acid residues or at least 220 amino acid residues of the mature polypeptide of SEQ ID NO: 16. In another aspect, a fragment contains at least 390 amino acid residues, e.g., at least 410 amino acid residues or at least 430 amino acid residues of the mature polypeptide of SEQ ID NO: 18. In another aspect, a fragment contains at least 180 amino acid residues, e.g., at least 190 amino acid residues or at least 200 amino acid residues of the mature polypeptide of SEQ ID NO: 20. In another aspect, a fragment contains at least 210 amino acid residues, e.g., at least 220 amino acid residues or at least 230 amino acid residues of the mature polypeptide of SEQ ID NO: 22.

Subsequence:

The term "subsequence" means a polynucleotide having one or more (several) nucleotides deleted from the 5' and/or 3' end of a mature polypeptide coding sequence; wherein the subsequence encodes a fragment having cellulolytic enhancing activity. In one aspect, a subsequence contains at least 570 nucleotides, e.g., at least 600 nucleotides or at least 630 nucleotides of the mature polypeptide coding sequence of SEQ ID NO: 1. In another preferred aspect, a subsequence contains at least 795 nucleotides, e.g., at least 840 nucleotides or at least 885 nucleotides of the mature polypeptide coding sequence of SEQ ID NO: 3. In another preferred aspect, a subsequence contains at least 540 nucleotides, e.g., at least 570 nucleotides or at least 600 nucleotides of the mature polypeptide coding sequence of SEQ ID NO: 5. In a preferred aspect, a subsequence contains at least 510 nucleotides, e.g., at least 540 nucleotides or at least 570 nucleotides of the mature polypeptide coding sequence of SEQ ID NO: 7. In another aspect, a subsequence contains at least 915 nucleotides, e.g., at least 960 nucleotides or at least 1005 nucleotides of the mature polypeptide coding sequence of SEQ ID NO: 9. In another preferred aspect, a subsequence contains at least 765 nucleotides, e.g., at least 810 nucleotides or at least 855 nucleotides of the mature polypeptide coding sequence of SEQ ID NO: 11. In another preferred aspect, a subsequence contains at least 570 nucleotides, e.g., at least 600 nucleotides or at least 630 nucleotides of the mature polypeptide coding sequence of SEQ ID NO: 13. In another preferred aspect, a subsequence contains at least 600 nucleotides, e.g., at least 630 nucleotides or at least 660 nucleotides of the mature polypeptide coding sequence of SEQ ID NO: 15. In another preferred aspect, a subsequence contains at least 1170 nucleotides, e.g., at least 1230 nucleotides or at least 1290 nucleotides of the mature polypeptide coding sequence of SEQ ID NO: 17. In another preferred aspect, a subsequence contains at least 540 nucleotides, e.g., at least 570 nucleotides or at least 600 nucleotides of the mature polypeptide coding sequence of SEQ ID NO: 19. In another preferred aspect, a subsequence contains at least 630 nucleotides, e.g., at least 660 nucleotides or at least 690 nucleotides of the mature polypeptide coding sequence of SEQ ID NO: 21.

Allelic Variant:

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding Sequence:

The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA:

The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic Acid Construct:

The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control Sequences:

The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably Linked:

The term "operably linked" means a configuration in which a control sequence is placed at an appropriate position relative to the coding sequence of a polynucleotide such that the control sequence directs the expression of the coding sequence.

Expression:

The term "expression" includes any step involved in the production of the polypeptide including, but not limited to, transcription, post-transcriptional modification, translation, post-translational modification, and secretion.

Expression Vector:

The term "expression vector" means a linear or circular DNA molecule that comprises a polynucleotide encoding a polypeptide and is operably linked to additional nucleotides that provide for its expression.

Host Cell:

The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Variant:

The term "variant" means a polypeptide having cellulolytic enhancing activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding one or more (several) amino acids, e.g., 1-5 amino acids, adjacent to an amino acid occupying a position.

DETAILED DESCRIPTION OF THE INVENTION

Polypeptides Having Cellulolytic Enhancing Activity

The present invention relates to isolated polypeptides having cellulolytic enhancing activity selected from the group consisting of:

(a) a polypeptide having at least 60% sequence identity to the mature polypeptide of SEQ ID NO: 2, SEQ ID NO: 6, or SEQ ID NO: 12; at least 65% sequence identity to the mature polypeptide of SEQ ID NO: 4; at least 70% sequence identity to the mature polypeptide of SEQ ID NO: 18; at least 75% sequence identity to the mature polypeptide of SEQ ID NO: 10, SEQ ID NO: 16, or SEQ ID NO: 22; at least 80% sequence identity to the mature polypeptide of SEQ ID NO: 8; at least 85% sequence identity to the mature polypeptide of SEQ ID NO: 14; or at least 90% sequence identity to the mature polypeptide of SEQ ID NO: 20;

(b) a polypeptide encoded by a polynucleotide that hybridizes under medium-high, high, or very high stringency conditions with (i) the mature polypeptide coding sequence of SEQ ID NO: 1, SEQ ID NO: 3, SEQ ID NO: 5, SEQ ID NO: 11, or SEQ ID NO: 17, (ii) the cDNA sequence contained in the mature polypeptide coding sequence of SEQ ID NO: 1, SEQ ID NO: 3, SEQ ID NO: 5, SEQ ID NO: 11, or SEQ ID NO: 17, or (iii) the full-length complementary strand of (i) or (ii); high or very high stringency conditions with (i) the mature polypeptide coding sequence of SEQ ID NO: 7, SEQ ID NO: 9, SEQ ID NO: 13, SEQ ID NO: 15, or SEQ ID NO: 21, (ii) the cDNA sequence contained in the mature polypeptide coding sequence of SEQ ID NO: 7, SEQ ID NO: 9, SEQ ID NO: 13, SEQ ID NO: 15, or SEQ ID NO: 21, or (iii) the full-length complementary strand of (i) or (ii); or very high stringency conditions with (i) the mature polypeptide coding sequence of SEQ ID NO: 19, (ii) the cDNA sequence contained in the mature polypeptide coding sequence of SEQ ID NO: 19, or (iii) the full-length complementary strand of (i) or (ii);

(c) a polypeptide encoded by a polynucleotide having at least 60% sequence identity to the mature polypeptide coding sequence of SEQ ID NO: 1, SEQ ID NO: 5, or SEQ ID NO: 11; at least 65% sequence identity to the mature polypeptide coding sequence of SEQ ID NO: 3; at least 70% sequence identity to the mature polypeptide coding sequence of SEQ ID NO: 17; at least 75% sequence identity to the mature polypeptide coding sequence of SEQ ID NO: 9, SEQ ID NO: 15, or SEQ ID NO: 21; at least 80% sequence identity to the mature polypeptide coding sequence of SEQ ID NO: 7; at least 85% sequence identity to the mature polypeptide coding sequence of SEQ ID NO: 13; or at least 90% sequence identity to the mature polypeptide coding sequence of SEQ ID NO: 19; or the cDNA sequences thereof;

(d) a variant comprising a substitution, deletion, and/or insertion of one or more (several) amino acids of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22; and (e) a fragment of a polypeptide of (a), (b), (c), or (d) that has cellulolytic enhancing activity.

The present invention relates to isolated polypeptides having a sequence identity to the mature polypeptide of SEQ ID NO: 2, SEQ ID NO: 6, or SEQ ID NO: 12 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 4 of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 18 of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 10, SEQ ID NO: 16, or SEQ ID NO: 22 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 8 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 14 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide of SEQ ID NO: 20 at least 90%, e.g., at least 91%, at least 92%, at least 93%, at least 94%, at least 95%, at least 96%, at least 97%, at least 98%, at least 99%, or 100%, which have cellulolytic enhancing activity.

In one aspect, the polypeptides differ by no more than ten amino acids, e.g., by five amino acids, by four amino acids, by three amino acids, by two amino acids, and by one amino acid from the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

A polypeptide of the present invention preferably comprises or consists of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22 or an allelic variant thereof; or is a fragment thereof having cellulolytic enhancing activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22. In another preferred aspect, the polypeptide comprises or consists of amino acids 18 to 246 of SEQ ID NO: 2. In another preferred aspect, the polypeptide comprises or consists of amino acids 20 to 334 of SEQ ID NO: 4. In another preferred aspect, the polypeptide comprises or consists of amino acids 18 to 227 of SEQ ID NO: 6. In another preferred aspect, the polypeptide comprises or consists of amino acids 20 to 223 of SEQ ID NO: 8. In another preferred aspect, the polypeptide comprises or consists of amino acids 22 to 368 of SEQ ID NO: 10. In another preferred aspect, the polypeptide comprises or consists of amino acids 25 to 330 of SEQ ID NO: 12. In another preferred aspect, the polypeptide comprises or consists of amino acids 17 to 236 of SEQ ID NO: 14. In another preferred aspect, the polypeptide comprises or consists of amino acids 19 to 250 of SEQ ID NO: 16. In another preferred aspect, the polypeptide comprises or consists of amino acids 23 to 478 of SEQ ID NO: 18. In another preferred aspect, the polypeptide comprises or consists of amino acids 17 to 230 of SEQ ID NO: 20. In another preferred aspect, the polypeptide comprises or consists of amino acids 20 to 257 of SEQ ID NO: 22.

The present invention also relates to isolated polypeptides having cellulolytic enhancing activity that are encoded by polynucleotides that hybridize under medium-high, high, or very high stringency conditions with (i) the mature polypeptide coding sequence of SEQ ID NO: 1, SEQ ID NO: 3, SEQ ID NO: 5, SEQ ID NO: 11, or SEQ ID NO: 17, (ii) the cDNA sequence contained in the mature polypeptide coding sequence of SEQ ID NO: 1, SEQ ID NO: 3, SEQ ID NO: 5, SEQ ID NO: 11, or SEQ ID NO: 17, or (iii) the full-length complementary strand of (i) or (ii); high or very high stringency conditions with (i) the mature polypeptide coding sequence of SEQ ID NO: 7, SEQ ID NO: 9, SEQ ID NO: 13, SEQ ID NO: 15, or SEQ ID NO: 21, (ii) the cDNA sequence contained in the mature polypeptide coding sequence of SEQ ID NO: 7, SEQ ID NO: 9, SEQ ID NO: 13, SEQ ID NO: 15, or SEQ ID NO: 21, or (iii) the full-length complementary strand of (i) or (ii); or very high stringency conditions with (i) the mature polypeptide coding sequence of SEQ ID NO: 19, (ii) the cDNA sequence contained in the mature polypeptide coding sequence of SEQ ID NO: 19, or (iii) the full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, or a subsequence thereof, as well as the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, or a fragment thereof, may be used to design nucleic acid probes to identify and clone DNA encoding polypeptides having cellulolytic enhancing activity from strains of different genera or species according to methods well known in the art. In particular, such probes can be used for hybridization with the genomic DNA or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having cellulolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, or a subsequence thereof, the carrier material is preferably used in a Southern blot.

For purposes of the present invention, hybridization indicates that the polynucleotide hybridizes to a labeled nucleic acid probe corresponding to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21; the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21; the cDNA sequence contained in the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21; the full-length complementary strands thereof; or a subsequence thereof; under very low to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, or the cDNA sequences thereof. In another aspect, the nucleic acid probe is nucleotides 52 to 875 of SEQ ID NO: 1, nucleotides 58 to 1250 of SEQ ID NO: 3, nucleotides 52 to 795 of SEQ ID NO: 5, nucleotides 58 to 974 of SEQ ID NO: 7, nucleotides 64 to 1104 of SEQ ID NO: 9, nucleotides 73 to 990 of SEQ ID NO: 11, nucleotides 49 to 1218 of SEQ ID NO: 13, nucleotides 55 to 930 of SEQ ID NO: 15, nucleotides 67 to 1581 of SEQ ID NO: 17, nucleotides 49 to 865 of SEQ ID NO: 19, or nucleotides 58 to 1065 of SEQ ID NO: 21. In another aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, or the mature polypeptides thereof; or fragments thereof. In another preferred aspect, the nucleic acid probe is SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, or the cDNA sequences thereof. In another aspect, the nucleic acid probe is the polynucleotide sequence contained in plasmid pSMai216 which is contained in E. coli NRRL B-50301, wherein the polynucleotide sequence thereof encodes a polypeptide having cellulolytic enhancing activity. In another aspect, the nucleic acid probe is the mature polypeptide coding region contained in plasmid pSMai21 which is contained in E. coli NRRL B-50301. In another aspect, the nucleic acid probe is the polynucleotide sequence contained in plasmid pSMAi217 which is contained in E. coli NRRL B-50302, wherein the polynucleotide sequence thereof encodes a polypeptide having cellulolytic enhancing activity. In another aspect, the nucleic acid probe is the mature polypeptide coding region contained in plasmid pSMai217 which is contained in E. coli NRRL B-50302. In another aspect, the nucleic acid probe is the polynucleotide sequence contained in plasmid pSMai218 which is contained in E. coli NRRL B-50303, wherein the polynucleotide sequence thereof encodes a polypeptide having cellulolytic enhancing activity. In another aspect, the nucleic acid probe is the mature polypeptide coding region contained in plasmid pSMai218 which is contained in E. coli NRRL B-50303. In another aspect, the nucleic acid probe is the polynucleotide sequence contained in plasmid pSMai213 which is contained in E. coli NRRL B-50300, wherein the polynucleotide sequence thereof encodes a polypeptide having cellulolytic enhancing activity. In another aspect, the nucleic acid probe is the mature polypeptide coding region contained in plasmid pSMai213 which is contained in E. coli NRRL B-50300. In another aspect, the nucleic acid probe is the polynucleotide sequence contained in plasmid pAG68 which is contained in E. coli NRRL B-50320, wherein the polynucleotide sequence thereof encodes a polypeptide having cellulolytic enhancing activity. In another aspect, the nucleic acid probe is the mature polypeptide coding region contained in plasmid pAG68 which is contained in E. coli NRRL B-50320. In another aspect, the nucleic acid probe is the polynucleotide sequence contained in plasmid pAG69 which is contained in E. coli NRRL B-50321, wherein the polynucleotide sequence thereof encodes a polypeptide having cellulolytic enhancing activity. In another aspect, the nucleic acid probe is the mature polypeptide coding region contained in plasmid pAG69 which is contained in E. coli NRRL B-50321. In another aspect, the nucleic acid probe is the polynucleotide sequence contained in plasmid pAG75 which is contained in E. coli NRRL B-50322, wherein the polynucleotide sequence thereof encodes a polypeptide having cellulolytic enhancing activity. In another aspect, the nucleic acid probe is the mature polypeptide coding region contained in plasmid pAG75 which is contained in E. coli NRRL B-50322. In another aspect, the nucleic acid probe is the polynucleotide sequence contained in plasmid pAG76 which is contained in E. coli NRRL B-50323, wherein the polynucleotide sequence thereof encodes a polypeptide having cellulolytic enhancing activity. In another aspect, the nucleic acid probe is the mature polypeptide coding region contained in plasmid pAG76 which is contained in E. coli NRRL B-50323. In another aspect, the nucleic acid probe is the polynucleotide sequence contained in plasmid pAG77 which is contained in E. coli NRRL B-50324, wherein the polynucleotide sequence thereof encodes a polypeptide having cellulolytic enhancing activity. In another aspect, the nucleic acid probe is the mature polypeptide coding region contained in plasmid pAG77 which is contained in E. coli NRRL B-50324. In another aspect, the nucleic acid probe is the polynucleotide sequence contained in plasmid pAG78 which is contained in E. coli NRRL B-50325, wherein the polynucleotide sequence thereof encodes a polypeptide having cellulolytic enhancing activity. In another aspect, the nucleic acid probe is the mature polypeptide coding region contained in plasmid pAG78 which is contained in E. coli NRRL B-50325. In another aspect, the nucleic acid probe is the polynucleotide sequence contained in plasmid pAG79 which is contained in E. coli NRRL B-50326, wherein the polynucleotide sequence thereof encodes a polypeptide having cellulolytic enhancing activity. In another aspect, the nucleic acid probe is the mature polypeptide coding region contained in plasmid pAG79 which is contained in E. coli NRRL B-50326.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, Proc. Natl. Acad. Sci.

*USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention also relates to isolated polypeptides having cellulolytic enhancing activity encoded by polynucleotides having a sequence identity to the mature polypeptide coding sequence of SEQ ID NO: 1, SEQ ID NO: 5, or SEQ ID NO: 11 of at least 60%, at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 3 of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 17 of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 9, SEQ ID NO: 15, or SEQ ID NO: 21 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 7 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 13 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide of SEQ ID NO: 19 at least 90%, e.g., at least 91%, at least 92%, at least 93%, at least 94%, at least 95%, at least 96%, at least 97%, at least 98%, at least 99%, or 100%.

The present invention also relates to variants comprising a substitution, deletion, and/or insertion of one or more (or several) amino acids of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, or homologous sequences thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellulolytic enhancing activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22 is not more than 10, e.g., 1, 2, 3, 4, 5, 6, 7, 8 or 9.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Cellulolytic Enhancing Activity

A polypeptide having cellulolytic enhancing activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* polypeptide having cellulolytic enhancing activity, or a gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* polypeptide.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide.

In another aspect, the polypeptide is a *Streptococcus equisimilis, Streptococcus pyogenes, Streptococcus uberis,* or *Streptococcus equi* subsp. *Zooepidemicus* polypeptide.

In another aspect, the polypeptide is a *Streptomyces achromogenes, Streptomyces avermitilis, Streptomyces coelicolor, Streptomyces griseus,* or *Streptomyces lividans* polypeptide.

The polypeptide may be a fungal polypeptide. For example, the polypeptide may be a yeast polypeptide such as a *Candida, Kluyveromyces, Pichia, Saccharomyces, Schizosaccharomyces,* or *Yarrowia* polypeptide; or a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide.

In another aspect, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Trichoderma harzianum, Trichoderma koningii, Trichoderma longibrachiatum, Trichoderma reesei,* or *Trichoderma viride* polypeptide.

In another aspect, the polypeptide is a *Thielavia terrestris* polypeptide having cellulolytic enhancing activity. In another aspect, the polypeptide is a *Thielavia terrestris* NRRL 8126 polypeptide having cellulolytic enhancing activity, e.g., the polypeptide comprising the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Thielavia terrestris*, or a related organism and thus, for example, may be an allelic or species variant of the polypeptide encoding region of the polynucleotide.

The present invention also relates to isolated polynucleotides having a sequence identity to the mature polypeptide coding sequence of SEQ ID NO: 1, SEQ ID NO: 5, or SEQ ID NO: 11 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 3 of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 17 of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 9, SEQ ID NO: 15, or SEQ ID NO: 21 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 7 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 13 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide of SEQ ID NO: 19 at least 90%, e.g., at least 91%, at least 92%, at least 93%, at least 94%, at least 95%, at least 96%, at least 97%, at least 98%, at least 99%, or 100%, which encode a polypeptide having cellulolytic enhancing activity.

Modification of a polynucleotide encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, or the cDNA sequences thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

The present invention also relates to isolated polynucleotides encoding polypeptides of the present invention, which hybridize under medium-high, high, or very high stringency conditions with (i) the mature polypeptide coding sequence of SEQ ID NO: 1, SEQ ID NO: 3, SEQ ID NO: 5, SEQ ID NO: 11, or SEQ ID NO: 17, (ii) the cDNA sequence contained in the mature polypeptide coding sequence of SEQ ID NO: 1, SEQ ID NO: 3, SEQ ID NO: 5, SEQ ID NO: 11, or SEQ ID NO: 17, or (iii) the full-length complementary strand of (i) or (ii); high or very high stringency conditions with (i) the mature polypeptide coding sequence of SEQ ID NO: 7, SEQ ID NO: 9, SEQ ID NO: 13, SEQ ID NO: 15, or SEQ ID NO: 21, (ii) the cDNA sequence contained in the mature polypeptide coding sequence of SEQ ID NO: 7, SEQ ID NO: 9, SEQ ID NO: 13, SEQ ID NO: 15, or SEQ ID NO: 21, or (iii) the full-length complementary strand of (i) or (ii); or very high stringency conditions with (i) the mature polypeptide coding sequence of SEQ ID NO: 19, (ii) the cDNA sequence contained in the mature polypeptide coding sequence of SEQ ID NO: 19, or (iii) the full-length complementary strand of (i) or (ii); or allelic variants and subsequences thereof (Sambrook et al., 1989, supra), as defined herein.

In one aspect, the polynucleotide comprises or consists of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, or the mature polypeptide coding sequences thereof, or a subsequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21 that encodes a fragment of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, respectively, having cellulolytic enhancing activity, such as the polynucleotide of nucleotides 52 to 875 of SEQ ID NO: 1, nucleotides 58 to 1250 of SEQ ID NO: 3, nucleotides 52 to 795 of SEQ ID NO: 5, nucleotides 58 to 974 of SEQ ID NO: 7, nucleotides 64 to 1104 of SEQ ID NO: 9, nucleotides 73 to 990 of SEQ ID NO: 11, nucleotides 49 to 1218 of SEQ ID NO: 13, nucleotides 55 to 930 of SEQ ID NO: 15, nucleotides 67 to 1581 of SEQ ID NO: 17, nucleotides 49 to 865 of SEQ ID NO: 19, or nucleotides 58 to 1065 of SEQ ID NO: 21.

In another aspect, the polynucleotide comprises or consists of SEQ ID NO: 1 or the mature polypeptide coding sequence thereof, which is contained in plasmid pSMai216 which is contained in *E. coli* NRRL B-50301, wherein the polynucleotide sequence encodes a polypeptide having cellulolytic enhancing activity. In another aspect, the polynucleotide comprises or consists of SEQ ID NO: 3 or the mature polypeptide coding sequence thereof, which is contained in plasmid pSMAi217 which is contained in *E. coli* NRRL B-50302, wherein the polynucleotide sequence encodes a polypeptide having cellulolytic enhancing activity. In another aspect, the polynucleotide comprises or consists of SEQ ID NO: 5 or the mature polypeptide coding sequence thereof, which is contained in plasmid pSMai218 which is contained in *E. coli* NRRL B-50303, wherein the polynucleotide sequence encodes a polypeptide having cellulolytic enhancing activity. In another aspect, the polynucleotide comprises or consists of SEQ ID NO: 7 or the mature polypeptide coding sequence thereof, which is contained in plasmid pSMai213 which is contained in *E. coli* NRRL B-50300, wherein the polynucleotide sequence encodes a polypeptide having cellulolytic enhancing activity. In another aspect, the polynucleotide comprises or consists of SEQ ID NO: 9 or the mature polypeptide coding sequence thereof, which is contained in plasmid pAG68 which is contained in *E. coli* NRRL B-50320, wherein the polynucleotide sequence encodes a polypeptide having cellulolytic enhancing activity. In another aspect, the polynucleotide comprises or consists of SEQ ID NO: 11 or the mature polypeptide coding sequence thereof, which is contained in plasmid pAG69 which is contained in *E. coli* NRRL B-50321, wherein the polynucleotide sequence encodes a polypeptide having cellulolytic enhancing activity. In another aspect, the polynucleotide comprises or consists of SEQ ID NO: 13 or the mature polypeptide coding sequence thereof, which is contained in plasmid pAG75 which is contained in *E. coli* NRRL B-50322, wherein the polynucleotide sequence encodes a polypeptide having cellulolytic enhancing activity. In another aspect, the polynucleotide comprises or consists of SEQ ID NO: or the mature polypeptide coding sequence thereof, which is contained in plasmid pAG76 which is contained in *E. coli* NRRL B-50323, wherein the polynucleotide sequence encodes a polypeptide having cellulolytic enhancing activity. In another aspect, the polynucleotide comprises or consists of SEQ ID NO: 17 or the mature polypeptide coding sequence thereof, which is contained in plasmid pAG77 which is contained in *E. coli* NRRL B-50324, wherein the polynucleotide sequence encodes a polypeptide having cellulolytic enhancing activity. In another aspect, the polynucleotide comprises or consists of SEQ ID NO: 19 or the mature polypeptide coding sequence thereof, which is contained in plasmid pAG78 which is contained in *E. coli* NRRL B-50325, wherein the polynucleotide sequence encodes a polypeptide having cellulolytic enhancing activity. In another aspect, the polynucleotide comprises or consists of SEQ ID NO: 21 or the mature polypeptide coding sequence thereof, which is contained in plasmid pAG79 which is contained in *E. coli* NRRL B-50326, wherein the polynucleotide sequence encodes a polypeptide having cellulolytic enhancing activity.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American,* 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from a gene encoding a neutral alpha-amylase in Aspergilli in which the untranslated leader has been replaced by an untranslated leader from a gene encoding triose phosphate isomerase in Aspergilli; non-limiting examples include modified promoters from the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207), by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium*

*graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Thielavia*. In a more preferred aspect, the cell is *Thielavia terrestris*. In a most preferred aspect, the cell is *Thielavia terrestris* NRRL 8126.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (several) expression constructs encoding a polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Removal or Reduction of Cellulolytic Enhancing Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In a particularly preferred aspect, the polynucleotide is disrupted with a selectable marker such as those described herein.

The present invention also relates to methods of inhibiting the expression of a polypeptide having cellulolytic enhancing activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for the expression of native and heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially cellulolytic enhancing-free product are of particular interest in the production of eukaryotic polypeptides, in particular fungal proteins such as enzymes. The cellulolytic enhancing-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellulolytic enhancing activity that is produced by a method of the present invention.

Compositions

The present invention also relates to compositions comprising a polypeptide of the present invention. Preferably, the compositions are enriched in such a polypeptide. The term "enriched" indicates that the endoglucanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as one or more (several) enzymes selected from the group consisting of a cellulase, a hemicellulase, an expansin, an esterase, a laccase, a ligninolytic enzyme, a pectinase, a peroxidase, a protease, and a swollenin.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to the following methods for using the polypeptides having cellulolytic enhancing activity, or compositions thereof.

The present invention also relates to methods for degrading or converting a cellulosic material, comprising: treating the cellulosic material with an enzyme composition in the presence of a polypeptide having cellulolytic enhancing activity of the present invention. In one aspect, the method further comprises recovering the degraded or converted cellulosic material. Soluble products of degradation or conversion of the cellulosic material can be separated from the insoluble cellulosic material using technology well known in the art such as, for example, centrifugation, filtration, and gravity settling.

The present invention also relates to methods of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (several) fermenting microorganisms to produce the fermentation product; and (c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with an enzyme composition in the presence of a polypeptide having cellulolytic enhancing activity of the present invention. In one aspect, the fermenting of the cellulosic material produces a fermentation product. In another aspect, the method further comprises recovering the fermentation product from the fermentation.

The methods of the present invention can be used to saccharify the cellulosic material to fermentable sugars and convert the fermentable sugars to many useful substances, e.g., fuel, potable ethanol, and/or fermentation products (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and co-fermentation (HHCF); and direct microbial conversion (DMC). SHF uses separate process steps to first enzymatically hydrolyze the cellulosic material to fermentable sugars, e.g., glucose, cellobiose, cellotriose, and pentose sugars, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment.

In practicing the methods of the present invention, any pretreatment process known in the art can be used to disrupt plant cell wall components of the cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, Biofuels *Bioproducts and Biorefining-Biofpr.* 2: 26-40).

The cellulosic material can also be subjected to particle size reduction, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment: In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with the cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, the cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from the cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: The cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, the cellulosic material is subjected to mechanical, chemical, or physical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and alternatively also hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having cellulolytic enhancing activity of the present invention. The enzymes of the compositions can be added sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature, and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

The enzyme compositions can comprise any protein that is useful in degrading or converting the cellulosic material.

In one aspect, the enzyme composition comprises or further comprises one or more (several) proteins selected from the group consisting of a cellulase, a polypeptide having cellulolytic enhancing activity, a hemicellulase, an expansin, an esterase, a laccase, a ligninolytic enzyme, a pectinase, a peroxidase, a protease, and a swollenin. In another aspect, the cellulase is preferably one or more (several) enzymes selected from the group consisting of an endoglucanase, a cellobiohydrolase, and a beta-glucosidase. In another aspect, the hemicellulase is preferably one or more (several) enzymes selected from the group consisting of an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (several) cellulolytic enzymes. In another aspect, the enzyme composition comprises or further comprises one or more (several) hemicellulolytic enzymes. In another aspect, the enzyme composition comprises one or more (several) cellulolytic enzymes and one or more (several) hemicellulolytic enzymes. In another aspect, the enzyme composition comprises one or more (several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity. In another aspect, the enzyme composition comprises an acetylmannan esterase. In another aspect, the enzyme composition comprises an acetyxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase). In another aspect, the enzyme composition comprises an expansin. In another aspect, the enzyme composition comprises an esterase. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the methods of the present invention, the enzyme(s) can be added prior to or during fermentation, e.g., during saccharification or during or after propagation of the fermenting microorganism(s).

One or more (several) components of the enzyme composition may be wild-type proteins, recombinant proteins, or a combination of wild-type proteins and recombinant proteins. For example, one or more (several) components may be native proteins of a cell, which is used as a host cell to express recombinantly one or more (several) other components of the enzyme composition. One or more (several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having cellulolytic enhancing activity depend on several factors including, but not limited to, the mixture of component cellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In a preferred aspect, an effective amount of cellulolytic enzyme to the cellulosic material is about 0.5 to about 50 mg, preferably about 0.5 to about 40 mg, more preferably about 0.5 to about 25 mg, more preferably about 0.75 to about 20 mg, more preferably about 0.75 to about 15 mg, even more preferably about 0.5 to about 10 mg, and most preferably about 2.5 to about 10 mg per g of the cellulosic material.

In another preferred aspect, an effective amount of a polypeptide having cellulolytic enhancing activity to the cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably about 0.025 to about 1.5 mg, more preferably about 0.05 to about 1.25 mg, more preferably about 0.075 to about 1.25 mg, more preferably about 0.1 to about 1.25 mg, even more preferably about 0.15 to about 1.25 mg, and most preferably about 0.25 to about 1.0 mg per g of the cellulosic material.

In another preferred aspect, an effective amount of a polypeptide having cellulolytic enhancing activity to cellulolytic enzyme is about 0.005 to about 1.0 g, preferably about 0.01 to about 1.0 g, more preferably about 0.15 to about 0.75 g, more preferably about 0.15 to about 0.5 g, more preferably about 0.1 to about 0.5 g, even more preferably about 0.1 to about 0.25 g, and most preferably about 0.05 to about 0.2 g per g of cellulolytic enzyme.

The polypeptides having cellulolytic enzyme activity or hemicellulolytic enzyme activity as well as other proteins/polypeptides useful in the degradation of the cellulosic material, e.g., polypeptides having cellulolytic enhancing activity (hereinafter "polypeptides having enzyme activity") can be derived or obtained from any suitable origin, including, bacterial, fungal, yeast, plant, or mammalian origin. The term "obtained" means herein that the enzyme may have been isolated from an organism that naturally produces the enzyme as a native enzyme. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another preferred aspect, the polypeptide is a *Streptococcus equisimilis, Streptococcus pyogenes, Streptococcus uberis*, or *Streptococcus equi* subsp. *Zooepidemicus* polypeptide having enzyme activity.

In another preferred aspect, the polypeptide is a *Streptomyces achromogenes, Streptomyces avermitilis, Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having enzyme activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having enzyme activity.

Chemically modified or protein engineered mutants of polypeptides having enzyme activity may also be used.

One or more (several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (several) cellulolytic enzymes comprise a commercial cellulolytic enzyme preparation. Examples of commercial cellulolytic enzyme preparations suitable for use in the present invention include, for example, CELLIC™ CTec (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), ROHAMENT™ 7069 W (Röhm GmbH), FIBREZYME® LDI (Dyadic International, Inc.), FIBREZYME® LBR (Dyadic International, Inc.), or VISCOSTAR® 150 L (Dyadic International, Inc.). The cellulase enzymes are added in amounts effective from about 0.001 to about 5.0 wt % of solids, more preferably from about 0.025 to about 4.0 wt % of solids, and most preferably from about 0.005 to about 2.0 wt % of solids.

Examples of bacterial endoglucanases that can be used in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention include, but are not limited to, a *Trichoderma reesei* endoglucanase I (Penttila et al., 1986, *Gene* 45: 253-263; *Trichoderma reesei* Cel7B endoglucanase I; GENBANK™ accession no. M15665); *Trichoderma reesei* endoglucanase II (Saloheimo, et al., 1988, *Gene* 63:11-22; *Trichoderma reesei* Cel5A endoglucanase II; GENBANK™ accession no. M19373); *Trichoderma reesei* endoglucanase III (Okada et al., 1988, *Appl. Environ. Microbiol.* 64: 555-563; GENBANK™ accession no. AB003694); *Trichoderma reesei* endoglucanase V (Saloheimo et al., 1994, *Molecular Microbiology* 13: 219-228; GENBANK™ accession no. Z33381); *Aspergillus aculeatus* endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V; *Myceliophthora thermophila* CBS 117.65 endoglucanase; basidiomycete CBS 495.95 endoglucanase; basidiomycete CBS 494.95 endoglucanase; *Thielavia terrestris* NRRL 8126 CEL6B endoglucanase; *Thielavia terrestris* NRRL 8126 CEL6C endoglucanase; *Thielavia terrestris* NRRL 8126 CEL7C endoglucanase; *Thielavia terrestris* NRRL 8126 CEL7E endoglucanase; *Thielavia terrestris* NRRL 8126 CEL7F endoglucanase; *Cladorrhinum foecundissimum* ATCC 62373 CEL7A endoglucanase; and *Trichoderma reesei* strain No. VTT-D-80133 endoglucanase (GENBANK™ accession no. M15665).

Examples of cellobiohydrolases useful in the present invention include, but are not limited to, *Trichoderma reesei* cellobiohydrolase I; *Trichoderma reesei* cellobiohydrolase II; *Humicola insolens* cellobiohydrolase I; *Myceliophthora thermophila* cellobiohydrolase II; *Thielavia terrestris* cellobiohydrolase II (CEL6A); *Chaetomium thermophilum* cellobiohydrolase I; and *Chaetomium thermophilum* cellobiohydrolase II.

Examples of beta-glucosidases useful in the present invention include, but are not limited to, *Aspergillus oryzae* beta-glucosidase; *Aspergillus fumigatus* beta-glucosidase; *Penicillium brasilianum* IBT 20888 beta-glucosidase; *Aspergillus niger* beta-glucosidase; and *Aspergillus aculeatus* beta-glucosidase.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499. The *Penicillium brasilianum* polypeptide having beta-glucosidase activity can be obtained according to WO 2007/019442. The *Aspergillus niger* polypeptide having beta-glucosidase activity can be obtained according to Dan et al., 2000, *J. Biol. Chem.* 275: 4973-4980. The *Aspergillus aculeatus* polypeptide having beta-glucosidase activity can be obtained according to Kawaguchi et al., 1996, *Gene* 173: 287-288.

The beta-glucosidase may be a fusion protein. In one aspect, the beta-glucosidase is the *Aspergillus oryzae* beta-glucosidase variant BG fusion protein or the *Aspergillus oryzae* beta-glucosidase fusion protein obtained according to WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in EP 495,257, EP 531,315, EP 531,372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/0076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 4,435,307, U.S. Pat. No. 5,457,046, U.S. Pat. No. 5,648,263, U.S. Pat. No. 5,686,593, U.S. Pat. No. 5,691,178, U.S. Pat. No. 5,763,254, and U.S. Pat. No. 5,776,757.

Examples of polypeptides having cellulolytic enhancing activity useful in the methods of the present invention include, but are not limited to, polypeptides having cellulolytic enhancing activity from *Thielavia terrestris* (WO 2005/074647); polypeptides having cellulolytic enhancing activity from *Thermoascus aurantiacus* (WO 2005/074656); polypeptides having cellulolytic enhancing activity from *Trichoderma reesei* (WO 2007/089290); and polypeptides having cellulolytic enhancing activity from *Myceliophthora thermophila* (WO 2009/085935; WO 2009/085859; WO 2009/085864; WO 2009/085868).

In one aspect, the one or more (several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC™ HTec (Novozymes A/S), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the methods of the present invention include, but are not limited to, *Aspergillus aculeatus* xylanase (GeneSeqP:AAR63790; WO 94/21785), *Aspergillus fumigatus* xylanases (WO 2006/078256), and *Thielavia terrestris* NRRL 8126 xylanases (WO 2009/079210).

Examples of beta-xylosidases useful in the methods of the present invention include, but are not limited to, *Trichoderma reesei* beta-xylosidase (UniProtKB/TrEMBL accession number Q92458), *Talaromyces emersonii* (SwissProt accession number Q8×212), and *Neurospora crassa* (SwissProt accession number Q7SOW4).

Examples of acetylxylan esterases useful in the methods of the present invention include, but are not limited to, *Hypocrea jecorina* acetylxylan esterase (WO 2005/001036), *Neurospora crassa* acetylxylan esterase (UniProt accession number q7s259), *Thielavia terrestris* NRRL 8126 acetylxylan esterase (WO 2009/042846), *Chaetomium globosum* acetylxylan esterase (Uniprot accession number Q2GWX4), *Chaetomium gracile* acetylxylan esterase (GeneSeqP accession number AAB82124), *Phaeosphaeria nodorum* acetylxylan esterase (Uniprot accession number Q0UHJ1), and *Humicola insolens* DSM 1800 acetylxylan esterase (WO 2009/073709).

Examples of ferulic acid esterases useful in the methods of the present invention include, but are not limited to, *Humicola insolens* DSM 1800 feruloyl esterase (WO 2009/076122), *Neurospora crassa* feruloyl esterase (UniProt accession number Q9HGR3), and *Neosartorya fischeri* feruloyl esterase (UniProt Accession number A1D9T4).

Examples of arabinofuranosidases useful in the methods of the present invention include, but are not limited to, *Humicola insolens* DSM 1800 arabinofuranosidase (WO 2009/073383) and *Aspergillus niger* arabinofuranosidase (GeneSeqP accession number AAR94170).

Examples of alpha-glucuronidases useful in the methods of the present invention include, but are not limited to, *Aspergillus clavatus* alpha-glucuronidase (UniProt accession number a1cc12), *Trichoderma reesei* alpha-glucuronidase (Uniprot accession number Q99024), *Talaromyces emersonii* alpha-glucuronidase (UniProt accession number Q8×211), *Aspergillus niger* alpha-glucuronidase (Uniprot accession number Q96WX9), *Aspergillus terreus* alpha-glucuronidase (SwissProt accession number Q0CJP9), and *Aspergillus fumigatus* alpha-glucuronidase (SwissProt accession number Q4WW45).

The enzymes and proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of the *Saccharomyces* spp., preferably *Saccharomyces cerevisiae*.

Examples of fermenting organisms that can ferment $C_5$ sugars include bacterial and fungal organisms, such as some yeast. Preferred $C_5$ fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis*; *Hansenula*, such as *Hansenula anomala*; *Kluyveromyces*, such as *K. fragilis*; *Schizosaccharomyces*, such as *S. pombe*; *E. coli*, especially *E. coli* strains that have been genetically modified to improve the yield of ethanol; *Clostridium*, such as *Clostridium acetobutylicum*, *Chlostridium thermocellum*, and *Chlostridium phytofermentans*; *Geobacillus* sp.; *Thermoanaerobacter*, such as *Thermoanaerobacter saccharolyticum*; and *Bacillus*, such as *Bacillus coagulans*.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis*, *Clostridium acetobutylicum*, *Clostridium thermocellum*, *Chlostridium phytofermentans*, *Geobacillus* sp., *Thermoanaerobacter saccharolyticum*, and *Bacillus coagulans* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (Fermentis/Lesaffre, USA), FALI™ (Fleischmann's Yeast, USA), SUPERSTART™ and THERMOSACC™ fresh yeast (Ethanol Technology, WI, USA), BIOFERM™ AFT and XR (NABC—North American Bioproducts Corporation, GA, USA), GERT STRAND™ (Gert Strand AB, Sweden), and FERMIOL™ (DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces* sp.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded cellulosic material and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Detergent Compositions

The polypeptides having cellulolytic enhancing activity of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. Consequently, the present invention also relates to methods for cleaning or washing a hard surface or laundry, comprising contacting the hard surface or the laundry with a detergent composition of the present invention.

In a specific aspect, the present invention provides a detergent additive comprising a polypeptide of the invention. The detergent additive as well as the detergent composition may further comprise one or more (several) enzymes selected from the group consisting of an amylase, an arabinase, a carbohydrase, a cellulase, a cutinase, a galactanase, a hemicellulase, a laccase, a lipase, a mannanase, an oxidase, a pectinase, a protease, and a xylanase.

one or more enzymes such as a protease, lipase, cutinase, an amylase, carbohydrase, cellulase, pectinase, mannanase, arabinase, galactanase, xylanase, oxidase, e.g., a laccase, and/or peroxidase. further comprising one or more enzymes selected from the group consisting of a cellulase, a protease, a lipase, a cutinase, an amylase, a carbohydrase, a pectinase, a mannanase, an arabinase, a galactanase, a xylanase, and an oxidase In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME™, and CAREZYME™ (Novozymes A/S), CLAZINASE™, and PURADAX HA™ (Genencor International Inc.), and KAC-500(B)™ (Kao Corporation).

Proteases:

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include ALCALASE™, SAVINASE™, PRIMASE™, DURALASE™, ESPERASE™, and KANNASE™ (Novozymes A/S), MAXATASE™, MAXACAL™, MAXAPEM™, PROPERASE™, PURAFECT™, PURAFECT OXP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes A/S).

Amylases:

Suitable amylases (alpha and/or beta) include those of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes A/S), RAPIDASE™ and PURASTAR™ (from Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste, or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a polypeptide of the present invention having cellulolytic enhancing activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A polypeptide of the invention having cellulolytic enhancing activity may also be incorporated in the detergent formulations disclosed in WO 97/07202, which is hereby incorporated by reference.

Signal Peptide

The present invention also relates to an isolated polynucleotide encoding a signal peptide comprising or consisting of amino acids 1 to 17 of SEQ ID NO: 2, amino acids 1 to 19 of SEQ ID NO: 4, amino acids 1 to 17 of SEQ ID NO: 6, amino acids 1 to 19 of SEQ ID NO: 8, amino acids 1 to 21 of SEQ ID NO: 10, amino acids 1 to 24 of SEQ ID NO: 12, amino acids 1 to 16 of SEQ ID NO: 14, amino acids 1 to 18 of SEQ ID NO: 16, amino acids 1 to 22 of SEQ ID NO: 18, amino acids 1 to 16 of SEQ ID NO: 20, or amino acids 1 to 19 of SEQ ID NO: 22. The polynucleotide may further comprise a gene encoding a protein, which is operably linked to the signal peptide. The protein is preferably foreign to the signal peptide.

The present invention also relates to nucleic acid constructs, expression vectors and recombinant host cells comprising such a polynucleotide.

The present invention also relates to methods of producing a protein, comprising: (a) cultivating a recombinant host cell comprising such a polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone or variant thereof, enzyme, receptor or portion thereof, antibody or portion thereof, or reporter. For example, the protein may be an oxidoreductase, transferase, hydrolase, lyase, isomerase, or ligase such as an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strains

*Thielavia terrestris* NRRL 8126 was used as the source of the Family 61 polypeptides having cellulolytic enhancing activity. *Aspergillus oryzae* JaL355 strain (WO 2002/40694) was used for expression of the *Thielavia terrestris* Family 61 genes encoding the polypeptides having cellulolytic enhancing activity.

Media and Solutions

PDA plates were composed of 39 g of potato dextrose agar and distilled water to 1 liter.

NNCYP medium was composed of 5.0 g of $NaNO_3$, 3.0 g of $NH_4Cl$, 2.0 g of MES, 2.5 g of citric acid, 0.2 g of $CaCl_2$ $2H_2O$, 1.0 g of Bacto Peptone, 5.0 g of yeast extract, 0.2 g of $MgSO_4$ $7H_2O$, 4.0 g of $K_2HPO_4$, 1.0 ml of COVE trace elements solution, 2.5 g of glucose, and distilled water to 1 liter.

Minimal medium (MM) plates were composed of 6 g of $NaNO_3$, 0.52 g of KCl, 1.52 g of $KH_2PO_4$, 1 ml of COVE trace elements solution, 20 g of Noble agar, 20 ml of 50% glucose, 2.5 ml of $MgSO_4.7H_2O$, 20 ml of a 0.02% biotin solution, and distilled water to 1 liter.

COVE trace elements solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and distilled water to 1 liter.

M410 medium was composed of 50 g of maltose, 50 g of glucose, 2 g of $MgSO_4.7H_2O$, 4 g of citric acid anhydrous powder, 2 g of $KH_2PO_4$, 8 g of yeast extract, 2 g of urea, 0.5 g of $CaCl_2$, 0.5 ml of AMG trace metals solution, and distilled water to 1 liter.

AMG trace metals solution was composed of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, 3 g of citric acid, and distilled water to 1 liter.

Example 1: Source of DNA Sequence Information for *Thielavia terrestris* NRRL 8126

Genomic sequence information was generated by the U.S. Department of Energy Joint Genome Institute (JGI). A preliminary assembly of the genome was downloaded from JGI and analyzed using the Pedant-Pro™ Sequence Analysis Suite (Biomax Informatics AG, Martinsried, Germany). Gene models constructed by the software were used as a starting point for detecting GH61 homologues in the genome. More precise gene models were constructed manually using multiple known GH61 protein sequences as a guide.

Example 2: *Thielavia terrestris* NRRL 8126 Genomic DNA Extraction

To generate genomic DNA for PCR amplification, *Thielavia terrestris* NRRL 8126 was grown in 50 ml of NNCYP medium supplemented with 1% glucose in a baffled shake flask at 42° C. and 200 rpm for 24 hours. Mycelia were harvested by filtration, washed twice in TE (10 mM Tris-1 mM EDTA), and frozen under liquid nitrogen. A pea-size piece of frozen mycelia was suspended in 0.7 ml of 1% lithium dodecyl sulfate in TE and disrupted by agitation with an equal volume of 0.1 mm zirconia/silica beads (Biospec Products, Inc., Bartlesville, Okla., USA) for 45 seconds in a FastPrep FP120 (ThermoSavant, Holbrook, N.Y., USA). Debris was removed by centrifugation at 13,000×g for 10 minutes and the cleared supernatant was brought to 2.5 M ammonium acetate and incubated on ice for 20 minutes. After the incubation period, the nucleic acids were precipitated by addition of 2 volumes of ethanol. After centrifugation for 15 minutes in a microfuge at 4° C., the pellet was washed in 70% ethanol and air dried. The DNA was resuspended in 120 µl of 0.1×TE and incubated with 1 µl of DNase-free RNase A at 37° C. for 20 minutes. Ammonium acetate was added to 2.5 M and the DNA was precipitated with 2 volumes of ethanol. The pellet was washed in 70% ethanol, air dried, and resuspended in TE buffer.

Example 3: Construction of an *Aspergillus oryzae* Expression Vector Containing *Thielavia terrestris* NRRL 8126 Genomic Sequence Encoding a Family GH61J Polypeptide Having Cellulolytic Enhancing Activity Two synthetic oligonucleotide primers shown below were designed to PCR amplify the *Thielavia terrestris* NRRL 8126 gh61j gene from the genomic DNA prepared in Example 2. An IN-FUSION™ Cloning Kit (BD Biosciences, Palo Alto, Calif., USA) was used to clone the fragment directly into the expression vector pAILo2 (WO 2004/099228), without the need for restriction digests and ligation.

Ttghlj-F (065367):

(SEQ ID NO: 23)
5'-ACTGGATTTACCATGAAGTTCTCACTGGTGTC-3'

Ttgh61j-R (065368):

(SEQ ID NO: 24)
5'-TCACCTCTAGTTAATTAATCAGCAGGAGATCGGGGCGG-3'

Bold letters represent coding sequence. The remaining sequence is homologous to the insertion sites of pAILo2.

Fifty picomoles of each of the primers above were used in a PCR reaction composed of 100 ng of *Thielavia terrestris* NRRL 8126 genomic DNA, Pfx Amplification Buffer (Invitrogen, Carlsbad, Calif., USA), 0.4 mM each of dATP, dTTP, dGTP, and dCTP, 1 mM $MgCl_2$, and 2.5 units of Pfx DNA polymerase (Invitrogen, Carlsbad, Calif., USA) in a final volume of 50 µl. The amplification was performed using an EPPENDORF® MASTERCYCLER® 5333 (Eppendorf Scientific, Inc., Westbury, N.Y., USA) programmed for 1 cycle at 98° C. for 3 minutes; and 30 cycles each at 98° C. for 30 seconds, 60° C. for 30 seconds, and 72° C. for 1.5 minutes. The heat block then went to a 4° C. soak cycle.

The reaction products were isolated on a 1.0% agarose gel using 40 mM Tris base-20 mM sodium acetate-1 mM disodium EDTA (TAE) buffer where a 908 bp product band was excised from the gel and purified using a MINELUTE® Gel Extraction Kit (QIAGEN Inc., Valencia, Calif., USA) according to the manufacturer's instructions. The fragment was then cloned into Nco I and Pac I digested pAILo2 using an IN-FUSION™ Cloning Kit resulting in pSMai207 in which transcription of the *Thielavia terrestris* gh61j gene was under the control of a NA2-tpi promoter (a modified promoter from the gene encoding neutral alpha-amylase in *Aspergillus niger* in which the untranslated leader has been replaced by an untranslated leader from the gene encoding triose phosphate isomerase in *Aspergillus nidulans*). The ligation reaction (50 µl) was composed of 1×IN-FUSION™ Buffer (BD Biosciences, Palo Alto, Calif., USA), 1×BSA (BD Biosciences, Palo Alto, Calif., USA), 1 µl of IN-FUSION™ enzyme (diluted 1:10) (BD Biosciences, Palo Alto, Calif., USA), 100 ng of pAILo2 digested with Nco I and Pac I, and 50 ng of the *Thielavia terrestris* gh61j purified PCR product. The reaction was incubated at room temperature for 30 minutes. One µl of the reaction was used to transform *E. coli* XL10 SOLOPACK® Gold Supercompetent cells (Stratagene, La Jolla, Calif., USA). An *E. coli* transformant containing pSMai207 was detected by restriction digestion and plasmid DNA was prepared using a BIOROBOT® 9600 (QIAGEN Inc., Valencia, Calif., USA). The *Thielavia terrestris* gh61j insert in pSMai207 was confirmed by DNA sequencing.

The same 908 bp *Thielavia terrestris* gh61j PCR fragment was also cloned into pCR®2.1-TOPO vector (Invitrogen, Carlsbad, Calif., USA) using a TOPO® TA CLONING® Kit (Invitrogen, Carlsbad, Calif., USA), to generate pSMai216. The *Thielavia terrestris* gh61j insert was confirmed by DNA sequencing. *E. coli* pSMai216 was deposited with the Agricultural Research Service Patent Culture Collection, Northern Regional Research Center, Peoria, Ill., USA, on Aug. 3, 2009 and assigned accession number NRRL B-50301.

Example 4: Characterization of the *Thielavia terrestris* NRRL 8126 Genomic Sequence Encoding a GH61J Polypeptide Having Cellulolytic-Enhancing Activity DNA sequencing of the *Thielavia terrestris* NRRL 8126 gh61j genomic clone was performed with an Applied Biosystems Model 3700 Automated DNA Sequencer using version 3.1 BIG-DYE™ terminator chemistry (Applied Biosystems, Inc., Foster City, Calif., USA) and dGTP chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA). The sequence obtained was identical to the sequence from JGI.

The nucleotide sequence (SEQ ID NO: 1) and deduced amino acid sequence (SEQ ID NO: 2) of the *Thielavia terrestris* gh61j gene are shown in FIG. 1. The coding sequence is 878 bp including the stop codon and is interrupted by introns of 66 and 71 bp. The encoded predicted protein is 246 amino acids. The % G+C of the coding sequence of the gene (including introns) is 63% G+C and the mature polypeptide coding sequence is 63%. Using the SignalP program (Nielsen et al., 1997, *Protein Engineering* 10:1-6), a signal peptide of 17 residues was predicted. The predicted mature protein contains 229 amino acids with a predicted molecular mass of 24.5 kDa and an isoelectric pH of 7.85.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Thielavia terrestris* gene encoding the GH61J polypeptide having cellulolytic-enhancing activity shares 57.7% identity (excluding gaps) to the deduced amino acid sequence of a predicted GH61 family protein from *Humicola insolens* (accession numbers geneseqp:ADM97935).

Example 5: Expression of *Thielavia terrestris* NRRL 8126 Family 61 Glycosyl Hydrolase 61j Gene in *Aspergillus oryzae* JaL355

*Aspergillus oryzae* JaL355 (WO 2002/40694) protoplasts were prepared according to the method of Christensen et al., 1988, *Bio/Technology* 6: 1419-1422, which were transformed with approximately 2 µg of pSMai207. The transformation yielded about 30 transformants. Ten transformants were isolated to individual Minimal Medium plates.

Confluent Minimal Medium plates of each of the transformants were washed with 5 ml of 0.01% TWEEN® 20 and inoculated separately into 25 ml of M410 medium in 125 ml glass shake flasks and incubated at 34° C., 250 rpm. After 5 days incubation, 5 µl of supernatant from each culture were analyzed on CRITERION® Tris-HCl gels (Bio-Rad Laboratories, Hercules, Calif., USA) with a CRITERION® Cell (Bio-Rad Laboratories, Hercules, Calif., USA), according to the manufacturer's instructions. The resulting gels were stained with BIO-SAFE™ Coomassie Stain (Bio-Rad Laboratories, Hercules, Calif., USA). SDS-PAGE profiles of the cultures showed that the majority of the transformants had an expected 24 KDa band size. A confluent plate of transformant 3 was washed with 10 ml of 0.01% TWEEN® 80 and inoculated into a 2 liter Fernbach containing 500 ml of M410 medium to generate broth for characterization of the enzyme. The culture was harvested on day 5 and filtered using a 0.22 µm EXPRESS™ PLUS Membrane (Millipore, Billerica, Mass., USA).

Example 6: Construction of an *Aspergillus oryzae* Expression Vector Containing *Thielavia terrestris* NRRL 8126 Genomic Sequence Encoding a Family GH61K Polypeptide Having Cellulolytic Enhancing Activity Two synthetic oligonucleotide primers shown below were designed to PCR amplify the *Thielavia terrestris* NRRL 8126 gh61k gene from the genomic DNA prepared in Example 2. An IN-FUSION™ Cloning Kit was used to clone the fragment directly into the expression vector pAILo2, without the need for restriction digests and ligation. Ttgh1k-F (065465):

(SEQ ID NO: 25)
5'-ACTGGATTTACCATGAGGACGACATTCGCCGCCGCGT-3'

Ttgh61k-R (065466):

(SEQ ID NO: 26)
5'-TCACCTCTAGTTAATTAACTAAGAAGAAGGGGCGCACT-3'

Bold letters represent coding sequence. The remaining sequence is homologous to the insertion sites of pAILo2.

Fifty picomoles of each of the primers above were used in a PCR reaction composed of 100 ng of *Thielavia terrestris* NRRL 8126 genomic DNA, Pfx Amplification Buffer, 0.4 mM each of dATP, dTTP, dGTP, and dCTP, 1 mM $MgCl_2$, and 2.5 units of Pfx DNA polymerase in a final volume of 50 µl. The amplification was performed using an EPPENDORF® MASTERCYCLER® 5333 programmed for 1 cycle at 98° C. for 3 minutes; and 30 cycles each at 98° C. for 30 seconds, 60° C. for 30 seconds, and 72° C. for 1.5 minutes. The heat block then went to a 4° C. soak cycle.

The reaction products were isolated on a 1.0% agarose gel using TAE buffer where a 1283 bp product band was excised from the gel and purified using a MINELUTE® Gel Extraction Kit according to the manufacturer's instructions. The fragment was then cloned into Nco I and Pac I digested pAILo2 using an IN-FUSION™ Cloning Kit resulting in pSMai208 in which transcription of the *Thielavia terrestris* gh61k gene was under the control of a NA2-tpi promoter. The ligation reaction (50 µl) was composed of 1×IN-FUSION™ Buffer, 1×BSA, 1 µl of IN-FUSION™ enzyme (diluted 1:10), 100 ng of pAILo2 digested with Nco I and Pac I, and 50 ng of the *Thielavia terrestris* gh61k purified PCR product. The reaction was incubated at room temperature for 30 minutes. One µl of the reaction was used to transform *E. coli* XL10 SOLOPACK® Gold Supercompetent cells. An *E. coli* transformant containing pSMai208 was detected by restriction digestion and plasmid DNA was prepared using a BIOROBOT® 9600. The *Thielavia terrestris* gh61k insert in pSMai208 was confirmed by DNA sequencing.

The same 1283 bp *Thielavia terrestris* gh61k PCR fragment was also cloned into pCR®2.1-TOPO vector using a TOPO TA CLONING® Kit, to generate pSMai217. The *Thielavia terrestris* gh61k insert was confirmed by DNA sequencing. *E. coli* pSMai217 was deposited with the Agricultural Research Service Patent Culture Collection, Northern Regional Research Center, Peoria, Ill., USA, on Aug. 3, 2009 and assigned accession number NRRL B-50302.

Example 7: Characterization of the *Thielavia terrestris* NRRL 8126 Genomic Sequence Encoding a GH61K Polypeptide Having Cellulolytic-Enhancing Activity DNA sequencing of the *Thielavia terrestris* NRRL 8126 gh61k genomic clone was performed with an Applied Biosystems Model 3700 Automated DNA Sequencer using version 3.1 BIG-DYE™ terminator chemistry and dGTP chemistry and primer walking strategy. Nucleotide sequence data were scrutinized for quality and all sequences were compared to each other with assistance of PHRED/PHRAP software. The sequence obtained was identical to the sequence from the JGI.

The nucleotide sequence (SEQ ID NO: 3) and deduced amino acid sequence (SEQ ID NO: 4) of the *Thielavia terrestris* gh61k gene are shown in FIG. 2. The coding sequence is 1253 bp including the stop codon and is interrupted by introns of 96, 84 and 68 bp. The encoded predicted protein is 334 amino acids. The % G+C of the coding sequence of the gene (including introns) is 66.6% G+C and the mature polypeptide coding sequence is 69.3%. Using the SignalP program (Nielsen et al., 1997, supra), a signal peptide of 19 residues was predicted. The predicted mature protein contains 315 amino acids with a predicted molecular mass of 31.7 kDa and an isoelectric pH of 6.68.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Thielavia terrestris* gene encoding the GH61K polypeptide having cellulolytic-enhancing activity shares 64.8% identity (excluding gaps) to the deduced amino acid sequence of a predicted beta-glucosidase protein from *Penicillium brasilianum* (accession numbers geneseqp AWW27060).

Example 8: Expression of *Thielavia terrestris* NRRL 8126 Family 61 Glycosyl Hydrolase 61k Gene in *Aspergillus oryzae* JaL355

*Aspergillus oryzae* JaL355 (WO 2002/40694) protoplasts were prepared according to the method of Christensen et al., 1988, supra, which were transformed with approximately 2 µg of pSMai208. The transformation yielded about 25 transformants. Ten transformants were isolated to individual Minimal Medium plates.

Confluent Minimal Medium plates of each of the transformants were washed with 5 ml of 0.01% TWEEN® 20 and inoculated separately into 25 ml of M410 medium in 125 ml glass shake flasks and incubated at 34° C., 250 rpm. After 5 days incubation, 5 µl of supernatant from each culture were analyzed on CRITERION® Tris-HCl gels with a CRITERION® Cell, according to the manufacturer's instructions. The resulting gels were stained with BIO-SAFE™ Coomassie Stain. SDS-PAGE profiles of the cultures showed that the majority of the transformants had an expected 32 KDa band size. A confluent plate of transformant 5 was washed with 10 ml of 0.01% TWEEN® 80 and inoculated into a 2 liter Fernbach containing 500 ml of M410 medium to generate broth for characterization of the enzyme. The culture was harvested on day 5 and filtered using a 0.22 µm EXPRESS™ PLUS Membrane.

Example 9: Construction of an *Aspergillus oryzae* Expression Vector Containing *Thielavia terrestris* NRRL 8126 Genomic Sequence Encoding a Family GH61L Polypeptide Having Cellulolytic Enhancing Activity Two synthetic oligonucleotide primers shown below were designed to PCR amplify the *Thielavia terrestris* NRRL 8126 gh61l gene from the genomic DNA prepared in Example 2. An IN-FUSION™ Cloning Kit was used to clone the fragment directly into the expression vector pAILo2, without the need for restriction digests and ligation. Ttgh1l-F1 (066276):

```
                                       (SEQ ID NO: 27)
5'-ACTGGATTTACCATGAAGCTGAGCGTTGCCATCGCC-3'
```

Ttgh6l-R (065736):

```
                                       (SEQ ID NO: 28)
5'-TCACCTCTAGTTAATTAATTAGCACGTCTCAGCCGGCG-3'
```

Bold letters represent coding sequence. The remaining sequence is homologous to the insertion sites of pAILo2.

Fifty picomoles of each of the primers above were used in a PCR reaction composed of 100 ng of *Thielavia terrestris*

NRRL 8126 genomic DNA, Pfx Amplification Buffer, 0.4 mM each of dATP, dTTP, dGTP, and dCTP, 1 mM $MgCl_2$, and 2.5 units of Pfx DNA polymerase in a final volume of 50 µl. The amplification was performed using an EPPENDORF® MASTERCYCLER® 5333 programmed for 1 cycle at 98° C. for 3 minutes; and 30 cycles each at 98° C. for 30 seconds, 60° C. for 30 seconds, and 72° C. for 1.5 minutes. The heat block then went to a 4° C. soak cycle.

The reaction products were isolated on a 1.0% agarose gel using TAE buffer where a 828 bp product band was excised from the gel and purified using a MINELUTE® Gel Extraction Kit according to the manufacturer's instructions. The fragment was then cloned into Nco I and Pac I digested pAILo2 using an IN-FUSION™ Cloning Kit resulting in pSMai209 in which transcription of the *Thielavia terrestris* gh61l gene was under the control of a NA2-tpi promoter. The ligation reaction (50 µl) was composed of 1×IN-FUSION™ Buffer, 1×BSA, 1 µl of IN-FUSION™ enzyme (diluted 1:10), 100 ng of pAILo2 digested with Nco I and Pac I, and 50 ng of the *Thielavia terrestris* gh61l purified PCR product. The reaction was incubated at room temperature for 30 minutes. One µl of the reaction was used to transform *E. coli* XL10 SOLOPACK® Gold Supercompetent cells. An *E. coli* transformant containing pSMai212 was detected by restriction digestion and plasmid DNA was prepared using a BIOROBOT® 9600. The *Thielavia terrestris* gh61l insert in pSMai212 was confirmed by DNA sequencing.

The same 828 bp *Thielavia terrestris* gh61l PCR fragment was also cloned into pCR®2.1-TOPO vector using a TOPO TA CLONING® Kit, to generate pSMai218. The *Thielavia terrestris* gh61l insert was confirmed by DNA sequencing. *E. coli* pSMai218 was deposited with the Agricultural Research Service Patent Culture Collection, Northern Regional Research Center, Peoria, Ill., USA, on Aug. 3, 2009 and assigned accession number NRRL B-50303.

Example 10: Characterization of the *Thielavia terrestris* NRRL 8126 Genomic Sequence Encoding a GH61L Polypeptide Having Cellulolytic-Enhancing Activity DNA sequencing of the *Thielavia terrestris* NRRL 8126 gh61l genomic clone was performed with an Applied Biosystems Model 3700 Automated DNA Sequencer using version 3.1 BIG-DYE™ terminator chemistry and dGTP chemistry and primer walking strategy. Nucleotide sequence data were scrutinized for quality and all sequences were compared to each other with assistance of PHRED/PHRAP software. The sequence obtained was identical to the sequence from the JGI.

The nucleotide sequence (SEQ ID NO: 5) and deduced amino acid sequence (SEQ ID NO: 6) of the *Thielavia terrestris* gh61l gene are shown in FIG. 3. The coding sequence is 798 bp including the stop codon and is interrupted by introns of 55 and 59 bp. The encoded predicted protein is 227 amino acids. The % G+C of the coding sequence of the gene (including introns) is 60.8% G+C and the mature polypeptide coding sequence is 62.6%. Using the SignalP program (Nielsen et al., 1997, supra), a signal peptide of 17 residues was predicted. The predicted mature protein contains 210 amino acids with a predicted molecular mass of 22.6 kDa and an isoelectric pH of 8.84.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Thielavia terrestris* gene encoding the GH61L polypeptide having cellulolytic-enhancing activity shares 59.2% identity (excluding gaps) to the deduced amino acid sequence of a predicted GH61 family protein from *Thielavia terrestris* (accession numbers geneseqp ADM97933).

Example 11: Expression of *Thielavia terrestris* NRRL 8126 Family 61 Glycosyl Hydrolase 61l Gene in *Aspergillus oryzae* JaL355

*Aspergillus oryzae* JaL355 (WO 2002/40694) protoplasts were prepared according to the method of Christensen et al., 1988, supra, which were transformed with approximately 2 µg of pSMai212. The transformation yielded about 17 transformants. Seventeen transformants were isolated to individual Minimal Medium plates.

Confluent Minimal Medium plates of each of the transformants were washed with 5 ml of 0.01% TWEEN® 20 and inoculated separately into 25 ml of M410 medium in 125 ml glass shake flasks and incubated at 34° C., 250 rpm. After 5 days incubation, 5 µl of supernatant from each culture were analyzed on CRITERION® Tris-HCl gels with a CRITERION® Cell, according to the manufacturer's instructions. The resulting gels were stained with BIO-SAFE™ Coomassie Stain. SDS-PAGE profiles of the cultures showed that the majority of the transformants had an expected 23 KDa band size. A confluent plate of transformant 14 was washed with 10 ml of 0.01% TWEEN® 80 and inoculated into a 2 liter Fernbach containing 500 ml of M410 medium to generate broth for characterization of the enzyme. The culture was harvested on day 5 and filtered using a 0.22 µm EXPRESS™ PLUS Membrane.

Example 12: Hydrolysis of Pretreated Corn Stover is Enhanced by *Thielavia terrestris* NRRL 8126 GH61J, GH61K, and GFH61L Polypeptides Having Cellulolytic Enhancing Activity Culture broth was prepared as described in Examples 5, 8, and 11 and concentrated approximately 20-fold using an Amicon ultrafiltration device (Millipore, Bedford, Mass., USA, 10 kDa polyethersulfone membrane, 40 psi, 4° C.). Protein concentration was estimated by densitometry following SDS-PAGE and Coomassie blue staining. Corn stover was pretreated and prepared as an assay substrate as described in WO 2005/074647 to generate pretreated corn stover (PCS). The base cellulase mixture used to assay enhancing activity was prepared from *Trichoderma reesei* strain SMA135 (WO 2008/057637).

Hydrolysis of PCS was conducted using 1.6 ml deep-well plates (Axygen, Santa Clara, Calif., USA) using a total reaction volume of 1.0 ml and a PCS concentration of 50 mg/ml in 1 mM manganese sulfate-50 mM sodium acetate, pH 5.0. The *T. terrestris* polypeptides (GH61J, GH61K, and GFH61L) were separately added to the base cellulase mixture at concentrations ranging from 0 to 25% or 0 to 32% of the protein concentration of the base cellulase mixture. Incubation was at 50° C. for 72 hours. Assays were performed in triplicate. Aliquots were centrifuged, and the supernatant liquid was filtered by centrifugation (MULTISCREEN® HV 0.45 µm, Millipore, Billerica, Mass., USA) at 3000 rpm for 10 minutes using a plate centrifuge (SORVALL® RT7, Thermo Fisher Scientific, Waltham, Mass., USA). When not used immediately, filtered hydrolysate aliquots were frozen at −20° C. Sugar concentrations of samples diluted in 0.005 M H$_2$SO$_4$ with 0.05% w/w benzoic acid were measured after elution by 0.005 M H$_2$SO$_4$ with 0.05% w/w benzoic acid at a flow rate of 0.6 ml/minute from a 4.6×250 mm AMINEX® HPX-87H column (Bio-Rad Laboratories, Inc., Hercules, Calif., USA) at 65° C. with quantitation by integration of glucose and cellobiose signals from refractive index detection (CHEMSTATION®, AGILENT® 1100 HPLC, Agilent Technologies, Santa Clara, Calif., USA) calibrated by pure sugar samples (Absolute Standards Inc., Hamden, Conn., USA). The resultant equivalents were used to calculate the percentage of cellulose conversion for each reaction. The degree of cellulose conversion to glucose plus cellobiose sugars (conversion, %) was calculated using the following equation:

Conversion (%)=(glucose+cellobiose×1.053)(mg/ml)×100×162/(Cellulose(mg/ml)×180)=(glucose+cellobiose×1.053)(mg/ml)×100/(Cellulose (mg/ml)×1.111)

In this equation the factor 1.111 reflects the weight gain in converting cellulose to glucose, and the factor 1.053 reflects the weight gain in converting cellobiose to glucose. Cellulose in PCS was determined by a limit digest of PCS to release glucose and cellobiose.

The results of adding increasing amounts of *Thielavia terrestris* polypeptides separately to the base cellulase mix are shown in FIG. 4. Addition of each of the *T. terrestris* GH61J and GH61K polypeptides provided a stimulation factor of 1.14 and 1.13, respectively, at a 25% addition level. *T. terrestris* GH61L polypeptide provided a stimulation factor of 1.13 at a 32% addition level.

Example 13: Construction of an *Aspergillus oryzae* Expression Vector Containing *Thielavia terrestris* NRRL 8126 Genomic Sequence Encoding a Family GH61M Polypeptide Having Cellulolytic Enhancing Activity Two synthetic oligonucleotide primers shown below were designed to PCR amplify the *Thielavia terrestris* NRRL 8126 gh61m gene from the genomic DNA prepared in Example 2. An IN-FUSION™ Cloning Kit was used to clone the fragment directly into the expression vector pAILo2 (WO 2004/099228), without the need for restriction digests and ligation.
Tth1m-F1 (063567):

(SEQ ID NO: 29)
5'-ACTGGATTTACCATGAAGCTGTCATCCCAGCTCGCC-3'

Ttgh61m-R1 (063568):

(SEQ ID NO: 30)
5'-TCACCTCTAGTTAATTAACTAGCACTGAAAGACCGCCG-3'

Bold letters represent coding sequence. The remaining sequence is homologous to the insertion sites of pAILo2.

Fifty picomoles of each of the primers above were used in a PCR reaction composed of 100 ng of *Thielavia terrestris* NRRL 8126 genomic DNA, Pfx Amplification Buffer, 0.4 mM each of dATP, dTTP, dGTP, and dCTP, 1 mM MgCl$_2$, and 2.5 units of Pfx DNA polymerase in a final volume of 50 µl. The amplification was performed using an EPPENDORF® MASTERCYCLER® 5333 programmed for 1 cycle at 98° C. for 3 minutes; and 30 cycles each at 98° C. for 30 seconds, 60° C. for 30 seconds, and 72° C. for 1.5 minutes. The heat block then went to a 4° C. soak cycle.

Figure 5:
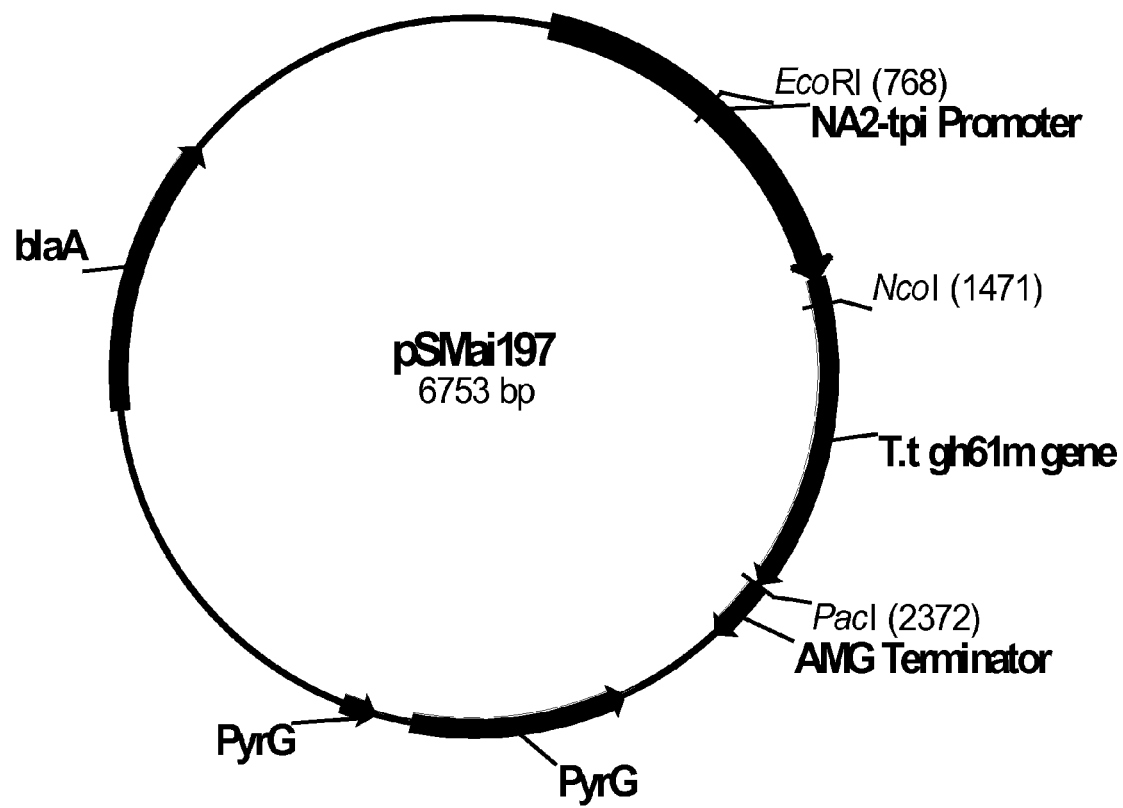
FIG. 5 shows a restriction map of pSMai197.

The reaction products were isolated on a 1.0% agarose gel using TAE buffer where a 1007 bp product band was excised from the gel and purified using a MINELUTE® Gel Extraction Kit according to the manufacturer's instructions. The fragment was then cloned into Nco I and Pac I digested pAILo2 using an IN-FUSION™ Cloning Kit resulting in pSMai197 (FIG. 5) in which transcription of the *Thielavia terrestris* gh61m gene was under the control of the NA2-tpi promoter. The ligation reaction (50 µl) was composed of 1×IN-FUSION™ Buffer, 1×BSA, 1 µl of IN-FUSION™ enzyme (diluted 1:10), 100 ng of pAILo2 digested with Nco I and Pac I, and 50 ng of the *Thielavia terrestris* gh61m purified PCR product. The reaction was incubated at room temperature for 30 minutes. One µl of the reaction was used to transform *E. coli* XL10 SOLOPACK® Gold Supercompetent cells. An *E. coli* transformant containing pSMai197 was detected by restriction digestion and plasmid DNA was prepared using a BIOROBOT® 9600. The *Thielavia terrestris* gh61m insert in pSMai197 was confirmed by DNA sequencing.

The same 1007 bp *Thielavia terrestris* gh61m PCR fragment was also cloned into pCR®2.1-TOPO vector using a TOPO TA CLONING® Kit to generate pSMai213. The *Thielavia terrestris* gh61m insert was confirmed by DNA sequencing. *E. coli* pSMai213 was deposited with the Agricultural Research Service Patent Culture Collection, Northern Regional Research Center, Peoria, Ill., USA, on Aug. 3, 2009 and assigned accession number NRRL B-50300.

Example 14: Characterization of the *Thielavia terrestris* NRRL 8126 Genomic Sequence Encoding a GH61M Polypeptide Having Cellulolytic-Enhancing Activity DNA sequencing of the *Thielavia terrestris* NRRL 8126 gh61m genomic clone was performed with an Applied Biosystems Model 3700 Automated DNA Sequencer using version 3.1 BIG-DYE™ terminator chemistry and dGTP chemistry and primer walking strategy. Nucleotide sequence data were scrutinized for quality and all sequences were compared to each other with assistance of PHRED/PHRAP software. The sequence obtained was identical to the sequence from the JGI.

The nucleotide sequence (SEQ ID NO: 7) and deduced amino acid sequence (SEQ ID NO: 8) of the *Thielavia terrestris* gh61m gene are shown in FIG. 6. The coding sequence is 977 bp including the stop codon and is interrupted by introns of 85, 96 and 124 bp. The encoded predicted protein is 223 amino acids. The % G+C of the coding sequence of the gene (including introns) is 62.6% G+C and the mature polypeptide coding sequence is 62.2%. Using the SignalP program (Nielsen et al., 1997, supra), a signal peptide of 19 residues was predicted. The predicted mature protein contains 204 amino acids with a predicted molecular mass of 22.2 kDa and an isoelectric pH of 6.58.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Thielavia terrestris* gene encoding the GH61M polypeptide having cellulolytic-enhancing activity shares 76.5% identity (excluding gaps) to the deduced amino acid sequence of a predicted GH61 family protein from *Podospora anserina* (accession numbers Uni-Prot B2ADY5).

Example 15: Expression of *Thielavia terrestris* NRRL 8126 Family 61 Glycosyl Hydrolase 61m Gene in *Aspergillus oryzae* JaL355

*Aspergillus oryzae* JaL355 (WO 2002/40694) protoplasts were prepared according to the method of Christensen et al., 1988, supra, which were transformed with approximately 2 μg of pSMai197. The transformation yielded about 17 transformants. Ten transformants were isolated to individual Minimal Medium plates.

Confluent Minimal Medium plates of each of the transformants were washed with 5 ml of 0.01% TWEEN® 20 and inoculated separately into 25 ml of M410 medium in 125 ml glass shake flasks and incubated at 34° C., 250 rpm. After 5 days incubation, 5 μl of supernatant from each culture were analyzed on CRITERION® Tris-HCl gels with a CRITERION® Cell, according to the manufacturer's instructions. The resulting gels were stained with BIO-SAFE™ Coomassie Stain. SDS-PAGE profiles of the cultures showed that the majority of the transformants had an expected 22 kDa band size. A confluent plate of transformant 9 was washed with 10 ml of 0.01% TWEEN® 80 and inoculated into a 2 liter Fernbach containing 500 ml of M410 medium to generate broth for characterization of the enzyme. The culture was harvested on day 5 and filtered using a 0.22 μm EXPRESS™ PLUS Membrane.

Example 16: Hydrolysis of Pretreated Corn Stover is Enhanced by *Thielavia terrestris* NRRL 8126 GH61M Polypeptide Having Cellulolytic Enhancing Activity Culture broth was prepared as described in Example 15 and concentrated approximately 20-fold using an Amicon ultrafiltration device (Millipore, Bedford, Mass., USA, 10 kDa polyethersulfone membrane, 40 psi, 4° C.). Protein concentration was estimated by densitometry following SDS-PAGE and Coomassie blue staining. Corn stover was pretreated and prepared as an assay substrate as described in WO 2005/074647 to generate pretreated corn stover (PCS). The base cellulase mixture used to assay enhancing activity was prepared from *Trichoderma reesei* strain SMA135 (WO 2008/057637).

Hydrolysis of PCS was conducted using 1.6 ml deep-well plates (Axygen, Santa Clara, Calif., USA) using a total reaction volume of 1.0 ml and a PCS concentration of 50 mg/ml in 1 mM manganese sulfate-50 mM sodium acetate, pH 5.0. The *T. terrestris* polypeptide (GH61M) was added to the base cellulase mixture at concentrations ranging from 0 to 25% of the protein concentration of the base cellulase mixture. Incubation was at 50° C. for 72 hours. Assays were performed in triplicate. Aliquots were centrifuged, and the supernatant liquid was filtered by centrifugation (MULTISCREEN® HV 0.45 μm) at 3000 rpm for 10 minutes using a plate centrifuge (SORVALL® RT7, Thermo Fisher Scientific, Waltham, Mass., USA). When not used immediately, filtered hydrolysate aliquots were frozen at −20° C. Sugar concentrations of samples diluted in 0.005 M $H_2SO_4$ with 0.05% w/w benzoic acid were measured after elution by 0.005 M $H_2SO_4$ with 0.05% w/w benzoic acid at a flow rate of 0.6 ml/minute from a 4.6×250 mm AMINEX® HPX-87H column at 65° C. with quantitation by integration of glucose and cellobiose signals from refractive index detection calibrated by pure sugar samples (Absolute Standards Inc., Hamden, Conn., USA). The resultant equivalents were used to calculate the percentage of cellulose conversion for each reaction. The degree of cellulose conversion to glucose plus cellobiose sugars (conversion, %) was calculated using the following equation:

$$\text{Conversion (\%)} = (\text{glucose+cellobiose} \times 1.053)(\text{mg/ml}) \times 100 \times 162/(\text{Cellulose}(\text{mg/ml}) \times 180) = (\text{glucose+cellobiose} \times 1.053)(\text{mg/ml}) \times 100/(\text{Cellulose}(\text{mg/ml}) \times 1.111)$$

In this equation the factor 1.111 reflects the weight gain in converting cellulose to glucose, and the factor 1.053 reflects the weight gain in converting cellobiose to glucose. Cellulose in PCS was determined by a limit digest of PCS to release glucose and cellobiose.

Figure 7:
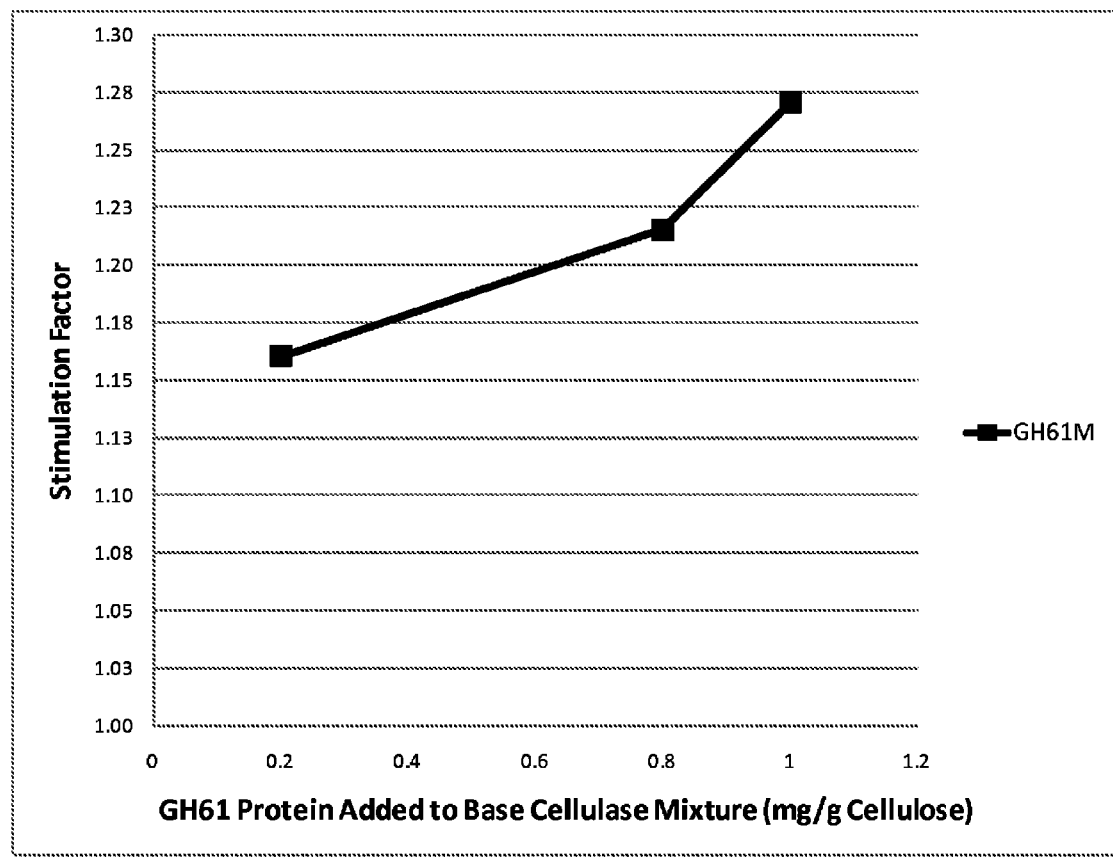
FIG. 7 shows hydrolysis of pretreated corn stover (PCS) with a *Trichoderma reesei* cellulase mixture in the presence of varying concentrations of *Thielavia terrestris* NRRL 8126 GH61M polypeptide having cellulolytic enhancing activity.

The results of adding increasing amounts of the *T. terrestris* GH61M polypeptide to the base cellulase mix are shown in FIG. 7. Addition of the *T. terrestris* GH61M polypeptide provided a stimulation factor of 1.27 at a 25% addition level.

Example 17: Construction of an *Aspergillus oryzae* Expression Vector for the *Thielavia terrestris* Family GH61N Gene Two synthetic oligonucleotide primers shown below were designed to PCR amplify the *Thielavia terrestris* Family GH61N gene from the genomic DNA prepared in Example 2. An IN-FUSION™ Cloning Kit was used to clone the fragment directly into the expression vector, pAILo2, without the need for restriction digests and ligation.

Forward Primer:

(SEQ ID NO: 31)
5'-ACTGGATTTACCATGCCTTCTTTCGCCTCCAA-3'

Reverse Primer:

(SEQ ID NO: 32)
5'-TCACCTCTAGTTAATTAATCAGTTTGCCTCCTCAGCCC-3'

Bold letters represent coding sequence. The remaining sequence is homologous to the insertion sites of pAILo2.

Fifty picomoles of each of the primers above were used in a PCR reaction containing 1 μg of *Thielavia terrestris* genomic DNA, 1× ADVANTAGE® GC-Melt LA Buffer (BD Biosciences, Palo Alto, Calif., USA), 1 μl of 10 mM blend of dATP, dTTP, dGTP, and dCTP, and 1.25 units of ADVANTAGE® GC Genomic LA Polymerase Mix (BD Biosciences, Palo Alto, Calif., USA), in a final volume of 25 μl. The amplification conditions were one cycle at 94° C. for 1 minute; and 30 cycles each at 94° C. for 30 seconds, 60.5° C. for 30 seconds, and 72° C. for 1 minute. The heat block was then held at 72° C. for 5 minutes followed by a 4° C. soak cycle.

The reaction products were isolated by 1.0% agarose gel electrophoresis using TAE buffer where an approximately 1.1 kb product band was excised from the gel and purified using a MINELUTE® Gel Extraction Kit according to the manufacturer's instructions.

The fragment was then cloned into pAILo2 using an IN-FUSION™ Cloning Kit. The vector was digested with Nco I and Pac I. The fragment was purified by 1.0% agarose gel electrophoresis using TAE buffer, excised from the gel, and purified using a QIAQUICK® Gel Extraction Kit (QIAGEN Inc., Valencia, Calif., USA). The gene fragment and the digested vector were combined together in a reaction resulting in the expression plasmid pAG66, in which transcription of the Family GH61N gene was under the control of the NA2-tpi promoter. The recombination reaction (20 μl) was composed of 1×IN-FUSION™ Buffer, 1×BSA, 1 μl of IN-FUSION™ enzyme (diluted 1:10), 186 ng of pAILo2 digested with Nco I and Pac I, and 96.6 ng of the *Thielavia terrestris* GH61N purified PCR product. The reaction was incubated at 37° C. for 15 minutes followed by 15 minutes at 50° C. The reaction was diluted with 40 μl of TE buffer and 2.5 μl of the diluted reaction was used to transform *E. coli* Top10 Competent cells (Stratagene, La Jolla, Calif., USA). An *E. coli* transformant containing pAG66 (GH61N gene) was identified by restriction enzyme digestion and plasmid DNA was prepared using a BIOROBOT® 9600.

The same 1.1 kb *Thielavia terrestris* gh61n PCR fragment was also cloned into pCR®2.1-TOPO vector using a TOPO® TA CLONING® Kit, to generate pAG68. The *Thielavia terrestris* gh61n insert was confirmed by DNA sequencing. *E. coli* pAG68 was deposited with the Agricultural Research Service Patent Culture Collection, Northern Regional Research Center, Peoria, Ill., USA, on Sep. 18, 2009 and assigned accession number NRRL B-50320.

Example 18: Characterization of the *Thielavia terrestris* Genomic Sequence Encoding a Family GH61N Polypeptide Having Cellulolytic Enhancing Activity The nucleotide sequence (SEQ ID NO: 9) and deduced amino acid sequence (SEQ ID NO: 10) of the *Thielavia terrestris* GH61N polypeptide having cellulolytic enhancing activity are shown in FIG. 8. The genomic polynucleotide is 1107 bp, including the stop codon, and encodes a polypeptide of 368 amino acids. The % G+C content of the full-length coding sequence and the mature coding sequence is 68.1% and 68.3%, respectively. Using the SignalP software program (Nielsen et al., 1997, supra), a signal peptide of 21 residues was predicted. The predicted mature protein contains 347 amino acids with a molecular mass of 35.0 kDa.

Analysis of the deduced amino acid sequence of the GH61N polypeptide having cellulolytic enhancing activity with the Interproscan program (Mulder et al., 2007, *Nucleic Acids Res.* 35: D224-D228) showed that the GH61N polypeptide contained the sequence signature of glycoside hydrolase Family 61 (InterPro accession IPR005103). This sequence signature was found from approximately residues 1 to 221 of the mature polypeptide (Pfam accession PF03443).

A comparative pair wise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Thielavia terrestris* GH61N mature polypeptide shares 72.3% identity (excluding gaps) to the deduced amino acid sequence of another predicted Family 61 glycoside hydrolase protein from *Aspergillus niger* (UniProt accession number A2QZE1).

Example 19: Expression of the *Thielavia terrestris* Genomic DNA Encoding Family GH61N Polypeptides Having Cellulolytic Enhancing Activity in *Aspergillus oryzae* JaL355

*Aspergillus oryzae* JaL355 protoplasts were prepared according to the method of Christensen et al., 1988, supra, which were transformed with 5 μg of pAG43. Three transformants were isolated to individual PDA plates.

Plugs were taken from the original transformation plate of each of the three transformants and added separately to 1 ml of M410 medium in 24 well plates, which were incubated at 34° C. Five days after incubation, 7.5 μl of supernatant from each culture was analyzed using CRITERION® stain-free, 8-16% gradient SDS-PAGE, (Bio-Rad Laboratories, Inc., Hercules, Calif., USA) according to the manufacturer's instructions. SDS-PAGE profiles of the cultures showed that several transformants had new major bands of approximately 70 kDa and 35 kDa.

Confluent PDA plates of two of the transformants were washed with 5 ml of 0.01% TWEEN® 20 and inoculated into five 500 ml Erlenmeyer flask containing 100 ml of M410 medium and incubated to generate broth for characterization of the enzyme. The flasks were harvested on days 3 and 5 and filtered using a 0.22 μm stericup suction filter (Millipore, Bedford, Mass., USA).

Example 20: Hydrolysis of Pretreated Corn Stover is Enhanced by *Thielavia terrestris* GH61N Polypeptide Having Cellulolytic Enhancing Activity Culture broth was prepared as described in Example 19 and concentrated approximately 20-fold using an Amicon ultrafiltration device (Millipore, Bedford, Mass., USA, 10 kDa polyethersulfone membrane, 40 psi, 4° C.). Protein concentration was estimated by densitometry following SDS-PAGE and Coomassie blue staining. Corn stover was pretreated and prepared as an assay substrate as described in WO 2005/074647 to generate pretreated corn stover (PCS). The base cellulase mixture used to assay enhancing activity was prepared from *Trichoderma reesei* strain SMA135 (WO 2008/057637).

Hydrolysis of PCS was conducted using 1.6 ml deep-well plates (Axygen, Santa Clara, Calif.) using a total reaction volume of 1.0 ml and a PCS concentration of 50 mg/ml in 1 mM manganese sulfate-50 mM sodium acetate, pH 5.0. The *T. terrestris* polypeptide (GH61N) was separately added to the base cellulase mixture at concentrations ranging from 0 to 100% of the protein concentration of the base cellulase mixture. Incubation was at 50° C. for 72 hours. Assays were performed in triplicate. Aliquots were centrifuged, and the supernatant liquid was filtered by centrifugation (MULTISCREEN® HV 0.45 μm, Millipore, Billerica, Mass., USA) at 3000 rpm for 10 minutes using a plate centrifuge (SORVALL® RT7, Thermo Fisher Scientific, Waltham, Mass., USA). When not used immediately, filtered hydrolysate aliquots were frozen at −20° C. Sugar concentrations of samples diluted in 0.005 M $H_2SO_4$ with 0.05% w/w benzoic acid were measured after elution by 0.005 M $H_2SO_4$ with 0.05% w/w benzoic acid at a flow rate of 0.6 ml/minute from a 4.6×250 mm AMINEX® HPX-87H column (Bio-Rad Laboratories, Inc., Hercules, Calif., USA) at 65° C. with quantitation by integration of glucose and cellobiose signals from refractive index detection (CHEMSTATION®, AGILENT® 1100 HPLC, Agilent Technologies, Santa Clara, Calif., USA) calibrated by pure sugar samples (Absolute Standards Inc., Hamden, Conn., USA). The resultant equivalents were used to calculate the percentage of cellulose conversion for each reaction. The degree of cellulose conversion to glucose plus cellobiose sugars (conversion, %) was calculated using the following equation:

$$\text{Conversion (\%)} = (\text{glucose} + \text{cellobiose} \times 1.053)(\text{mg/ml}) \times 100 \times 162/(\text{Cellulose(mg/ml)} \times 180) = (\text{glucose} + \text{cellobiose} \times 1.053)(\text{mg/ml}) \times 100/(\text{Cellulose (mg/ml)} \times 1.111)$$

In this equation the factor 1.111 reflects the weight gain in converting cellulose to glucose, and the factor 1.053 reflects the weight gain in converting cellobiose to glucose. Cellulose in PCS was determined by a limit digest of PCS to release glucose and cellobiose.

Figure 9:
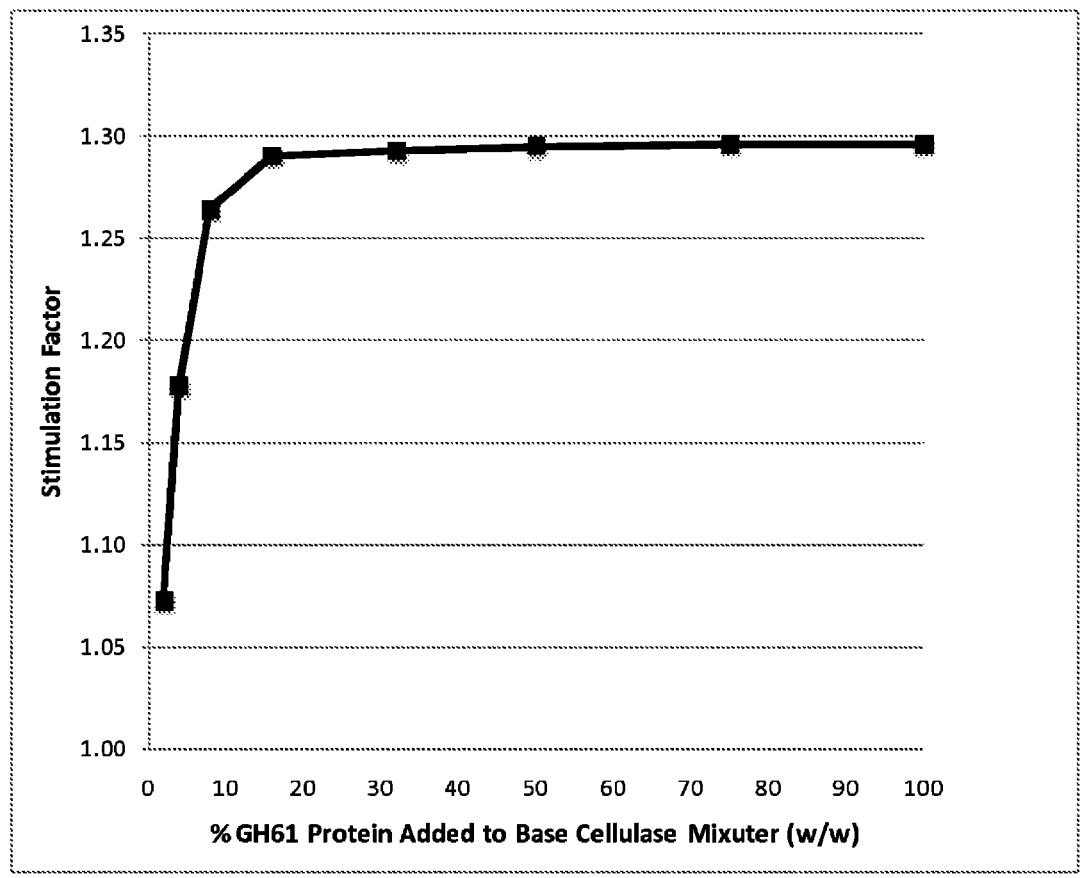
FIG. 9 shows hydrolysis of pretreated corn stover (PCS) with a *Trichoderma reesei* cellulase mixture in the presence of varying concentrations of *Thielavia terrestris* NRRL 8126 GH61N polypeptide having cellulolytic enhancing activity.

The results of adding increasing amounts of *Thielavia terrestris* polypeptide separately to the base cellulase mix are shown in FIG. 9. Addition of the *T. terrestris* GH61N provided a maximum stimulatory benefit of 1.30 at an addition percentage of 50%.

Example 21: Construction of an *Aspergillus oryzae* Expression Vector for the *Thielavia terrestris* Family GH61O Gene Two synthetic oligonucleotide primers shown below were designed to PCR amplify the *Thielavia terrestris* Family GH61O gene from the genomic DNA prepared in Example 2. An IN-FUSION™ Cloning Kit was used to clone the fragment directly into the expression vector, pAILo2, without the need for restriction digests and ligation.
Forward Primer:

(SEQ ID NO: 33)
5'-ACTGGATTTACCATGCCGCCCGCACTCCCTCA-3'

Reverse Primer:

(SEQ ID NO: 34)
5'-TCACCTCTAGTTAATTAACTAACCCCGCCGATCATACC-3'

Bold letters represent coding sequence. The remaining sequence is homologous to the insertion sites of pAILo2.

Fifty picomoles of each of the primers above were used in a PCR reaction containing 1 μg of *Thielavia terrestris* genomic DNA, 1× ADVANTAGE® GC-Melt LA Buffer, 1 μl of 10 mM blend of dATP, dTTP, dGTP, and dCTP, and 1.25 units of ADVANTAGE® GC Genomic LA Polymerase Mix, in a final volume of 25 μl. The amplification conditions were one cycle at 94° C. for 1 minute; and 30 cycles each at 94° C. for 30 seconds, 60.5° C. for 30 seconds, and 72° C. for 1 minute. The heat block was then held at 72° C. for 5 minutes followed by a 4° C. soak cycle.

The reaction products were isolated on a 1.0% agarose gel using TAE buffer where as approximately 1 kb product band was excised from the gel and purified using a MINELUTE® Gel Extraction Kit according to the manufacturer's instructions.

The fragment was then cloned into pAILo2 using an IN-FUSION™ Cloning Kit. The vector was digested with Nco I and Pac I. The fragment was purified by gel electrophoresis and a QIAQUICK® Gel Extraction Kit. The gene fragment and the digested vector were combined together in a reaction resulting in the expression plasmid pAG67, in which transcription of the Family GH61O gene was under the control of the NA2-tpi promoter. The recombination reaction (20 μl) was composed of 1×IN-FUSION™ Buffer, 1×BSA, 1 μl of IN-FUSION™ enzyme (diluted 1:10), 186 ng of pAILo2 digested with Nco I and Pac I, and 90.6 ng of the *Thielavia terrestris* GH61O purified PCR product. The reaction was incubated at 37° C. for 15 minutes followed by 15 minutes at 50° C. The reaction was diluted with 40 μl of TE buffer and 2.5 μl of the diluted reaction was used to transform *E. coli* Top10 Competent cells. An *E. coli* transformant containing pAG67 (GH61O gene) was identified by restriction enzyme digestion and plasmid DNA was prepared using a BIOROBOT® 9600.

The same 1 bp *Thielavia terrestris* gh61o PCR fragment was also cloned into pCR®2.1-TOPO vector using a TOPO® TA CLONING® Kit, to generate pAG69. The *Thielavia terrestris* gh61o insert was confirmed by DNA sequencing. *E. coli* pAG69 was deposited with the Agricultural Research Service Patent Culture Collection, Northern Regional Research Center, Peoria, Ill., USA, on Sep. 18, 2009 and assigned accession number NRRL B-50321.

Example 22: Characterization of the *Thielavia terrestris* Genomic Sequence Encoding a Family GH61O Polypeptide Having Cellulolytic Enhancing Activity The nucleotide sequence (SEQ ID NO: 11) and deduced amino acid sequence (SEQ ID NO: 12) of the *Thielavia terrestris* GH61O polypeptide having cellulolytic enhancing activity are shown in FIG. 10. The genomic polynucleotide is 993 bp, including the stop codon, and encodes a polypeptide of 330 amino acids. The % G+C content of the full-length coding sequence and the mature coding sequence is 69.4% for both. Using the SignalP software program (Nielsen et al., 1997, supra), a signal peptide of 24 residues was predicted. The predicted mature protein contains 306 amino acids with a molecular mass of 32.1 kDa.

Analysis of the deduced amino acid sequence of the GH61O polypeptide having cellulolytic enhancing activity with the Interproscan program (Mulder et al., 2007, supra) showed that the GH61O polypeptide contained the sequence signature of glycoside hydrolase Family 61 (InterPro accession IPR005103). This sequence signature was found from approximately residues 1 to 245 of the mature polypeptide (Pfam accession PF03443).

A comparative pair wise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Thielavia terrestris* GH61O mature polypeptide shares 56.5% identity (excluding gaps) to the deduced amino acid sequence of another predicted Family 61 glycoside hydrolase protein from *Podospora anserina* (UniProt accession number B2AVC8).

Example 23: Construction of an *Aspergillus oryzae* Expression Vector for the *Thielavia terrestris* Family GH61P Gene Two synthetic oligonucleotide primers shown below were designed to PCR amplify the *Thielavia terrestris* Family GH61P gene from the genomic DNA prepared in Example 2. An IN-FUSION™ Cloning Kit was used to clone the fragment directly into the expression vector, pAILo2 (WO 2005/074647), without the need for restriction digests and ligation.
Forward Primer:

(SEQ ID NO: 35)
5'-ACTGGATTTACCATGAAGACATTCACCGCCCTCCTG-3'

Reverse Primer:

(SEQ ID NO: 36)
5'-TCACCTCTAGTTAATTAATCAGCAAGTAAAGACCGCCG-3'

Bold letters represent coding sequence. The remaining sequence is homologous to the insertion sites of pAILo2.

Fifty picomoles of each of the primers above were used in a PCR reaction containing 1 µg of *Thielavia terrestris* genomic DNA, 1× ADVANTAGE® GC-Melt LA Buffer, 1 µl of 10 mM blend of dATP, dTTP, dGTP, and dCTP, and 1.25 units of ADVANTAGE® GC Genomic LA Polymerase Mix, in a final volume of 25 µl. The amplification conditions were one cycle at 94° C. for 1 minute; and 30 cycles each at 94° C. for 30 seconds, 58.5° C. for 30 seconds, and 72° C. for 1.5 minutes. The heat block was then held at 72° C. for 5 minutes followed by a 4° C. soak cycle.

The reaction products were isolated on a 1.0% agarose gel using TAE buffer where an approximately 1.2 kb product band was excised from the gel and purified using a MIN-ELUTE® Gel Extraction Kit according to the manufacturer's instructions.

The fragment was then cloned into pAILo2 using an IN-FUSION™ Cloning Kit. The vector was digested with Nco I and Pac I. The fragment was purified by gel electrophoresis and QIAQUICK® Gel Extraction Kit. The gene fragment and the digested vector were combined together in a reaction resulting in the expression plasmid pAG70, in which transcription of the Family GH61P gene was under the control of the NA2-tpi promoter. The recombination reaction (10 µl) was composed of 1×IN-FUSION™ Buffer, 1×BSA, 0.5 µl of IN-FUSION™ enzyme (diluted 1:10), 93 ng of pAILo2 digested with Nco I and Pac I, and 2 µl of the *Thielavia terrestris* GH61P purified PCR product. The reaction was incubated at 37° C. for 15 minutes followed by 15 minutes at 50° C. The reaction was diluted with 40 µl of TE buffer and 2.5 µl of the diluted reaction was used to transform *E. coli* Top10 Competent cells. An *E. coli* transformant containing pAG70 (GH61P gene) was identified by restriction enzyme digestion and plasmid DNA was prepared using a BIOROBOT® 9600.

The same 1.2 kb *Thielavia terrestris* gh61p PCR fragment was also cloned into pCR®2.1-TOPO vector using a TOPO® TA CLONING® Kit, to generate pAG75. The *Thielavia terrestris* gh61p insert was confirmed by DNA sequencing. *E. coli* pAG75 was deposited with the Agricultural Research Service Patent Culture Collection, Northern Regional Research Center, Peoria, Ill., USA, on Sep. 18, 2009 and assigned accession number NRRL B-50322.

Example 24: Characterization of the *Thielavia terrestris* Genomic Sequence Encoding a Family GH61P Polypeptide Having Cellulolytic Enhancing Activity The nucleotide sequence (SEQ ID NO: 13) and deduced amino acid sequence (SEQ ID NO: 14) of the *Thielavia terrestris* GH61P polypeptide having cellulolytic enhancing activity are shown in FIG. 11. The genomic polynucleotide is 1221 bp, including the stop codon, and the coding sequence is interrupted by three introns of 231, 75, and 96 bp. The predicted coding sequence encodes a polypeptide of 236 amino acids. The % G+C content of the full-length coding sequence (including introns) and the mature coding sequence is 60.2% and 59.8%, respectively. Using the SignalP software program (Nielsen et al., 1997, supra), a signal peptide of 16 residues was predicted. The predicted mature protein contains 220 amino acids with a molecular mass of 23.6 kDa.

Analysis of the deduced amino acid sequence of the GH61P polypeptide having cellulolytic enhancing activity with the Interproscan program (Mulder et al., 2007, supra) showed that the GH61P polypeptide contained the sequence signature of glycoside hydrolase Family 61 (InterPro accession IPR005103). This sequence signature was found from approximately residues 1 to 212 of the mature polypeptide (Pfam accession PF03443).

A comparative pair wise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Thielavia terrestris* GH61P mature polypeptide shares 80.3% identity (excluding gaps) to the deduced amino acid sequence of another predicted Family 61 glycoside hydrolase protein from *Neurospora crassa* (UniProt accession number Q7SA19).

Example 25: Construction of an *Aspergillus oryzae* Expression Vector for the *Thielavia terrestris* Family GH61R Gene Two synthetic oligonucleotide primers shown below were designed to PCR amplify the *Thielavia terrestris* Family GH61R gene from the genomic DNA prepared in Example 2. An IN-FUSION™ Cloning Kit was used to clone the fragment directly into the expression vector, pAILo2 (WO 2005/074647), without the need for restriction digests and ligation.

Forward Primer:

```
                                          (SEQ ID NO: 37)
5'-ACTGGATTTACCATGGCCTTGCTGCTCTTGGCAGGC-3'
```

Reverse Primer:

```
                                          (SEQ ID NO: 38)
5'-TCACCTCTAGTTAATTAATCACCCATCCCATATCGGCC-3'
```

Bold letters represent coding sequence. The remaining sequence is homologous to the insertion sites of pAILo2.

Fifty picomoles of each of the primers above were used in a PCR reaction containing 1 µg of *Thielavia terrestris* genomic DNA, 1× ADVANTAGE® GC-Melt LA Buffer, 1 µl of 10 mM blend of dATP, dTTP, dGTP, and dCTP, and 1.25 units of ADVANTAGE® GC Genomic LA Polymerase Mix, in a final volume of 25 µl. The amplification conditions were one cycle at 94° C. for 1 minute; and 30 cycles each at 94° C. for 30 seconds, 59.4° C. for 30 seconds, and 72° C. for 1.5 minutes. The heat block was then held at 72° C. for 5 minutes followed by a 4° C. soak cycle.

The reaction products were isolated on a 1.0% agarose gel using TAE buffer where as approximately 1 kb product band was excised from the gel and purified using a MINELUTE® Gel Extraction Kit according to the manufacturer's instructions.

The fragment was then cloned into pAILo2 using an IN-FUSION™ Cloning Kit. The vector was digested with Nco I and Pac I. The fragment was purified by gel electrophoresis and QIAQUICK® Gel Extraction Kit. The gene fragment and the digested vector were combined together in a reaction resulting in the expression plasmid pAG71, in which transcription of the Family GH61R gene was under the control of the NA2-tpi promoter. The recombination reaction (10 µl) was composed of 1×IN-FUSION™ Buffer, 1×BSA, 0.5 µl of IN-FUSION™ enzyme (diluted 1:10), 93 ng of pAILo2 digested with Nco I and Pac I, and 2 µl of the Thielavia terrestris GH61R purified PCR product. The reaction was incubated at 37° C. for 15 minutes followed by 15 minutes at 50° C. The reaction was diluted with 40 µl of TE buffer and 2.5 µl of the diluted reaction was used to transform E. coli Top10 Competent cells. An E. coli transformant containing pAG71 (GH61R gene) was identified by restriction enzyme digestion and plasmid DNA was prepared using a BIOROBOT® 9600.

The same 1 kb Thielavia terrestris gh61r PCR fragment was also cloned into pCR®2.1-TOPO vector using a TOPO® TA CLONING® Kit, to generate pAG76. The Thielavia terrestris gh61r insert was confirmed by DNA sequencing. E. coli pAG76 was deposited with the Agricultural Research Service Patent Culture Collection, Northern Regional Research Center, Peoria, Ill., USA, on Sep. 18, 2009 and assigned accession number NRRL B-50323.

Example 26: Characterization of the Thielavia terrestris Genomic Sequence Encoding a Family GH61R Polypeptide Having Cellulolytic Enhancing Activity The nucleotide sequence (SEQ ID NO: 15) and deduced amino acid sequence (SEQ ID NO: 16) of the Thielavia terrestris GH61R polypeptide having cellulolytic enhancing activity are shown in FIG. 12. The genomic polynucleotide is 933 bp, including the stop codon, and the coding sequence is interrupted by three introns of 72, 53, and 55 bp. The predicted coding sequence encodes a polypeptide of 250 amino acids. The % G+C content of the full-length coding sequence (including introns) and the mature coding sequence is 61.8% and 61.6%, respectively. Using the SignalP software program (Nielsen et al., 1997, supra), a signal peptide of 18 residues was predicted. The predicted mature protein contains 232 amino acids with a molecular mass of 26.0 kDa.

Analysis of the deduced amino acid sequence of the GH61R polypeptide having cellulolytic enhancing activity with the Interproscan program (Mulder et al., 2007, supra8) showed that the GH61R polypeptide contained the sequence signature of glycoside hydrolase Family 61 (InterPro accession IPR005103). This sequence signature was found from approximately residues 1 to 224 of the mature polypeptide (Pfam accession PF03443).

A comparative pair wise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the Thielavia terrestris GH61R mature polypeptide shares 72.8% identity (excluding gaps) to the deduced amino acid sequence of another predicted Family 61 glycoside hydrolase protein from Chrysosporium lucknowense (GeneSeqP accession number AWI36233).

Example 27: Construction of an Aspergillus oryzae Expression Vector for the Thielavia terrestris Family GH61S Gene Two synthetic oligonucleotide primers shown below were designed to PCR amplify the Thielavia terrestris Family GH61S gene from the genomic DNA prepared in Example 2. An IN-FUSION™ Cloning Kit was used to clone the fragment directly into the expression vector, pAILo2, without the need for restriction digests and ligation.

Forward Primer:

(SEQ ID NO: 39)
5'-ACTGGATTTACCATGATGCCGTCCCTTGTTCGCTTC-3'

Reverse Primer:

(SEQ ID NO: 40)
5'-TCACCTCTAGTTAATTAATCAACCATGTCTCCTGTCCC-3'

Bold letters represent coding sequence. The remaining sequence is homologous to the insertion sites of pAILo2.

Fifty picomoles of each of the primers above were used in a PCR reaction containing 1 µg of Thielavia terrestris genomic DNA, 1× ADVANTAGE® GC-Melt LA Buffer, 1 µl of 10 mM blend of dATP, dTTP, dGTP, and dCTP, and 1.25 units of ADVANTAGE® GC Genomic LA Polymerase Mix, in a final volume of 25 µl. The amplification conditions were one cycle at 94° C. for 1 minute; and 30 cycles each at 94° C. for 30 seconds, 58.5° C. for 30 seconds, and 72° C. for 1.5 minutes. The heat block was then held at 72° C. for 5 minutes followed by a 4° C. soak cycle. The reaction products were isolated on a 1.0% agarose gel using TAE buffer where as approximately 1.3 kb product band was excised from the gel and purified using a MINELUTE® Gel Extraction Kit according to the manufacturer's instructions.

The fragment was then cloned into pAILo2 using an IN-FUSION™ Cloning Kit. The vector was digested with Nco I and Pac I. The fragment was purified by gel electrophoresis and QIAQUICK® Gel Extraction Kit. The gene fragment and the digested vector were combined together in a reaction resulting in the expression plasmid pAG72, in which transcription of the Family GH61S gene was under the control of the NA2-tpi promoter. The recombination reaction (10 µl) was composed of 1×IN-FUSION™ Buffer, 1×BSA, 0.5 µl of IN-FUSION™ enzyme (diluted 1:10), 93 ng of pAILo2 digested with Nco I and Pac I, and 2 µl of the Thielavia terrestris GH61S purified PCR product. The reaction was incubated at 37° C. for 15 minutes followed by 15 minutes at 50° C. The reaction was diluted with 40 µl of TE buffer and 2.5 µl of the diluted reaction was used to transform E. coli Top10 Competent cells. An E. coli transformant containing pAG72 (GH61S gene) was identified by restriction enzyme digestion and plasmid DNA was prepared using a BIOROBOT® 9600.

The same 1.3 kb Thielavia terrestris gh61s PCR fragment was also cloned into pCR®2.1-TOPO vector using a TOPO® TA CLONING® Kit, to generate pAG77. The Thielavia terrestris gh61s insert was confirmed by DNA sequencing. E. coli pAG77 was deposited with the Agricultural Research Service Patent Culture Collection, Northern Regional Research Center, Peoria, Ill., USA, on Sep. 18, 2009 and assigned accession number NRRL B-50324.

Example 28: Characterization of the Thielavia terrestris Genomic Sequence Encoding a Family GH61S Polypeptide Having Cellulolytic Enhancing Activity The nucleotide sequence (SEQ ID NO: 17) and deduced amino acid sequence (SEQ ID NO: 18) of the Thielavia terrestris GH61S polypeptide having cellulolytic enhancing activity are shown in FIG. 13. The genomic polynucleotide is 1584 bp, including the stop codon, and the coding sequence is interrupted by two introns of 64 and 83 bp. The predicted coding sequence encodes a polypeptide of 478 amino acids. The % G+C content of the full-length coding sequence (including introns) and the mature coding sequence is 63.9% and 64.0%, respectively. Using the SignalP software program (Nielsen et al., 1997, supra), a signal peptide was predicted but its exact location was ambiguous. The vast majority of GH61 mature polypeptides begin with a histidine residue, and therefore the most likely signal peptide is from residues 1 to 22. The predicted mature protein contains 456 amino acids with a molecular mass of 48.7 kDa.

Analysis of the deduced amino acid sequence of the GH61S polypeptide having cellulolytic enhancing activity with the Interproscan program (Mulder et al., 2007, supra) showed that the GH61S polypeptide contained the sequence signature of glycoside hydrolase Family 61 (InterPro accession IPR005103). This sequence signature was found from approximately residues 108 to 222 of the mature polypeptide (Pfam accession PF03443).

A comparative pair wise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Thielavia terrestris* GH61S mature polypeptide shares 65.1% identity (excluding gaps) to the deduced amino acid sequence of another predicted Family 61 glycoside hydrolase protein from *Chaetomium globosum* (UniProt accession number Q2GZM2).

Example 29: Construction of an *Aspergillus oryzae* Expression Vector for the *Thielavia terrestris* Family GH61T Gene Two synthetic oligonucleotide primers shown below were designed to PCR amplify the *Thielavia terrestris* Family GH61T gene from the genomic DNA prepared in Example 2. An IN-FUSION™ Cloning Kit was used to clone the fragment directly into the expression vector, pAILo2, without the need for restriction digests and ligation.
Forward Primer:

(SEQ ID NO: 41)
5'-ACTGGATTTACCATGCAGCTCCTCGTGGGCTT-3'

Reverse Primer:

(SEQ ID NO: 42)
5'-TCACCTCTAGTTAATTAATCAGCCACTCCACACCGGCG-3'

Bold letters represent coding sequence. The remaining sequence is homologous to the insertion sites of pAILo2.

Fifty picomoles of each of the primers above were used in a PCR reaction containing 1 μg of *Thielavia terrestris* genomic DNA, 1× ADVANTAGE® GC-Melt LA Buffer, 1 μl of 10 mM blend of dATP, dTTP, dGTP, and dCTP, and 1.25 units of ADVANTAGE® GC Genomic LA Polymerase Mix, in a final volume of 25 μl. The amplification conditions were one cycle at 94° C. for 1 minute; and 30 cycles each at 94° C. for 30 seconds, 60.5° C. for 30 seconds, and 72° C. for 1.5 minutes. The heat block was then held at 72° C. for 5 minutes followed by a 4° C. soak cycle.

The reaction products were isolated on a 1.0% agarose gel using TAE buffer where as approximately 900 bp product band was excised from the gel and purified using a MINELUTE® Gel Extraction Kit according to the manufacturer's instructions.

The fragment was then cloned into pAILo2 using an IN-FUSION™ Cloning Kit. The vector was digested with Nco I and Pac I. The fragment was purified by gel electrophoresis and QIAQUICK® Gel Extraction Kit. The gene fragment and the digested vector were combined together in a reaction resulting in the expression plasmid pAG73, in which transcription of the Family GH61T gene was under the control of the NA2-tpi promoter. The recombination reaction (10 μl) was composed of 1×IN-FUSION™ Buffer, 1×BSA, 0.5 μl of IN-FUSION™ enzyme (diluted 1:10), 93 ng of pAILo2 digested with Nco I and Pac I, and 2 μl of the *Thielavia terrestris* GH61T purified PCR product. The reaction was incubated at 37° C. for 15 minutes followed by 15 minutes at 50° C. The reaction was diluted with 40 μl of TE buffer and 2.5 μl of the diluted reaction was used to transform *E. coli* Top10 Competent cells. An *E. coli* transformant containing pAG73 (GH61T gene) was identified by restriction enzyme digestion and plasmid DNA was prepared using a BIOROBOT® 9600.

The same 900 bp *Thielavia terrestris* gh61t PCR fragment was also cloned into pCR®2.1-TOPO vector using a TOPO® TA CLONING® Kit, to generate pAG78. The *Thielavia terrestris* gh61t insert was confirmed by DNA sequencing. *E. coli* pAG78 was deposited with the Agricultural Research Service Patent Culture Collection, Northern Regional Research Center, Peoria, Ill., USA, on Sep. 18, 2009 and assigned accession number NRRL B-50325.

Example 30: Characterization of the *Thielavia terrestris* Genomic Sequence Encoding a Family GH61T Polypeptide Having Cellulolytic Enhancing Activity The nucleotide sequence (SEQ ID NO: 19) and deduced amino acid sequence (SEQ ID NO: 20) of the *Thielavia terrestris* GH61T polypeptide having cellulolytic enhancing activity are shown in FIG. 14. The genomic polynucleotide is 868 bp, including the stop codon, and the coding sequence is interrupted by two introns of 76 and 99 bp. The predicted coding sequence encodes a polypeptide of 230 amino acids. The % G+C content of the full-length coding sequence (including introns) and the mature coding sequence is 61.5% and 61.4%, respectively. Using the SignalP software program (Nielsen et al., 1997, supra), a signal peptide of 16 residues was predicted. The predicted mature protein contains 214 amino acids with a molecular mass of 23.1 kDa.

Analysis of the deduced amino acid sequence of the GH61T polypeptide having cellulolytic enhancing activity with the Interproscan program (Mulder et al., 2007, supra) showed that the GH61T polypeptide contained the sequence signature of glycoside hydrolase Family 61 (InterPro accession IPR005103). This sequence signature was found from approximately residues 71 to 197 of the mature polypeptide (Pfam accession PF03443).

A comparative pair wise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Thielavia terrestris* GH61T mature polypeptide shares 87.4% identity (excluding gaps) to the deduced amino acid sequence of another predicted Family 61 glycoside hydrolase protein from *Chaetomium globosum* (UniProt accession number Q2GUT0).

Example 31: Construction of an *Aspergillus oryzae* Expression Vector for the *Thielavia terrestris* Family GH61U Gene Two synthetic oligonucleotide primers shown below were designed to PCR amplify the *Thielavia terrestris* Family GH61U gene from the genomic DNA prepared in Example 2. An IN-FUSION™ Cloning Kit was used to clone the fragment directly into the expression vector, pAILo2, without the need for restriction digests and ligation.
Forward Primer:

(SEQ ID NO: 43)
5'-ACTGGATTTACCATGAAGCTGTACCTGGCGGCCTTT-3'

Reverse Primer:

(SEQ ID NO: 44)
5'-TCACCTCTAGTTAATTAATCAACCAGTCCACAGCGCTG-3'

Bold letters represent coding sequence. The remaining sequence is homologous to the insertion sites of pAILo2.

Fifty picomoles of each of the primers above were used in a PCR reaction containing 1 µg of *Thielavia terrestris* genomic DNA, 1× ADVANTAGE® GC-Melt LA Buffer, 1 µl of 10 mM blend of dATP, dTTP, dGTP, and dCTP, and 1.25 units of ADVANTAGE® GC Genomic LA Polymerase Mix, in a final volume of 25 µl. The amplification conditions were one cycle at 94° C. for 1 minute; and 30 cycles each at 94° C. for 30 seconds, 58.5° C. for 30 seconds, and 72° C. for 1.5 minutes. The heat block was then held at 72° C. for 5 minutes followed by a 4° C. soak cycle.

The reaction products were isolated on a 1.0% agarose gel using TAE buffer where as approximately 1 kb product band was excised from the gel and purified using a MINELUTE® Gel Extraction Kit according to the manufacturer's instructions.

The fragment was then cloned into pAILo2 using an IN-FUSION™ Cloning Kit. The vector was digested with Nco I and Pac I. The fragment was purified by gel electrophoresis and QIAQUICK® Gel Extraction Kit. The gene fragment and the digested vector were combined together in a reaction resulting in the expression plasmid pAG74, in which transcription of the Family GH61U gene was under the control of the NA2-tpi promoter. The recombination reaction (10 µl) was composed of 1×IN-FUSION™ Buffer, 1×BSA, 0.5 µl of IN-FUSION™ enzyme (diluted 1:10), 93 ng of pAILo2 digested with Nco I and Pac I, and 2 µl of the *Thielavia terrestris* GH61U purified PCR product. The reaction was incubated at 37° C. for 15 minutes followed by 15 minutes at 50° C. The reaction was diluted with 40 µl of TE buffer and 2.5 µl of the diluted reaction was used to transform *E. coli* Top10 Competent cells. An *E. coli* transformant containing pAG74 (GH61U gene) was identified by restriction enzyme digestion and plasmid DNA was prepared using a BIOROBOT® 9600.

The same 1 kb *Thielavia terrestris* gh61u PCR fragment was also cloned into pCR®2.1-TOPO vector using a TOPO® TA CLONING® Kit, to generate pAG79. The *Thielavia terrestris* gh61juinsert was confirmed by DNA sequencing. *E. coli* pAG79 was deposited with the Agricultural Research Service Patent Culture Collection, Northern Regional Research Center, Peoria, Ill., USA, on Sep. 18, 2009 and assigned accession number NRRL B-50326.

Example 32: Characterization of the *Thielavia terrestris* Genomic Sequence Encoding a Family GH61U Polypeptide Having Cellulolytic Enhancing Activity The nucleotide sequence (SEQ ID NO: 21) and deduced amino acid sequence (SEQ ID NO: 22) of the *Thielavia terrestris* GH61U polypeptide having cellulolytic enhancing activity are shown in FIG. 15. The genomic polynucleotide is 1068 bp, including the stop codon, and the coding sequence is interrupted by four introns of 64, 52, 96 and 82 bp. The predicted coding sequence encodes a polypeptide of 257 amino acids. The % G+C content of the full-length coding sequence (including introns) and the mature coding sequence is 59.7% and 59.3%, respectively. Using the SignalP software program (Nielsen et al., 1997, supra), a signal peptide of 19 residues was predicted. The predicted mature protein contains 238 amino acids with a molecular mass of 26.6 kDa.

Analysis of the deduced amino acid sequence of the GH61U polypeptide having cellulolytic enhancing activity with the Interproscan program (Mulder et al., 2007, supra) failed to show that the GH61U polypeptide contained the sequence signature of glycoside hydrolase Family 61 (InterPro accession IPR005103). However, a direct search against the Pfam database produced a significant hit (e value of $4.3 \times 10^{-8}$) to the GH61 family (Pfam accession PF03443). A comparative pair wise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Thielavia terrestris* GH61U mature polypeptide shares 74.4% identity (excluding gaps) to the deduced amino acid sequence of another predicted Family 61 glycoside hydrolase protein from *Chaetomium globosum* (UniProt accession number Q2HHT1).

Deposits of Biological Material

The following biological materials have been deposited under the terms of the Budapest Treaty with Agricultural Research Service Patent Culture Collection (NRRL), Northern Regional Research Center, 1815 University Street, Peoria, Ill., USA, and given the following accession numbers:

| Deposit | Accession Number | Date of Deposit |
| --- | --- | --- |
| *E. coli* (pSMai216) | NRRL B-50301 | Aug. 3, 2009 |
| *E. coli* (pSMai217) | NRRL B-50302 | Aug. 3, 2009 |
| *E. coli* (pSMai218) | NRRL B-50303 | Aug. 3, 2009 |
| *E. coli* (pSMai213) | NRRL B-50300 | Aug. 3, 2009 |
| *E. coli* (pAG68) | NRRL B-50320 | Sep. 18, 2009 |
| *E. coli* (pAG69) | NRRL B-50321 | Sep. 18, 2009 |
| *E. coli* (pAG75) | NRRL B-50322 | Sep. 18, 2009 |
| *E. coli* (pAG76) | NRRL B-50323 | Sep. 18, 2009 |
| *E. coli* (pAG77) | NRRL B-50324 | Sep. 18, 2009 |
| *E. coli* (pAG78) | NRRL B-50325 | Sep. 18, 2009 |
| *E. coli* (pAG79) | NRRL B-50326 | Sep. 18, 2009 |

The strains have been deposited under conditions that assure that access to the cultures will be available during the pendency of this patent application to one determined by foreign patent laws to be entitled thereto. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A DNA construct or recombinant expression vector comprising an isolated polynucleotide comprising a nucleotide sequence that encodes a GH61 polypeptide having cellulolytic enhancing activity, wherein the isolated polynucleotide is operably linked to one or more heterologous control sequences that direct the production of the GH61 polypeptide in an expression host, and wherein the GH61 polypeptide having cellulolytic enhancing activity is selected from the group consisting of:
   (a) a GH61 polypeptide having at least 95% sequence identity to amino acids 18 to 227 of SEQ ID NO: 6; and
   (b) a GH61 polypeptide encoded by a polynucleotide having at least 99% sequence identity to nucleotides 52 to 795 of SEQ ID NO: 5, or a GH61 polypeptide encoded by the cDNA of nucleotides 52 to 795 of SEQ ID NO: 5.

2. The DNA construct or recombinant expression vector of claim 1, wherein the GH61 polypeptide has at least 96% sequence identity to amino acids 18 to 227 of SEQ ID NO: 6.

3. The DNA construct or recombinant expression vector of claim 1, wherein the GH61 polypeptide has at least 97% sequence identity to amino acids 18 to 227 of SEQ ID NO: 6.

4. The DNA construct or recombinant expression vector of claim 1, wherein the GH61 polypeptide has at least 98% sequence identity to amino acids 18 to 227 of SEQ ID NO: 6.

5. The DNA construct or recombinant expression vector of claim 1, wherein the GH61 polypeptide has at least 99% sequence identity to amino acids 18 to 227 of SEQ ID NO: 6.

6. The DNA construct or recombinant expression vector of claim 1, wherein the GH61 polypeptide comprises amino acids 18 to 227 of SEQ ID NO: 6.

7. The DNA construct or recombinant expression vector of claim 1, wherein the GH61 polypeptide consists of amino acids 18 to 227 of SEQ ID NO: 6.

8. The DNA construct or recombinant expression vector of claim 1, wherein the GH61 polypeptide is encoded by a polynucleotide comprising nucleotides 52 to 795 of SEQ ID NO: 5, or the cDNA of nucleotides 52 to 795 of SEQ ID NO: 5.

9. The DNA construct or recombinant expression vector of claim 1, wherein the GH61 polypeptide is encoded by a polynucleotide consisting of nucleotides 52 to 795 of SEQ ID NO: 5, or the cDNA of nucleotides 52 to 795 of SEQ ID NO: 5.

10. The DNA construct or recombinant expression vector of claim 1, wherein the GH61 polypeptide is encoded by nucleotides 52 to 795 of SEQ ID NO: 5 contained in pSMai218 which is contained in *E. coli* NRRL B-50303 deposited with the Northern Regional Research Center of the Agriculture Research Service Patent Culture Collection.

11. A recombinant host cell comprising the DNA construct or recombinant expression vector of claim 1.

12. A method of producing a GH61 polypeptide having cellulolytic enhancing activity, said method comprising:
   (a) cultivating the recombinant host cell of claim 11 under conditions conducive for production of the GH61 polypeptide; and
   (b) recovering the GH61 polypeptide.

13. A DNA construct comprising a nucleic acid encoding a signal peptide comprising amino acids 1 to 17 of SEQ ID NO: 6, wherein the nucleic acid is operably linked to a heterologous nucleic acid encoding a protein.

14. A recombinant host cell comprising a nucleic acid encoding a protein, wherein the nucleic acid is operably linked to an isolated polynucleotide encoding a signal peptide comprising amino acids 1 to 17 of SEQ ID NO: 6, wherein the nucleic acid is foreign to the polynucleotide encoding the signal peptide.

15. A method of producing a protein, said method comprising:
   (a) cultivating the recombinant host cell of claim 14 under conditions conducive for production of the protein; and
   (b) recovering the protein.

16. A transgenic plant, plant part or plant cell transformed with a polynucleotide encoding a GH61 polypeptide having cellulolytic enhancing activity, wherein the GH61 polypeptide comprises a signal peptide directing the GH61 polypeptide into the secretory pathway, and wherein the GH61 polypeptide having cellulolytic enhancing activity is selected from the group consisting of:
   (a) a GH61 polypeptide having at least 95% sequence identity to amino acids 18 to 227 of SEQ ID NO: 6;
   (b) a GH61 polypeptide encoded by a polynucleotide having at least 99% sequence identity to nucleotides 52 to 795 of SEQ ID NO: 5, or a GH61 polypeptide encoded by the cDNA of nucleotides 52 to 795 of SEQ ID NO: 5;
   (c) a GH61 polypeptide comprising amino acids 18 to 227 of SEQ ID NO: 6.

17. A method of producing a GH61 polypeptide having cellulolytic enhancing activity, said method comprising:
   (a) cultivating the transgenic plant or plant cell of claim 16 under conditions conducive for production of the GH61 polypeptide; and
   (b) recovering the GH61 polypeptide.

18. A method for degrading a cellulosic material comprising:
   (i) treating the cellulosic material with an enzyme composition comprising a GH61 having cellulolytic enhancing activity, and
   (ii) recovering the degraded cellulosic material;
   wherein the GH61 polypeptide having cellulolytic enhancing activity is selected from the group consisting of:
   (a) a GH61 polypeptide having at least 95% sequence identity to amino acids 18 to 227 of SEQ ID NO: 6; and
   (b) a GH61 polypeptide encoded by a polynucleotide having at least 99% sequence identity to nucleotides 52 to 795 of SEQ ID NO: 5, or a GH61 polypeptide encoded by the cDNA of nucleotides 52 to 795 of SEQ ID NO: 5.

19. A method for producing a fermentation product, said method comprising:
   (i) saccharifying a cellulosic material with an enzyme composition comprising a GH61 polypeptide having cellulolytic enhancing activity;
   (ii) fermenting the saccharified cellulosic material with one or more fermenting microorganisms to produce the fermentation product; and
   (ii) recovering the fermentation product from the fermentation;
   wherein the GH61 polypeptide having cellulolytic enhancing activity is selected from the group consisting of:
   (a) a GH61 polypeptide having at least 95% sequence identity to amino acids 18 to 227 of SEQ ID NO: 6; and
   (b) a GH61 polypeptide encoded by a polynucleotide having at least 99% sequence identity to nucleotides 52 to 795 of SEQ ID NO: 5, or a GH61 polypeptide encoded by the cDNA of nucleotides 52 to 795 of SEQ ID NO: 5.

20. The method of claim 19, wherein steps (i) and (ii) are performed simultaneously.

21. A method of fermenting a cellulosic material comprising:
(i) fermenting the cellulosic material with one or more fermenting microorganisms, wherein the cellulosic material is saccharified with an enzyme composition comprising a GH61 polypeptide having cellulolytic enhancing activity, wherein the fermenting of the cellulosic material produces a fermentation product, and
(ii) recovering the fermentation product from the fermentation;
wherein the GH61 polypeptide having cellulolytic enhancing activity is selected from the group consisting of:
(a) a GH61 polypeptide having at least 95% sequence identity to amino acids 18 to 227 of SEQ ID NO: 6; and
(b) a GH61 polypeptide encoded by a polynucleotide having at least 99% sequence identity to nucleotides 52 to 795 of SEQ ID NO: 5, or a GH61 polypeptide encoded by the cDNA of nucleotides 52 to 795 of SEQ ID NO: 5.

22. The method of claim 18, wherein the GH61 polypeptide comprises amino acids 18 to 227 of SEQ ID NO: 6.

23. The method of claim 19, wherein the GH61 polypeptide comprises amino acids 18 to 227 of SEQ ID NO: 6.

24. The method of claim 21, wherein the GH61 polypeptide comprises amino acids 18 to 227 of SEQ ID NO: 6.

25. The method of claim 18, wherein the GH61 polypeptide has at least 96% sequence identity to amino acids 18 to 227 of SEQ ID NO: 6.

26. The method of claim 18, wherein the GH61 polypeptide has at least 97% sequence identity to amino acids 18 to 227 of SEQ ID NO: 6.

27. The method of claim 18, wherein the GH61 polypeptide has at least 98% sequence identity to amino acids 18 to 227 of SEQ ID NO: 6.

28. The method of claim 18, wherein the GH61 polypeptide has at least 99% sequence identity to amino acids 18 to 227 of SEQ ID NO: 6.

29. The method of claim 19, wherein the GH61 polypeptide has at least 96% sequence identity to amino acids 18 to 227 of SEQ ID NO: 6.

30. The method of claim 19, wherein the GH61 polypeptide has at least 97% sequence identity to amino acids 18 to 227 of SEQ ID NO: 6.

31. The method of claim 19, wherein the GH61 polypeptide has at least 98% sequence identity to amino acids 18 to 227 of SEQ ID NO: 6.

32. The method of claim 19, wherein the GH61 polypeptide has at least 99% sequence identity to amino acids 18 to 227 of SEQ ID NO: 6.

33. The method of claim 21, wherein the GH61 polypeptide has at least 96% sequence identity to amino acids 18 to 227 of SEQ ID NO: 6.

34. The method of claim 21, wherein the GH61 polypeptide has at least 97% sequence identity to amino acids 18 to 227 of SEQ ID NO: 6.

35. The method of claim 21, wherein the GH61 polypeptide has at least 98% sequence identity to amino acids 18 to 227 of SEQ ID NO: 6.

36. The method of claim 21, wherein the GH61 polypeptide has at least 99% sequence identity to amino acids 18 to 227 of SEQ ID NO: 6.

\* \* \* \* \*

SEQUENCE LISTING

<160> NUMBER OF SEQ ID NOS: 44

<210> SEQ ID NO 1
<211> LENGTH: 878
<212> TYPE: DNA
<213> ORGANISM: Thielavia terrestris

<400> SEQUENCE: 1

```
atgaagttct cactggtgtc tctgctggct tacggcctct cggtcgaggc gcactccatc    60
ttccaggttc gtctcgcaca tcacgctcaa ctcggctcgt ggcgtaaggg caaggattaa   120
cacggccggc agagagtctc ggtcaacggc caagaccaag gcctgctcac cggcctccgc   180
gctccaagca acaacaaccc agtgcaagat gtcaacagcc agaacatgat ttgcggccag   240
tcgggctcca agtcgcagac cgttatcaac gtcaaggccg gcgacaggat cggctcgctc   300
tggcagcatg tcatcggcgg cgcccagttt cgggtgacc cggacaaccc gatcgcccac   360
tcgcacaagg gccccgtgat ggcgtacctt gctaaggtcg acaatgccgc gtccgcgagc   420
caaacgggtc tgaagtggta agtagcgggc gacgctcagg ggacggggat cggggggcctg   480 ctccatccga gactaacacc gtggacaggt tcaagatctg gcaggacggg ttcgatacca   540
gcagcaagac atggggcgtc gacaacctga tcaagaacaa cggctgggtg tacttccacc   600
tgccgcagtg cctcgctccg ggccagtatc tcctgcgcgt cgaggttctg gcgctgcact   660
cggcgtacca gcagggccag gcccagttct accagtcctg cgcccagatc aacgtctccg   720
gctccgggtc cttcagcccg tcccagacgg tcagcatccc gggcgtctac agcgccaccg   780
acccgagcat cctcatcaac atctacggca gcacggggca gcccgacaac ggcggcaagg   840
cttacaaccc ccctggaccc gccccgatct cctgctga                           878
```

<210> SEQ ID NO 2
<211> LENGTH: 246
<212> TYPE: PRT
<213> ORGANISM: Thielavia terrestris

<400> SEQUENCE: 2

```
Met Lys Phe Ser Leu Val Ser Leu Leu Ala Tyr Gly Leu Ser Val Glu
1               5                   10                  15

Ala His Ser Ile Phe Gln Arg Val Ser Val Asn Gly Gln Asp Gln Gly
            20                  25                  30

Leu Leu Thr Gly Leu Arg Ala Pro Ser Asn Asn Pro Val Gln Asp
        35                  40                  45

Val Asn Ser Gln Asn Met Ile Cys Gly Gln Ser Gly Ser Lys Ser Gln
    50                  55                  60

Thr Val Ile Asn Val Lys Ala Gly Asp Arg Ile Gly Ser Leu Trp Gln
65                  70                  75                  80

His Val Ile Gly Gly Ala Gln Phe Ser Gly Asp Pro Asp Asn Pro Ile
                85                  90                  95

Ala His Ser His Lys Gly Pro Val Met Ala Tyr Leu Ala Lys Val Asp
```

|    |    |    |    |    |    |    |    |    |    |    |    |    |
|---|---|---|---|---|---|---|---|---|---|---|---|---|
|    |    |    | 100 |    |    |    | 105 |    |    |    | 110 |    |
| Asn | Ala | Ala | Ser | Ala | Ser | Gln | Thr | Gly | Leu | Lys | Trp | Phe | Lys | Ile | Trp |
|    |    |    | 115 |    |    |    | 120 |    |    |    | 125 |    |

Gln Asp Gly Phe Asp Thr Ser Ser Lys Thr Trp Gly Val Asp Asn Leu
    130                 135                 140

Ile Lys Asn Asn Gly Trp Val Tyr Phe His Leu Pro Gln Cys Leu Ala
145                 150                 155                 160

Pro Gly Gln Tyr Leu Leu Arg Val Glu Val Leu Ala Leu His Ser Ala
                165                 170                 175

Tyr Gln Gln Gly Gln Ala Gln Phe Tyr Gln Ser Cys Ala Gln Ile Asn
                180                 185                 190

Val Ser Gly Ser Gly Ser Phe Ser Pro Ser Gln Thr Val Ser Ile Pro
                195                 200                 205

Gly Val Tyr Ser Ala Thr Asp Pro Ser Ile Leu Ile Asn Ile Tyr Gly
                210                 215                 220

Ser Thr Gly Gln Pro Asp Asn Gly Gly Lys Ala Tyr Asn Pro Pro Gly
225                 230                 235                 240

Pro Ala Pro Ile Ser Cys
                245

<210> SEQ ID NO 3
<211> LENGTH: 1253
<212> TYPE: DNA
<213> ORGANISM: Thielavia terrestris

<400> SEQUENCE: 3

```
atgaggacga cattcgccgc cgcgttggca gccttcgctg cgcaggaagt ggcaggccat      60
gccatcttcc aacagctctg ggtggacggc accgactata tacgtgctcc ccttttcctt     120
ttgtgtttgc ccatcctcga ttgataaccc gaggccatcc aatgctgact cttacagcac     180
ggctcctcct gcgtccgcat gccgctgtcg aactcgcccg tcacgaacgt cggcagcagg     240
gacatgatct gcaacgccgg cacgcgcccc gtcagcggga agtgccccgt caaggccggc     300
ggcaccgtga cggttgagat gcaccaggtg ggctgatttc ctgagcgtcc tattcctccc     360
ggaagcccct ttcccatcct tgccctggc taaccccctcc gccctccca gcaacccggg     420 gatcggtcgt gtaacaacga agccatcggc ggcgcccact ggggaccggt gcaggtgtac     480
ctcagcaagg tggaggacgc gagcacgcg gacgggtcga cgggctggtt caagatcttc     540
gcggacacgt ggtccaagaa ggcgggcagc tcggtggggg acgacgacaa ctggggcacg     600
cgcgacctca cgcgtgctg cggcaagatg caggtcaaga tcccggcgga catcccgtcg     660
ggcgactacc tgctgcgggc ggaggcgctg cgctgcaca cggcgggcca ggtgggcggc     720
gcgcagttct acatgagctg ctaccagatc accgtgtcgg gcggcggcag cgccagcccg     780
gccaccgtca agttccccgg cgcctacagc gccaacgacc cgggcatcca catcaacatc     840
cacgcggccg tgtccaacta cgtcgcgccc ggccgcgcg tctattccgg cggcacgacc     900
aaggtggccg gtccgggtg ccaaggctgc gagaacacgt gcaaggtcgg ctcgtcgccc     960
acggcgacgg cgccgtcggg caagagcggc gcgggttccg acggcggcgc tgggaccgac    1020
ggcgggtctt cgtcttcgag ccccgacacg ggcagcgcgt gcagcgtgca ggcctacggg    1080
cagtgcggcg ggaacgggta ctcgggttgc acccagtgcg cggtaagttc ggggtcgtct    1140
gtcttttgta ggaacatccg agaggcttgg ctgacgaggc gttgttgtag cccggctata    1200
cttgcaaggc ggtctctccg ccgtactatt cgcagtgcgc cccttcttct tag           1253
```

<210> SEQ ID NO 4
<211> LENGTH: 334
<212> TYPE: PRT
<213> ORGANISM: Thielavia terrestris

<400> SEQUENCE: 4

Met Arg Thr Thr Phe Ala Ala Leu Ala Ala Phe Ala Ala Gln Glu
1               5                   10                  15

Val Ala Gly His Ala Ile Phe Gln Gln Leu Trp His Gly Ser Ser Cys
            20                  25                  30

Val Arg Met Pro Leu Ser Asn Ser Pro Val Thr Asn Val Gly Ser Arg
        35                  40                  45

Asp Met Ile Cys Asn Ala Gly Thr Arg Pro Val Ser Gly Lys Cys Pro
    50                  55                  60

Val Lys Ala Gly Gly Thr Val Thr Val Glu Met His Gln Pro Gly
65                  70                  75                  80

Asp Arg Ser Cys Asn Asn Glu Ala Ile Gly Gly Ala His Trp Gly Pro
                85                  90                  95

Val Gln Val Tyr Leu Ser Lys Val Glu Asp Ala Ser Thr Ala Asp Gly
            100                 105                 110

Ser Thr Gly Trp Phe Lys Ile Phe Ala Asp Thr Trp Ser Lys Lys Ala
        115                 120                 125

Gly Ser Ser Val Gly Asp Asp Asn Trp Gly Thr Arg Asp Leu Asn
130                 135                 140

Ala Cys Cys Gly Lys Met Gln Val Lys Ile Pro Ala Asp Ile Pro Ser
145                 150                 155                 160

Gly Asp Tyr Leu Leu Arg Ala Glu Ala Leu Ala Leu His Thr Ala Gly
                165                 170                 175

Gln Val Gly Gly Ala Gln Phe Tyr Met Ser Cys Tyr Gln Ile Thr Val
            180                 185                 190

Ser Gly Gly Gly Ser Ala Ser Pro Ala Thr Val Lys Phe Pro Gly Ala
        195                 200                 205

Tyr Ser Ala Asn Asp Pro Gly Ile His Ile Asn Ile His Ala Ala Val
    210                 215                 220

Ser Asn Tyr Val Ala Pro Gly Pro Ala Val Tyr Ser Gly Gly Thr Thr
225                 230                 235                 240

Lys Val Ala Gly Ser Cys Gln Gly Cys Glu Asn Thr Cys Lys Val
                245                 250                 255

Gly Ser Ser Pro Thr Ala Thr Ala Pro Ser Gly Lys Ser Gly Ala Gly
            260                 265                 270

Ser Asp Gly Gly Ala Gly Thr Asp Gly Gly Ser Ser Ser Ser Pro
        275                 280                 285

Asp Thr Gly Ser Ala Cys Ser Val Gln Ala Tyr Gly Gln Cys Gly Gly
    290                 295                 300

Asn Gly Tyr Ser Gly Cys Thr Gln Cys Ala Pro Gly Tyr Thr Cys Lys
305                 310                 315                 320

Ala Val Ser Pro Pro Tyr Tyr Ser Gln Cys Ala Pro Ser Ser
                325                 330

<210> SEQ ID NO 5
<211> LENGTH: 798
<212> TYPE: DNA
<213> ORGANISM: Thielavia terrestris

<400> SEQUENCE: 5

-continued

```
atgaagctga gcgttgccat cgccgtgctg gcgtcggctc ttgccgaggc tcactgtgag      60
tgcatcgtct cactccagct actgcgaagc ttgctgacga tggtccctag acaccttccc     120
cagcatcgga aacaccgctg actggcagta tgtgcggatt acaacgaact accagagcaa     180
cgggccggtg acggacgtca cctcggatca aattcggtgc tacgaacgga acccaggcac     240
gggagcgcag ggcatataca acgtcaccgc cggccagacc atcaactaca acgcgaaggc     300
gtccatctcc cacccggggc ccatgtcctt ctacattgct aaggttcccg ccggccaaac     360
cgctgcgacc tgggacggta aggggggctgt gtggaccaag atctaccagg acatgcccaa     420
gttcggcagc agcctgacct ggcccaccat gggtaagaat tctcaccctg gaaatgaacg     480
cacatttgca cagatctaac atggcctaca ggcgccaagt ctgtcccgt caccatccct      540
cgttgcctcc agaacggcga ttaccttctg cgagccgagc acatcgctct acacagcgcg     600
agcagcgtcg gtggcgccca gttctacctc tcgtgcgccc agcttactgt cagcggcggc     660
agtggcacct ggaaccccaa gaaccgggtc tccttccccg gcgcttacaa ggcaacagac     720
ccgggcatct tgatcaacat ctactacccc gtgccgacca gctactcgcc gcccggcccg     780
ccggctgaga cgtgctaa                                                   798
```

<210> SEQ ID NO 6
<211> LENGTH: 227
<212> TYPE: PRT
<213> ORGANISM: Thielavia terrestris

<400> SEQUENCE: 6

```
Met Lys Leu Ser Val Ala Ile Ala Val Leu Ala Ser Ala Leu Ala Glu
1               5                   10                  15

Ala His Tyr Thr Phe Pro Ser Ile Gly Asn Thr Ala Asp Trp Gln Tyr
            20                  25                  30

Val Arg Ile Thr Thr Asn Tyr Gln Ser Asn Gly Pro Val Thr Asp Val
        35                  40                  45

Thr Ser Asp Gln Ile Arg Cys Tyr Glu Arg Asn Pro Gly Thr Gly Ala
    50                  55                  60

Gln Gly Ile Tyr Asn Val Thr Ala Gly Gln Thr Ile Asn Tyr Asn Ala
65                  70                  75                  80

Lys Ala Ser Ile Ser His Pro Gly Pro Met Ser Phe Tyr Ile Ala Lys
                85                  90                  95

Val Pro Ala Gly Gln Thr Ala Ala Thr Trp Asp Gly Lys Gly Ala Val
            100                 105                 110

Trp Thr Lys Ile Tyr Gln Asp Met Pro Lys Phe Gly Ser Ser Leu Thr
        115                 120                 125

Trp Pro Thr Met Gly Ala Lys Ser Val Pro Val Thr Ile Pro Arg Cys
    130                 135                 140

Leu Gln Asn Gly Asp Tyr Leu Leu Arg Ala Glu His Ile Ala Leu His
145                 150                 155                 160

Ser Ala Ser Ser Val Gly Gly Ala Gln Phe Tyr Leu Ser Cys Ala Gln
                165                 170                 175

Leu Thr Val Ser Gly Gly Ser Gly Thr Trp Asn Pro Lys Asn Arg Val
            180                 185                 190

Ser Phe Pro Gly Ala Tyr Lys Ala Thr Asp Pro Gly Ile Leu Ile Asn
        195                 200                 205

Ile Tyr Tyr Pro Val Pro Thr Ser Tyr Ser Pro Pro Gly Pro Pro Ala
    210                 215                 220

Glu Thr Cys
225
```

<210> SEQ ID NO 7
<211> LENGTH: 977
<212> TYPE: DNA
<213> ORGANISM: Thielavia terrestris

<400> SEQUENCE: 7

| | | | | | |
|---|---|---|---|---|---|
| atgaagctgt | catcccagct | cgccgccctc | acgctggccg | cggcctccgt | gtcaggccac | 60 |
| tacatcttcg | agcagattgc | ccatggcggc | accaagttcc | caccttacga | gtacatccga | 120 |
| agaaacacga | actataacag | ccctgtcacc | agtctctcgt | cgaacgacct | gcgatgcaac | 180 |
| gtaggcggcg | agacggctgg | caacacgacc | gtcctcgacg | tgaaggcggg | cgactccttc | 240 |
| accttctact | cggacgtggc | cgtgtaccac | caggggccca | tctcactgtg | cgtgccccgg | 300 |
| gccaactttg | atcagtccca | agcggactgt | ccgctcgcct | ggataaccac | aattgactga | 360 |
| cagcccgcac | agctacatgt | ccaaggctcc | cggctccgtc | gtggactacg | acggctccgg | 420 |
| cgactggttc | aagatccacg | actggggccc | gaccttcagc | aacggccagg | cctcgtggcc | 480 |
| gctgcggggt | gcgtcccttc | cctttccctc | cccttcctc  | cccttcctc  | cccccttc   | 540 |
| cccccttttc | tgtctggtcg | cacgcccgc  | tgacgtcccc | gtagacaact | accagtacaa | 600 |
| catcccgacg | tgcatcccga | acggcgagta | cctgctgcgc | atccagtcgc | tggcgatcca | 660 |
| caaccccggc | gccacgccgc | agttctacat | cagctgcgcg | caggtccggg | tctcgggcgg | 720 |
| cggcagcgcc | tcccccctccc | caacggccaa | gatccccggc | gcgttcaagg | cgaccgatcc | 780 |
| cgggtatacc | gcgaatgtga | gtgccctatg | ttccttgcgc | tccttgttcc | ttgctccttg | 840 |
| ctcggcgtgc | ttgaacgcta | cgggctgtgg | agggagggat | ggatggatga | ataggatgct | 900 |
| gactgatggt | gggacaccag | atttacaata | acttccactc | gtatacggtg | ccgggtccgg | 960 |
| cggtctttca | gtgctag    |            |            |            |            | 977 |

<210> SEQ ID NO 8
<211> LENGTH: 223
<212> TYPE: PRT
<213> ORGANISM: Thielavia terrestris

<400> SEQUENCE: 8

Met Lys Leu Ser Ser Gln Leu Ala Ala Leu Thr Leu Ala Ala Ala Ser
1               5                   10                  15

Val Ser Gly His Tyr Ile Phe Glu Gln Ile Ala His Gly Gly Thr Lys
            20                  25                  30

Phe Pro Pro Tyr Glu Tyr Ile Arg Arg Asn Thr Asn Tyr Asn Ser Pro
        35                  40                  45

Val Thr Ser Leu Ser Ser Asn Asp Leu Arg Cys Asn Val Gly Gly Glu
    50                  55                  60

Thr Ala Gly Asn Thr Thr Val Leu Asp Val Lys Ala Gly Asp Ser Phe
65                  70                  75                  80

Thr Phe Tyr Ser Asp Val Ala Val Tyr His Gln Gly Pro Ile Ser Leu
                85                  90                  95

Tyr Met Ser Lys Ala Pro Gly Ser Val Val Asp Tyr Asp Gly Ser Gly
            100                 105                 110

Asp Trp Phe Lys Ile His Asp Trp Gly Pro Thr Phe Ser Asn Gly Gln
        115                 120                 125

Ala Ser Trp Pro Leu Arg Asp Asn Tyr Gln Tyr Asn Ile Pro Thr Cys
    130                 135                 140

```
Ile Pro Asn Gly Glu Tyr Leu Leu Arg Ile Gln Ser Leu Ala Ile His
145                 150                 155                 160

Asn Pro Gly Ala Thr Pro Gln Phe Tyr Ile Ser Cys Ala Gln Val Arg
            165                 170                 175

Val Ser Gly Gly Gly Ser Ala Ser Pro Ser Pro Thr Ala Lys Ile Pro
        180                 185                 190

Gly Ala Phe Lys Ala Thr Asp Pro Gly Tyr Thr Ala Asn Ile Tyr Asn
    195                 200                 205

Asn Phe His Ser Tyr Thr Val Pro Gly Pro Ala Val Phe Gln Cys
    210                 215                 220

<210> SEQ ID NO 9
<211> LENGTH: 1107
<212> TYPE: DNA
<213> ORGANISM: Thielavia terrestris

<400> SEQUENCE: 9
atgccttctt tcgcctccaa gactctcctt tccaccctgg cgggtgccgc atccgtggcc      60
gcccacgggc acgtgtcgaa catcgtcatc aacggggtct cgtaccaggg ttacgatccg     120
acctccttcc cttacatgca gaacccgccc atcgtggtcg gctggactgc cgccgacacg     180
gacaacggct tgttgccccc ggatgccttc gccagtggcg atatcatctg ccacaagaac     240
gccaccaacg ccaagggcca cgccgtggtc gccgcgggag acaagatctt catccagtgg     300
aacacatggc ccgagtccca ccacggcccc gtcatcgact acctcgcgag ctgcggcagc     360
gcgtcctgcg agaccgtcga caagaccaag ctcgagttct tcaagatcga cgaggtcggc     420
ctggtcgacg gcagctcggc gcccggtgtg tggggctccg accagctcat cgccaacaac     480
aactcgtggc tcgtcgagat cccgcccacc atcgcgccgg caactacgt cctgcgccac      540 gagatcatcg cgctgcacag cgccgaaaac gccgacggcg cccagaacta cccgcagtgc     600
ttcaacctgc agatcaccgg caccggcacc gccaccccct ccggcgtccc cggcacctcg     660
ctctacaccc cgaccgaccc gggcatcctc gtcaacatct cagcgcccc gatcacctac      720 accgtcccgg ggccggccct catctccggc gccgtcagca tcgcccagtc ctcctccgcc     780
atcaccgcct ccggcaccgc cctgaccggc tctgccaccg cacccgccgc cgccgctgct     840
accacaactt ccaccaccaa cgccgcgggct gctgctacct gctgctgctg tgctgctggt    900
acttccacaa ccaccaccag cgccgcggcc gtggtccaga cctcctcctc ctcctcctcc    960
gccccgtcct tgccgccgc cgccgccacc accaccgcgg ctgccagcgc ccgcccgacc   1020
ggctgctcct ctggccgctc caggaagcag ccgcgccgcc acgcgcggga tatggtggtt    1080
gcgcgagggg ctgaggaggc aaactga                                         1107

<210> SEQ ID NO 10
<211> LENGTH: 368
<212> TYPE: PRT
<213> ORGANISM: Thielavia terrestris

<400> SEQUENCE: 10

Met Pro Ser Phe Ala Ser Lys Thr Leu Leu Ser Thr Leu Ala Gly Ala
1               5                   10                  15

Ala Ser Val Ala Ala His Gly His Val Ser Asn Ile Val Ile Asn Gly
            20                  25                  30

Val Ser Tyr Gln Gly Tyr Asp Pro Thr Ser Phe Pro Tyr Met Gln Asn
        35                  40                  45

Pro Pro Ile Val Val Gly Trp Thr Ala Ala Asp Thr Asp Asn Gly Phe
```

|       |       |       |       | 50    |       |       |       |       | 55    |       |       |       |       | 60    |       |       |
|-------|-------|-------|-------|-------|-------|-------|-------|-------|-------|-------|-------|-------|-------|-------|-------|-------|

Val Ala Pro Asp Ala Phe Ala Ser Gly Asp Ile Ile Cys His Lys Asn
 65                  70                  75                  80

Ala Thr Asn Ala Lys Gly His Ala Val Val Ala Gly Asp Lys Ile
                 85                  90                  95

Phe Ile Gln Trp Asn Thr Trp Pro Glu Ser His His Gly Pro Val Ile
            100                 105                 110

Asp Tyr Leu Ala Ser Cys Gly Ser Ala Ser Cys Glu Thr Val Asp Lys
            115                 120                 125

Thr Lys Leu Glu Phe Phe Lys Ile Asp Glu Val Gly Leu Val Asp Gly
            130                 135                 140

Ser Ser Ala Pro Gly Val Trp Gly Ser Asp Gln Leu Ile Ala Asn Asn
145                 150                 155                 160

Asn Ser Trp Leu Val Glu Ile Pro Pro Thr Ile Ala Pro Gly Asn Tyr
                165                 170                 175

Val Leu Arg His Glu Ile Ile Ala Leu His Ser Ala Glu Asn Ala Asp
                180                 185                 190

Gly Ala Gln Asn Tyr Pro Gln Cys Phe Asn Leu Gln Ile Thr Gly Thr
            195                 200                 205

Gly Thr Ala Thr Pro Ser Gly Val Pro Gly Thr Ser Leu Tyr Thr Pro
210                 215                 220

Thr Asp Pro Gly Ile Leu Val Asn Ile Tyr Ser Ala Pro Ile Thr Tyr
225                 230                 235                 240

Thr Val Pro Gly Pro Ala Leu Ile Ser Gly Ala Val Ser Ile Ala Gln
            245                 250                 255

Ser Ser Ser Ala Ile Thr Ala Ser Gly Thr Ala Leu Thr Gly Ser Ala
            260                 265                 270

Thr Ala Pro Ala Ala Ala Ala Thr Thr Ser Thr Thr Asn Ala
            275                 280                 285

Ala Ala Ala Thr Ser Ala Ala Ala Ala Gly Thr Ser Thr Thr
            290                 295                 300

Thr Thr Ser Ala Ala Val Val Gln Thr Ser Ser Ser Ser Ser
305                 310                 315                 320

Ala Pro Ser Ser Ala Ala Ala Ala Thr Thr Ala Ala Ala Ser
            325                 330                 335

Ala Arg Pro Thr Gly Cys Ser Ser Gly Arg Ser Arg Lys Gln Pro Arg
            340                 345                 350

Arg His Ala Arg Asp Met Val Val Ala Arg Gly Ala Glu Glu Ala Asn
            355                 360                 365

<210> SEQ ID NO 11
<211> LENGTH: 993
<212> TYPE: DNA
<213> ORGANISM: Thielavia terrestris

<400> SEQUENCE: 11

```
atgccgcccg cactccctca actcctaacc acggtcctga ccgccctcac cctcggttcc      60
accgccctcg cccactcaca cctcgcgtac attatcgtta acggcaagct ctaccagggc     120
ttcgacccgc gcccgcacca ggccaactac ccttcccggg tcgggtggtc caccggcgcc     180
gtcgacgacg gcttcgtcac gccggccaac tactccaccc cggacatcat tgccacatc      240 gccggcacca gccggccgg ccacgcgccc gtgcgcccgg cgaccgcat ccacgtccag       300 tggaacggct ggccggtcgg ccacatcggt cccgtgctgt cgtacctcgc cgctgcgag      360
```

```
tcggacacgg gctgcacggg ccagaacaag accgcgctgc ggtggaccaa gatcgacgac    420
tccagcccga ccatgcagaa cgtcgccggc gcgggcaccc agggcgaggg caccccggc    480 aagcgctggg ccaccgacgt gctgatcgcc gccaacaaca gctggcaggt cgccgtgccg    540
gcggggctgc cgaccggcgc gtacgtgctg cgcaacgaga tcatcgcgct gcactacgcg    600
gcgaggaaga acggggcgca gaactatccg ctctgcatga acctgtgggt ggacgccagt    660
ggtgataata gtagtgtggc tgcaacgacg gcggcggtga cggcgggggg tctgcagatg    720
gatgcgtatg acgcgcgcgg gttctacaag gagaacgatc cgggcgtgct ggtcaatgtc    780
acggccgcgc tgtcgtcgta tgtcgtgccc gggccgacgg tggcggcggg cgccacgccg    840
gtgccgtacg cgcagcagag cccgagcgtg tcgacggcgg cgggcacgcc cgtcgtcgtt    900
acaaggacta gcgagacggc gccgtacacg ggcgccatga cgccgacggt tgcggcgagg    960
atgaagggga gggggtatga tcggcggggt tag                                993
```

<210> SEQ ID NO 12  
<211> LENGTH: 330  
<212> TYPE: PRT  
<213> ORGANISM: Thielavia terrestris

<400> SEQUENCE: 12

```
Met Pro Pro Ala Leu Pro Gln Leu Leu Thr Thr Val Leu Thr Ala Leu
1               5                   10                  15

Thr Leu Gly Ser Thr Ala Leu Ala His Ser His Leu Ala Tyr Ile Ile
            20                  25                  30

Val Asn Gly Lys Leu Tyr Gln Gly Phe Asp Pro Arg Pro His Gln Ala
        35                  40                  45

Asn Tyr Pro Ser Arg Val Gly Trp Ser Thr Gly Ala Val Asp Asp Gly
    50                  55                  60

Phe Val Thr Pro Ala Asn Tyr Ser Thr Pro Asp Ile Ile Cys His Ile
65                  70                  75                  80

Ala Gly Thr Ser Pro Ala Gly His Ala Pro Val Arg Pro Gly Asp Arg
                85                  90                  95

Ile His Val Gln Trp Asn Gly Trp Pro Val Gly His Ile Gly Pro Val
            100                 105                 110

Leu Ser Tyr Leu Ala Arg Cys Glu Ser Asp Thr Gly Cys Thr Gly Gln
        115                 120                 125

Asn Lys Thr Ala Leu Arg Trp Thr Lys Ile Asp Asp Ser Ser Pro Thr
    130                 135                 140

Met Gln Asn Val Ala Gly Ala Gly Thr Gln Gly Glu Gly Thr Pro Gly
145                 150                 155                 160

Lys Arg Trp Ala Thr Asp Val Leu Ile Ala Ala Asn Asn Ser Trp Gln
                165                 170                 175

Val Ala Val Pro Ala Gly Leu Pro Thr Gly Ala Tyr Val Leu Arg Asn
            180                 185                 190

Glu Ile Ile Ala Leu His Tyr Ala Ala Arg Lys Asn Gly Ala Gln Asn
        195                 200                 205

Tyr Pro Leu Cys Met Asn Leu Trp Val Asp Ala Ser Gly Asp Asn Ser
    210                 215                 220

Ser Val Ala Ala Thr Thr Ala Val Thr Ala Gly Gly Leu Gln Met
225                 230                 235                 240

Asp Ala Tyr Asp Ala Arg Gly Phe Tyr Lys Glu Asn Asp Pro Gly Val
                245                 250                 255

Leu Val Asn Val Thr Ala Ala Leu Ser Ser Tyr Val Val Pro Gly Pro
```

```
                260                 265                 270
Thr Val Ala Ala Gly Ala Thr Pro Val Pro Tyr Ala Gln Gln Ser Pro
            275                 280                 285

Ser Val Ser Thr Ala Ala Gly Thr Pro Val Val Thr Arg Thr Ser
        290                 295                 300

Glu Thr Ala Pro Tyr Thr Gly Ala Met Thr Pro Thr Val Ala Ala Arg
305                 310                 315                 320

Met Lys Gly Arg Gly Tyr Asp Arg Arg Gly
                325                 330

<210> SEQ ID NO 13
<211> LENGTH: 1221
<212> TYPE: DNA
<213> ORGANISM: Thielavia terrestris

<400> SEQUENCE: 13
atgaagacat tcaccgccct cctggccgca gccggcctcg tcgccggcca tggatatgtc      60
gacaacgcca ccattggcgg ccagtttat caggtactct accgcttcac ccaaggtccg      120
ctggccacaa ctctataggt gtcataaatt aacaagccac cgtcccgcag ttctatcagg     180
tgtgctcgct accgaccatg tggtcccgtc tcagcaagcc actcacacgc ccatgatccc     240
ctagccttac gtcgacccgt atttagcaac cttggcacgt agtatttatt gtcccaaata     300
ttgagctgaa ctgcacctcc ctagaatccc gcggtgctaa cattctttca gcccgacagg     360
gtctctcgat ccatcccggg caacggcccg gtcacggacg tcactctcat cgacctgcag     420
tgcaacgcca attccacccc ggccaagctc acgccactg ccgctgccgg tcggacgtg      480 attctccgct ggacgctctg gcctgagtcg cacgttggcc ccgtcatcac ctacatggcc     540
cgctgccccg cacgggctg ccaggactgg atgccgggca cttcgtagga gcccatcttg      600
caccatatcc atttcaaccg ccacacgca ctgacccata tgtctgtcta cccctgcagt     660
gcggtctggt tcaagatcaa ggagggcggc gcgacggca cttccaacac ctgggccgac     720
gtacgtgtac ccgtcccag agagccaaag ccccccttc aacaaagcaa acatctcaat     780
agcccgagcc tacgcactaa cccctctcct tcccctcga aaacacagac cccgctgatg     840
acggcgccca cctcgtacac gtacacgatc ccctcctgcc tgaagaaggg ctactacctg     900
gtccgccacg agatcatcgc gctgcacgcc gcctacacct accccggcgc gcagttctac     960
ccgggctgcc accagctcaa cgtcacgggc ggcgggtcca ccgtaccgtc gagcggcctg    1020
gtggcctttc ccggggcgta caagggcagt gaccccggga ttacgtacga tgcgtataaa    1080
ggtgggttgg ctggttggcc caggtcttgg tgatggggga atgtggtgat gaggtttatt    1140
atttgggatc ccgtggctaa cgtaaccctg ggtgtagcgc aaacgtacca gattcctggg    1200
ccggcggtct ttacttgctg a                                              1221

<210> SEQ ID NO 14
<211> LENGTH: 236
<212> TYPE: PRT
<213> ORGANISM: Thielavia terrestris

<400> SEQUENCE: 14

Met Lys Thr Phe Thr Ala Leu Leu Ala Ala Ala Gly Leu Val Ala Gly
1               5                   10                  15

His Gly Tyr Val Asp Asn Ala Thr Ile Gly Gly Gln Phe Tyr Gln Asn
            20                  25                  30

Pro Ala Val Leu Thr Phe Phe Gln Pro Asp Arg Val Ser Arg Ser Ile
```

```
                35                  40                  45
Pro Gly Asn Gly Pro Val Thr Asp Val Thr Leu Ile Asp Leu Gln Cys
             50                  55                  60

Asn Ala Asn Ser Thr Pro Ala Lys Leu His Ala Thr Ala Ala Ala Gly
 65                  70                  75                  80

Ser Asp Val Ile Leu Arg Trp Thr Leu Trp Pro Glu Ser His Val Gly
                 85                  90                  95

Pro Val Ile Thr Tyr Met Ala Arg Cys Pro Asp Thr Gly Cys Gln Asp
            100                 105                 110

Trp Met Pro Gly Thr Ser Ala Val Trp Phe Lys Ile Lys Glu Gly Gly
        115                 120                 125

Arg Asp Gly Thr Ser Asn Thr Trp Ala Asp Thr Pro Leu Met Thr Ala
    130                 135                 140

Pro Thr Ser Tyr Thr Tyr Thr Ile Pro Ser Cys Leu Lys Lys Gly Tyr
145                 150                 155                 160

Tyr Leu Val Arg His Glu Ile Ile Ala Leu His Ala Ala Tyr Thr Tyr
                165                 170                 175

Pro Gly Ala Gln Phe Tyr Pro Gly Cys His Gln Leu Asn Val Thr Gly
            180                 185                 190

Gly Gly Ser Thr Val Pro Ser Ser Gly Leu Val Ala Phe Pro Gly Ala
        195                 200                 205

Tyr Lys Gly Ser Asp Pro Gly Ile Thr Tyr Asp Ala Tyr Lys Ala Gln
    210                 215                 220

Thr Tyr Gln Ile Pro Gly Pro Ala Val Phe Thr Cys
225                 230                 235

<210> SEQ ID NO 15
<211> LENGTH: 933
<212> TYPE: DNA
<213> ORGANISM: Thielavia terrestris

<400> SEQUENCE: 15
atggccttgc tgctcttggc aggcttggcc attctggccg gccggctca tgcccacggc    60 ggcctcgcca actacacagt gggcaacacc tggtataggg ggtgcgtaag gggggcaccg   120
acaacgcctg cttagtaact ccaccatttc gagcgggcta acaccgggcg cagctacgac   180
cccttcacgc cggcggccga ccagatcggc cagccgtgga tgatccaacg cgcgtgggac   240
tcgatcgacc cgatcttcag cgtcaacgac aaggcgctcg cctgcaacac cccggccacg   300
gcgccgacct cttacattcc catccgcgcg ggcgagaaca tcacggccgt gtactggtac   360
tggctgcacc cggtgggccc catgacggcg tggctggcgc ggtgcgacgg cgactgccgc   420
gacgccgacg tcaacgaggc gcgctggttc aagatctggg aggccggcct gctcagcggg   480
ccgaacctgg ccgagggcat gtggtaccag aaggcgttcc agaactggga cggcagcccg   540
gacctgtggc ccgtcacgat cccggccggg ctgaagagcg gcctgtacat gatccggcac   600
gagatcttgt cgatccacgt cgaggataaa ccgcagtttt atcccgagtg tgcgcatctg   660
aatgtgaccg ggggtgggga cctgctgccg cctgatgagt ttttggtgaa gttcccgggc   720
gcttacaaag aagatagtga gtgaaacgcg aagcttcggt agccattggg ttgcgctgat   780
ggaggttaga cccgtcgatc aagatcaata tctactcgga ccagtacgcc aatacaacgg   840
tgagtgtaac aggtcgagca aaaccaaaca gatgccgatg actgatgatc tcagaattac   900
acaattcccg gagggccgat atgggatggg tga                                933
```

<210> SEQ ID NO 16
<211> LENGTH: 250
<212> TYPE: PRT
<213> ORGANISM: Thielavia terrestris

<400> SEQUENCE: 16

```
Met Ala Leu Leu Leu Ala Gly Leu Ala Ile Leu Ala Gly Pro Ala
1               5                   10                  15

His Ala His Gly Gly Leu Ala Asn Tyr Thr Val Gly Asn Thr Trp Tyr
            20                  25                  30

Arg Gly Tyr Asp Pro Phe Thr Pro Ala Ala Asp Gln Ile Gly Gln Pro
        35                  40                  45

Trp Met Ile Gln Arg Ala Trp Asp Ser Ile Asp Pro Ile Phe Ser Val
    50                  55                  60

Asn Asp Lys Ala Leu Ala Cys Asn Thr Pro Ala Thr Ala Pro Thr Ser
65                  70                  75                  80

Tyr Ile Pro Ile Arg Ala Gly Glu Asn Ile Thr Ala Val Tyr Trp Tyr
                85                  90                  95

Trp Leu His Pro Val Gly Pro Met Thr Ala Trp Leu Ala Arg Cys Asp
            100                 105                 110

Gly Asp Cys Arg Asp Ala Asp Val Asn Glu Ala Arg Trp Phe Lys Ile
        115                 120                 125

Trp Glu Ala Gly Leu Leu Ser Gly Pro Asn Leu Ala Glu Gly Met Trp
    130                 135                 140

Tyr Gln Lys Ala Phe Gln Asn Trp Asp Gly Ser Pro Asp Leu Trp Pro
145                 150                 155                 160

Val Thr Ile Pro Ala Gly Leu Lys Ser Gly Leu Tyr Met Ile Arg His
                165                 170                 175

Glu Ile Leu Ser Ile His Val Glu Asp Lys Pro Gln Phe Tyr Pro Glu
            180                 185                 190

Cys Ala His Leu Asn Val Thr Gly Gly Gly Asp Leu Leu Pro Pro Asp
        195                 200                 205

Glu Phe Leu Val Lys Phe Pro Gly Ala Tyr Lys Glu Asp Asn Pro Ser
    210                 215                 220

Ile Lys Ile Asn Ile Tyr Ser Asp Gln Tyr Ala Asn Thr Thr Asn Tyr
225                 230                 235                 240

Thr Ile Pro Gly Gly Pro Ile Trp Asp Gly
                245                 250
```

<210> SEQ ID NO 17
<211> LENGTH: 1584
<212> TYPE: DNA
<213> ORGANISM: Thielavia terrestris

<400> SEQUENCE: 17

```
atgatgccgt cccttgttcg cttctcaatg ggtctggcga ccgccttcgc ctcgctgtcc    60
acagcacata ccgtcttcac cacgcttttc atcaacggcg tcgaccaagg ggacgggacc   120
tgcatccgca tggccaagaa gggcagcgtt tgcacccatc ccattgctgg tggcctcgac   180
agcccagaca tggcttgtgg tatgccctct gcgtttcccc tgcgagagct ttcctcgagc   240
taacccaatg ccgcgttgcc caggccgaga cggacaacaa gccgtggcat tcacctgccc   300
agccccggcg ggctccaagt tgagcttcga gttccgcatg tgggccgacg cctctcagcc   360
cggctctatc gacccatccc acctcggctc gacggcaatc tacctcaaac aagtctccaa   420
catcagctcc gactcggctg ccggccctgg ctggttcaag atctacgccg agggctacga   480
```

```
cacagccgcc aagaagtggg ccacagagaa gctcatcgac aacggcggcc tgctgagcat    540
cgagcttccg cccactctgc cggcgggata ctacctcgcc cgcagcgaga tcgtcaccat    600
ccagaacgtc accaacgacc acgtcgaccc gcagttctac gttggctgcg cacagctctt    660
cgtccagggg cctccgacca cccccaccgt cccgccagac agactcgtct ccatcccggg    720
ccacgtccat gcctccgacc cggggctgac cttcaacatc tggcgcgacg accctccaa    780 gacggcctac accgtcgtcg gcccggcccc cttctccccc accgccgccc caccccac    840 ctccaccaac accaacgggc agcaacaaca acaacagcaa caggcgataa agcagacgga    900
cggcgtgatc cccgccgact gccagctcaa gaacgccaac tggtgcggcg ccgaggtgcc    960
cgcgtacgcc gacgaggccg gctgctgggc gtcgtcggcc gactgcttcg cccagctgga    1020
cgcctgctac acgtcggcgc cgccacgggg cagccgcggc tgccggctgt gggaggactg    1080
gtgcaccggc attcagcagg gctgccgcgc ggggcggtgg cggggccgc cgcccttca    1140 tggggagggg gcagcagcgg aggtgtgaac ggttcgggga cgggtggcgg tggtggtggt    1200
ggtggtggtg gcactggctc ttcttcggct tctgccccga cggagacggc ctctgctggc    1260 cggggggggcg caagaatagc tgccgtggcc ggctgcggag cgggacagg agacatggtt    1320 gaagaggttt tcctcttta ttgggacgct tgcagcggct ggcgacggag ccgtggtggt    1380
ggttcgattc ttgcgaggct tatccttcat gtccttcttc cacttttgag accgaggcga    1440 gccccctcgag tccatttact tctcttccac ctgtacctca acttctgtta tccaggaacc    1500
agtggtttct ataatcgcct gagcattaaa ctaggcatat ggccaagcaa aatgtcgcct    1560
gatgtagcgc attacgtgaa ataa                                           1584
```

<210> SEQ ID NO 18
<211> LENGTH: 478
<212> TYPE: PRT
<213> ORGANISM: Thielavia terrestris

<400> SEQUENCE: 18

```
Met Met Pro Ser Leu Val Arg Phe Ser Met Gly Leu Ala Thr Ala Phe
1               5                   10                  15

Ala Ser Leu Ser Thr Ala His Thr Val Phe Thr Thr Leu Phe Ile Asn
            20                  25                  30

Gly Val Asp Gln Gly Asp Gly Thr Cys Ile Arg Met Ala Lys Lys Gly
        35                  40                  45

Ser Val Cys Thr His Pro Ile Ala Gly Gly Leu Asp Ser Pro Asp Met
    50                  55                  60

Ala Cys Gly Arg Asp Gly Gln Gln Ala Val Ala Phe Thr Cys Pro Ala
65                  70                  75                  80

Pro Ala Gly Ser Lys Leu Ser Phe Glu Phe Arg Met Trp Ala Asp Ala
                85                  90                  95

Ser Gln Pro Gly Ser Ile Asp Pro Ser His Leu Gly Ser Thr Ala Ile
            100                 105                 110

Tyr Leu Lys Gln Val Ser Asn Ile Ser Ser Asp Ser Ala Ala Gly Pro
        115                 120                 125

Gly Trp Phe Lys Ile Tyr Ala Glu Gly Tyr Asp Thr Ala Ala Lys Lys
    130                 135                 140

Trp Ala Thr Glu Lys Leu Ile Asp Asn Gly Gly Leu Leu Ser Ile Glu
145                 150                 155                 160

Leu Pro Pro Thr Leu Pro Ala Gly Tyr Tyr Leu Ala Arg Ser Glu Ile
                165                 170                 175
```

```
Val Thr Ile Gln Asn Val Thr Asn Asp His Val Asp Pro Gln Phe Tyr
            180                 185                 190

Val Gly Cys Ala Gln Leu Phe Val Gln Gly Pro Pro Thr Thr Pro Thr
        195                 200                 205

Val Pro Pro Asp Arg Leu Val Ser Ile Pro Gly His Val His Ala Ser
210                 215                 220

Asp Pro Gly Leu Thr Phe Asn Ile Trp Arg Asp Pro Ser Lys Thr
225                 230                 235                 240

Ala Tyr Thr Val Val Gly Pro Ala Pro Phe Ser Pro Thr Ala Ala Pro
                245                 250                 255

Thr Pro Thr Ser Thr Asn Thr Asn Gly Gln Gln Gln Gln Gln Gln Gln
            260                 265                 270

Gln Ala Ile Lys Gln Thr Asp Gly Val Ile Pro Ala Asp Cys Gln Leu
        275                 280                 285

Lys Asn Ala Asn Trp Cys Gly Ala Glu Val Pro Ala Tyr Ala Asp Glu
290                 295                 300

Ala Gly Cys Trp Ala Ser Ser Ala Asp Cys Phe Ala Gln Leu Asp Ala
305                 310                 315                 320

Cys Tyr Thr Ser Ala Pro Pro Thr Gly Ser Arg Gly Cys Arg Leu Trp
                325                 330                 335

Glu Asp Trp Cys Thr Gly Ile Gln Gln Gly Cys Arg Ala Gly Arg Trp
            340                 345                 350

Arg Gly Pro Pro Phe His Gly Glu Gly Ala Ala Ala Glu Thr Ala
        355                 360                 365

Ser Ala Gly Arg Gly Gly Ala Arg Ile Ala Ala Val Ala Gly Cys Gly
370                 375                 380

Gly Gly Thr Gly Asp Met Val Glu Glu Val Phe Leu Phe Tyr Trp Asp
385                 390                 395                 400

Ala Cys Ser Gly Trp Arg Arg Ser Arg Gly Gly Ser Ile Leu Ala
                405                 410                 415

Arg Leu Ile Leu His Val Leu Leu Pro Leu Leu Arg Pro Arg Arg Ala
            420                 425                 430

Pro Arg Val His Leu Leu Leu Phe His Leu Tyr Leu Asn Phe Cys Tyr
        435                 440                 445

Pro Gly Thr Ser Gly Phe Tyr Asn Arg Leu Ser Ile Lys Leu Gly Ile
450                 455                 460

Trp Pro Ser Lys Met Ser Pro Asp Val Ala His Tyr Val Lys
465                 470                 475

<210> SEQ ID NO 19
<211> LENGTH: 868
<212> TYPE: DNA
<213> ORGANISM: Thielavia terrestris

<400> SEQUENCE: 19
atgcagctcc tcgtgggctt gctgcttgca gccgtggctg ctcgagcaca ttgtatttct      60 accccttttcc gcgtgcctcc cagcctcaag gcaagaagac gcacgcagca gctaacggac    120
cctatcagac acatttccca gactcgtggt aaatgggcag cccgaggaca aggactggtc    180
ggttacgcgc atgaccaaga acgcgcagag caagcaggga gtccaggacc cgaccagtcc    240
cgacattcgc tgctacacgt cgcagacggc gcctaacgtg gctacggtcc ctgccggagc    300
caccgtccat tacatatcga ctcagcagat caaccacccg ggcccgacgc agtactacct    360
cgccaaggta ccggcggggt cgtcggccaa gacgtgggac gggtcagggg ccgtctggtt    420
```

```
caagatctcg accaccatgc cttacttgga caacaacaag cagcttgtct ggccgaatca      480
gagtaggaac aattcccgct ccaatcttcg atttggcctt gagctacggc cgattgcatg      540
ggagagaccg ttgactgacg gggcaaccca accttcatca gacacgtaca cgacggtcaa      600
cacgaccatc cccgccgata cgcccagtgg ggaatacctc ctccgggtcg agcagatcgc      660
gctgcacctg gcctcgcagc caacgggc tcagttctac ctggcctgct cgcagatcca       720
gattacgggc ggcggcaacg gcacgcccgg cccgctagtc gcgttgccgg gggcgtacaa      780
gagcaacgac ccgggcattt tggtcaacat ctactctatg cagcccggcg attacaagcc      840
gcccgggccg ccggtgtgga gtggctga                                         868
```

<210> SEQ ID NO 20
<211> LENGTH: 230
<212> TYPE: PRT
<213> ORGANISM: Thielavia terrestris

<400> SEQUENCE: 20

```
Met Gln Leu Leu Val Gly Leu Leu Leu Ala Ala Val Ala Ala Arg Ala
1               5                   10                  15

His Tyr Thr Phe Pro Arg Leu Val Val Asn Gly Gln Pro Glu Asp Lys
            20                  25                  30

Asp Trp Ser Val Thr Arg Met Thr Lys Asn Ala Gln Ser Lys Gln Gly
        35                  40                  45

Val Gln Asp Pro Thr Ser Pro Asp Ile Arg Cys Tyr Thr Ser Gln Thr
    50                  55                  60

Ala Pro Asn Val Ala Thr Val Pro Ala Gly Ala Thr Val His Tyr Ile
65                  70                  75                  80

Ser Thr Gln Gln Ile Asn His Pro Gly Pro Thr Gln Tyr Tyr Leu Ala
                85                  90                  95

Lys Val Pro Ala Gly Ser Ser Ala Lys Thr Trp Asp Gly Ser Gly Ala
            100                 105                 110

Val Trp Phe Lys Ile Ser Thr Thr Met Pro Tyr Leu Asp Asn Asn Lys
        115                 120                 125

Gln Leu Val Trp Pro Asn Gln Asn Thr Tyr Thr Thr Val Asn Thr Thr
    130                 135                 140

Ile Pro Ala Asp Thr Pro Ser Gly Glu Tyr Leu Leu Arg Val Glu Gln
145                 150                 155                 160

Ile Ala Leu His Leu Ala Ser Gln Pro Asn Gly Ala Gln Phe Tyr Leu
                165                 170                 175

Ala Cys Ser Gln Ile Gln Ile Thr Gly Gly Gly Asn Gly Thr Pro Gly
            180                 185                 190

Pro Leu Val Ala Leu Pro Gly Ala Tyr Lys Ser Asn Asp Pro Gly Ile
        195                 200                 205

Leu Val Asn Ile Tyr Ser Met Gln Pro Gly Asp Tyr Lys Pro Pro Gly
    210                 215                 220

Pro Pro Val Trp Ser Gly
225                 230
```

<210> SEQ ID NO 21
<211> LENGTH: 1068
<212> TYPE: DNA
<213> ORGANISM: Thielavia terrestris

<400> SEQUENCE: 21

```
atgaagctgt acctggcggc ctttctaggc gccgtcgcca ccccgggagc gttcgctcat       60
```

```
cgtaggttcc ccgtctatct ccctagggct agcaccacga ctaatttctc gtcgtccccc    120
tgtagaaatc cacgggattc tacttgtcaa cggcaccgaa acgccggaat ggaaatacgt    180
ccggtaatat ctaccttgct ctccttcttc cacaaccagc ctaacacatc atcagtgacg    240
tggcctggga gggcgcctac gaaccggaaa aataccccaa caccgagttc tttaagacgc    300
ccccgcagac ggacatcaac aacccgaaca tcacctgcgg caggaacgcg ttcgactcgg    360
ccagcaagac tgagacggcc gacatactgg ccggctcaga ggtcggcttc cgcgtctcgt    420
gggacggcaa cggcaagtac ggcgtgttct ggcatcccgg gccggggcag atctacctct    480
ctcgtgctcc gaacgacgac ctggaggact accgcggcga cggagactgg ttcaagatcg    540
caaccggcgc cgccgtctcc aataccgagt ggctgctgtg gaacaagcat gacgtgagcc    600
ccaacattcc tcgcccaatc gatccccaac ctggtcacca tggcggcgtc cgggatgcaa    660
agagactaac tccagaggaa cctacctagt tcaacttcac catccccaag acgacgccgc    720
cgggcaagta cctgatgcgc atcgagcagt tcatgccctc cacggtcgaa tacagccagt    780
ggtacgtcaa ctgcgcccac gtcaacatca tcggccccgg cggaggcacg ccgacgggct    840 tgccaggtt tcccggcacc tacactgttg acgatcccgg taagccggac ctaccggaca    900
cagaggcctc gggatagctt gctaaccttg tttgctctct ctcttttct ctcccgacta    960 ggcatcaagg tgccgttgaa ccagatcgtc aacagcggag agttgccgca ggaccaactg   1020
aggctgctcg agtacaagcc cccggggccca gcgctgtgga ctggttga                1068
```

<210> SEQ ID NO 22
<211> LENGTH: 257
<212> TYPE: PRT
<213> ORGANISM: Thielavia terrestris

<400> SEQUENCE: 22

```
Met Lys Leu Tyr Leu Ala Ala Phe Leu Gly Ala Val Ala Thr Pro Gly
1               5                   10                  15

Ala Phe Ala His Gln Ile His Gly Ile Leu Leu Val Asn Gly Thr Glu
            20                  25                  30

Thr Pro Glu Trp Lys Tyr Val Arg Asp Val Ala Trp Glu Gly Ala Tyr
        35                  40                  45

Glu Pro Glu Lys Tyr Pro Asn Thr Glu Phe Phe Lys Thr Pro Pro Gln
    50                  55                  60

Thr Asp Ile Asn Asn Pro Asn Ile Thr Cys Gly Arg Asn Ala Phe Asp
65                  70                  75                  80

Ser Ala Ser Lys Thr Glu Thr Ala Asp Ile Leu Ala Gly Ser Glu Val
                85                  90                  95

Gly Phe Arg Val Ser Trp Asp Gly Asn Gly Lys Tyr Gly Val Phe Trp
            100                 105                 110

His Pro Gly Pro Gly Gln Ile Tyr Leu Ser Arg Ala Pro Asn Asp Asp
        115                 120                 125

Leu Glu Asp Tyr Arg Gly Asp Gly Asp Trp Phe Lys Ile Ala Thr Gly
    130                 135                 140

Ala Ala Val Ser Asn Thr Glu Trp Leu Leu Trp Asn Lys His Asp Phe
145                 150                 155                 160

Asn Phe Thr Ile Pro Lys Thr Thr Pro Gly Lys Tyr Leu Met Arg
                165                 170                 175

Ile Glu Gln Phe Met Pro Ser Thr Val Glu Tyr Ser Gln Trp Tyr Val
            180                 185                 190

Asn Cys Ala His Val Asn Ile Ile Gly Pro Gly Gly Gly Thr Pro Thr
```

```
                    195                 200                 205
Gly Phe Ala Arg Phe Pro Gly Thr Tyr Thr Val Asp Asp Pro Gly Ile
                210                 215                 220
Lys Val Pro Leu Asn Gln Ile Val Asn Ser Gly Glu Leu Pro Gln Asp
225                 230                 235                 240
Gln Leu Arg Leu Leu Glu Tyr Lys Pro Pro Gly Pro Ala Leu Trp Thr
                245                 250                 255
Gly

<210> SEQ ID NO 23
<211> LENGTH: 32
<212> TYPE: DNA
<213> ORGANISM: Thielavia terrestris

<400> SEQUENCE: 23
actggattta ccatgaagtt ctcactggtg tc                                   32

<210> SEQ ID NO 24
<211> LENGTH: 38
<212> TYPE: DNA
<213> ORGANISM: Thielavia terrestris

<400> SEQUENCE: 24
tcacctctag ttaattaatc agcaggagat cggggcgg                             38

<210> SEQ ID NO 25
<211> LENGTH: 37
<212> TYPE: DNA
<213> ORGANISM: Thielavia terrestris

<400> SEQUENCE: 25
actggattta ccatgaggac gacattcgcc gccgcgt                              37

<210> SEQ ID NO 26
<211> LENGTH: 38
<212> TYPE: DNA
<213> ORGANISM: Thielavia terrestris

<400> SEQUENCE: 26
tcacctctag ttaattaact aagaagaagg ggcgcact                             38

<210> SEQ ID NO 27
<211> LENGTH: 36
<212> TYPE: DNA
<213> ORGANISM: Thielavia terrestris

<400> SEQUENCE: 27
actggattta ccatgaagct gagcgttgcc atcgcc                               36

<210> SEQ ID NO 28
<211> LENGTH: 38
<212> TYPE: DNA
<213> ORGANISM: Thielavia terrestris

<400> SEQUENCE: 28
tcacctctag ttaattaatt agcacgtctc agccggcg                             38

<210> SEQ ID NO 29
<211> LENGTH: 36
<212> TYPE: DNA
<213> ORGANISM: Thielavia terrestris
```

<400> SEQUENCE: 29
actggattta ccatgaagct gtcatcccag ctcgcc        36

<210> SEQ ID NO 30
<211> LENGTH: 38
<212> TYPE: DNA
<213> ORGANISM: Thielavia terrestris

<400> SEQUENCE: 30
tcacctctag ttaattaact agcactgaaa gaccgccg        38

<210> SEQ ID NO 31
<211> LENGTH: 32
<212> TYPE: DNA
<213> ORGANISM: Thielavia terrestris

<400> SEQUENCE: 31
actggattta ccatgccttc tttcgcctcc aa        32

<210> SEQ ID NO 32
<211> LENGTH: 38
<212> TYPE: DNA
<213> ORGANISM: Thielavia terrestris

<400> SEQUENCE: 32
tcacctctag ttaattaatc agtttgcctc ctcagccc        38

<210> SEQ ID NO 33
<211> LENGTH: 32
<212> TYPE: DNA
<213> ORGANISM: Thielavia terrestris

<400> SEQUENCE: 33
actggattta ccatgccgcc cgcactccct ca        32

<210> SEQ ID NO 34
<211> LENGTH: 38
<212> TYPE: DNA
<213> ORGANISM: Thielavia terrestris

<400> SEQUENCE: 34
tcacctctag ttaattaact aaccccgccg atcatacc        38

<210> SEQ ID NO 35
<211> LENGTH: 36
<212> TYPE: DNA
<213> ORGANISM: Thielavia terrestris

<400> SEQUENCE: 35
actggattta ccatgaagac attcaccgcc ctcctg        36

<210> SEQ ID NO 36
<211> LENGTH: 38
<212> TYPE: DNA
<213> ORGANISM: Thielavia terrestris

<400> SEQUENCE: 36
tcacctctag ttaattaatc agcaagtaaa gaccgccg        38

<210> SEQ ID NO 37
<211> LENGTH: 36
<212> TYPE: DNA
<213> ORGANISM: Thielavia terrestris

```
<400> SEQUENCE: 37
actggattta ccatggcctt gctgctcttg gcaggc                                36

<210> SEQ ID NO 38
<211> LENGTH: 38
<212> TYPE: DNA
<213> ORGANISM: Thielavia terrestris

<400> SEQUENCE: 38
tcacctctag ttaattaatc acccatccca tatcggcc                              38

<210> SEQ ID NO 39
<211> LENGTH: 36
<212> TYPE: DNA
<213> ORGANISM: Thielavia terrestris

<400> SEQUENCE: 39
actggattta ccatgatgcc gtccttgtt cgcttc                                 36

<210> SEQ ID NO 40
<211> LENGTH: 38
<212> TYPE: DNA
<213> ORGANISM: Thielavia terrestris

<400> SEQUENCE: 40
tcacctctag ttaattaatc aaccatgtct cctgtccc                              38

<210> SEQ ID NO 41
<211> LENGTH: 32
<212> TYPE: DNA
<213> ORGANISM: Thielavia terrestris

<400> SEQUENCE: 41
actggattta ccatgcagct cctcgtgggc tt                                    32

<210> SEQ ID NO 42
<211> LENGTH: 38
<212> TYPE: DNA
<213> ORGANISM: Thielavia terrestris

<400> SEQUENCE: 42
tcacctctag ttaattaatc agccactcca caccggcg                              38

<210> SEQ ID NO 43
<211> LENGTH: 36
<212> TYPE: DNA
<213> ORGANISM: Thielavia terrestris

<400> SEQUENCE: 43
actggattta ccatgaagct gtacctggcg gccttt                                36

<210> SEQ ID NO 44
<211> LENGTH: 38
<212> TYPE: DNA
<213> ORGANISM: Thielavia terrestris

<400> SEQUENCE: 44
tcacctctag ttaattaatc aaccagtcca cagcgctg                              38
```